(12) United States Patent
May

(10) Patent No.: US 11,154,233 B2
(45) Date of Patent: Oct. 26, 2021

(54) APPARATUS AND METHOD FOR DIFFERENTIATING WIDE COMPLEX HEART BEATS

(71) Applicant: MAYO FOUNDATION FOR MEDICAL EDUCATION AND RESEARCH, Rochester, MN (US)

(72) Inventor: Adam M. May, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 27 days.

(21) Appl. No.: 16/445,036

(22) Filed: Jun. 18, 2019

(65) Prior Publication Data

US 2019/0387992 A1   Dec. 26, 2019

Related U.S. Application Data

(60) Provisional application No. 62/688,265, filed on Jun. 21, 2018.

(51) Int. Cl.
    *A61B 5/0464*   (2006.01)
    *A61B 5/00*     (2006.01)
    (Continued)

(52) U.S. Cl.
    CPC ............. *A61B 5/363* (2021.01); *A61B 5/341* (2021.01); *A61B 5/366* (2021.01); *A61B 5/389* (2021.01); *A61B 5/7264* (2013.01)

(58) Field of Classification Search
    CPC . A61B 5/0464; A61B 5/04011; A61B 5/0472; A61B 5/0488; A61B 5/7264;
    (Continued)

(56) References Cited

U.S. PATENT DOCUMENTS 4,136,690 A    1/1979  Anderson et al.
4,202,340 A *  5/1980  Langer ............... A61B 5/046
                                              600/515

(Continued)

OTHER PUBLICATIONS

Mulpuru, S. K., Madhavan, M., McLeod, C. J., Cha, Y. M., & Friedman, P. A. (2017). Cardiac pacemakers: function, troubleshooting, and management: part 1 of a 2-part series. Journal of the American College of Cardiology, 69(2), Figures 4-6, Figure 15, p. 206-207 (Year: 2017).*

(Continued)

*Primary Examiner* — Erin M Piateski
(74) *Attorney, Agent, or Firm* — Daniel J. Chalker; Chalker Flores, LLP

(57) ABSTRACT

An apparatus and computerized method of classifying a wide complex heart beat(s) comprising: providing a computing device having an input/output interface, one or more processors and a memory; receiving one or more wide complex heart beat waveform amplitudes and/or time-voltage areas, and one or more baseline heart beat waveform amplitudes and/or time-voltage areas via the input/output interface or the memory; determining a signal change between the wide complex heart beat waveform amplitudes and/or time-voltage areas and the baseline heart beat waveform amplitudes and/or time-voltage areas using the one or more processors; and providing the signal change via the input/output interface, wherein the signal change provides an indication whether the wide complex heart beat(s) is from a ventricular source or a supraventricular aberrant condition.

46 Claims, 36 Drawing Sheets

(51) Int. Cl.
  *A61B 5/0472* (2006.01)
  *A61B 5/363* (2021.01)
  *A61B 5/341* (2021.01)
  *A61B 5/366* (2021.01)
  *A61B 5/389* (2021.01)

(58) Field of Classification Search
  CPC ... A61B 5/0468; A61B 5/0452; A61B 5/0456; A61B 5/04; A61B 5/363; A61B 5/389; A61B 5/366; A61B 5/341; G16H 50/20
  USPC .......................................................... 600/510
  See application file for complete search history.

(56) References Cited

U.S. PATENT DOCUMENTS

| | | | |
|---|---|---|---|
| 5,301,677 A | | 4/1994 | Hsung |
| 5,423,863 A * | | 6/1995 | Felblinger ............... A61B 5/046 607/5 |
| 6,393,316 B1 * | | 5/2002 | Gillberg .............. A61B 5/04525 600/515 |
| 6,480,734 B1 * | | 11/2002 | Zhang ................... A61N 1/3956 600/518 |
| 6,611,713 B2 | | 8/2003 | Schauerte |
| 7,123,954 B2 | | 10/2006 | Narayan et al. |
| 7,206,633 B2 | | 4/2007 | Saba |
| 7,330,757 B2 * | | 2/2008 | Ostroff .................. A61N 1/3956 607/5 |
| 7,894,893 B2 * | | 2/2011 | Kim ...................... A61B 5/7264 607/4 |
| 8,301,233 B2 * | | 10/2012 | Zhang .................. A61B 5/0452 600/515 |
| 8,437,851 B2 | | 5/2013 | Corbucci et al. |
| 8,483,808 B2 * | | 7/2013 | Dong ................. A61B 5/04525 600/509 |
| 8,909,332 B2 | | 12/2014 | Vitali et al. |
| 9,486,637 B2 * | | 11/2016 | Greenhut .................. A61N 1/37 |
| 9,808,640 B2 * | | 11/2017 | Zhang ................... A61N 1/3987 |
| 9,828,640 B2 * | | 11/2017 | Cao ...................... C12Q 1/6883 |
| 2003/0083587 A1 | | 5/2003 | Ferek-Petric |
| 2004/0059237 A1 * | | 3/2004 | Narayan ............ A61B 5/04525 600/509 |
| 2004/0106956 A1 | | 6/2004 | Sharma et al. |
| 2010/0249626 A1 | | 9/2010 | El Arab et al. |
| 2014/0039332 A1 | | 2/2014 | Min et al. |
| 2018/0168471 A1 * | | 6/2018 | Hanuliak ............. A61B 5/0472 |

OTHER PUBLICATIONS

Becker, D. E. (2006). Fundamentals of electrocardiography interpretation. Anesthesia progress, 53(2), 53-64.Figures 4-6, Figure 15, p. 206-207 (Year: 2006).*

Meek, S., & Morris, F. (2002). ABC of clinical electrocardiography. Introduction. I-Leads, rate, rhythm, and cardiac axis. BMJ (Clinical research ed.), 324(7334), 415-418. https://doi.org/10.1136/bmj.324.7334.415 (Year: 2002).*

Yang, H., Bukkapatnam, S.T. & Komanduri, R. Spatiotemporal representation of cardiac vectorcardiogram (VCG) signals. BioMed Eng Online 11, 16 (2012). https://doi.org/10.1186/1475-925X-11-16 (Year: 2012).*

Lyon A, Minchole A, Martinez JP, Laguna P, Rodriguez B. 2018 Computational techniques for ECG analysis and interpretation in light of their contribution to medical advances. J. R. Soc. Interface 15: 20170821, pp. 14-15 (Year: 2021).*

Akhtar, et al., "Wide QRS Complex Tachycardia Reappraisal of a Common Clinical Problem", Clinical Review, 1988, American College of Physicians.

Alberca et al., "Evaluation of the Specificity of Morphological Electrocardiographic Criteria for the Differential Diagnosis of Wide QRS Complex Tachycardia in Patients With Intraventricular Conduction Defects", American Heart Association, vol. 96, Issue 10, Nov. 1997, pp. 3527-3533, Cir. 96.

Baxi et al., "Vereckei criteria as a diagnostic tool amongst emergency medicine residents to distinguish between ventricular tachycardia and supra-ventricular tachycardia with aberrancy", Elsevier, Journal of Cardiology, 2012, 59, 307-312.

Brugada et al., "A New Approach to the Diferential Diagnosis of a Regular Tachycardia With a Wide QRS Complex", Circulation vol. 83, No. 5, May 1991.

Ceresnak et al., "Are wide complex tachycardia algorithms applicable in children and patients with congenital heart disease?", ScienceDirect, Journal of Electrocardilogy, 43, 2010, 694-700.

Datino et al., "Specificity of electrocardiographic criteria for the differential diagnosis of wide QRS complex tachycardia in patients with intraventricular conduction defect", (Heart Rhythm 2013;10:1393-1401) © 2013 Published by Elsevier Inc. on behalf of Heart Rhythm Society.

Dongas et al., "Value of Preexisting Bundle Branch Block in the Electrocardiographic Differentiation of Supraventricular from Ventricular Origin of Wide QRS Tachycardia", (Am J Cardiol 1985;55:717-721).

Drew et al., ECG Criteria to Distinguish Between Aberrantly Conducted Supraventricular Tachycardia and Ventricular Tachycardia: Practical Aspects for the Immediate Care Setting, Dec. 1995, Part I, vol. 18.

Griffith, et al., "Multivariate Analysis to Simplify the Differential Diagnosis of Broad Complex Tachycardia", By Heart, J, 1991, 66, 166-74.

Griffith et al., "Difficulties in the use of electrocardiographic criteria for the differential diagnosis of left bundle branch block pattern tachycardia in patients with a structurally normal heart", European Heart Journal (1992) 13, 478-483.

Griffith, et al., "Ventricular tachycardia as default diagnosis in broad complex tachycardia", The Lancet, vol. 343, 1994.

Herbert, et al., Failure to Agree on the Electrocardiographic Diagnosis of Ventricular Tachycardia, Cardiovascular/Brief Report, Jan. 1996 27:1 Annals of Emergency Medicine.

Isenhour, et al., "Wide-complex Tachycardia: Continued Evaluation of Diagnostic Criteria", Academic Emergency Medicine • Jul. 2000, vol. 7, No. 7.

Jastrzebski, et al., "Specificity of the wide QRS complex tachycardia algorithms in recipients of cardiac resynchronization therapy", Journal of Electrocardiology 45 (2012) 319-326.

Jastrzebski, et al., "Comparison of five electrocardiographic methods for differentiation of wide QRS-complex tachycardias", Europace (2012) 14, 1165-1171, Clinical Research Electrophysiology and Ablation.

Jastrzebski, et al., "The ventricular tachycardia score: a novel approach to electrocardiographic diagnosis of ventricular tachycardia", Europace (2016) 18, 578-584 doi:10.1093/europace/euv118, Clinical Research, Cardiac electrophysiology.

Kaiser, et al., "Differential diagnosis of wide QRS tachycardias: comparison of two electrocardiographic algorithms" Europace (2015) 17, 1422-1427 doi:10.1093/europace/euu354, Clinical Research, Cardiac electrophysiology.

Kindwall, et al., "ElectrocardiographiCc riteria for Ventricular Tachycardiain WideC omplexl eft BundleB ranch Block Morphology Tachycardias", (Am J Cardiol 1988;61:1279-1283).

Lau, et al., "The Bayesian Approach Improves the Electrocardiographic Diagnosis of Broad Complex Tachycardia", Oct. 2000, Part I, vol. 23.

Lau, et al., "Comparison of the Performance of Three Diagnostic Algorithms for Regular Broad Complex Tachycardia in Practical Application", Journal of Pacing and Clinical Electrophysiology, vol. 25, No. 5, May 2002.

May, et al., "Electrocardiogram algorithms used to differentiate wide complex tachycardias demonstrate diagnostic limitations when applied by non-cardiologists", Journal of Electrocardiology 51 (2018) 1103-1109.

May, et al., "The WCT Formula: A novel algorithm designed to automatically differentiate wide-complex tachycardias", Journal of Electrocardiology 54 (2019) 61-68.

(56) References Cited

OTHER PUBLICATIONS

Miller, et al., "Value of the 12-Lead ECG in Wide QRS Tachycardia", Cardiol Clin 24 (2006) 439-451, Elsevier.
Pava, et al., "R-wave peak time at DII: A new criterion for differentiating between wide complex QRS tachycardias", (Heart Rhythm 2010;7:922-926) 2010 Heart Rhythm Society.
Sandler, et al., "The Differential Morphology of Anomalous Ventricular Complexes of RBBB-Type in Lead V1 Ventricular Ectopy versus Aberration" Circulation, vol. XXXI, Apr. 1965.
Kenichi Sasaki, "Abstract 2650: A New, Simple Algorithm for Diagnosing Wide QRS Complex Tachycardia: Comparison with Brugada, Vereckei and VR algorithms", Home Circulation, vol. 120, No. suppl_18.
Gunters, et al., "The Differential Diagnosis on the Electrocardiogram Between Ventricular Tachycardia and Preexcited Tachycardia", Clin. Cardiol. 17, 306-308 (1994).
Swanick, et al., "Morphologic Features of Right Ventricular Ectopic Beats", Dec. 1972 The American Journal of Cardiology, vol. 30.
Vereckei, et al., "Application of a new algorithm in the differential diagnosis of wide QRS complex tachycardia", European Heart Journal (2007) 28, 589-600, Clinical research Arrhythmia/electrophysiology.
Vereckei, et al., New algorithm using only lead aVR for differential diagnosis of wide QRS complex tachycardia, 2008 Heart Rhythm Society, 1547-5271.
Wellens, etl al., "The Value of the Electrocardiogram in the Differential Diagnosis of a Tachycardia with a Widened QRS Complex", The American Journal of Medicine, vol. 64, Jan. 1978.

\* cited by examiner

P = Probability of VT
$X_x$ = Independent WCT predictor
$\beta_x$ = Slope of independent WCT predictor
$\beta_0$ = Y intercept or Constant
$X_\beta = \mathbf{Ln}\left(\frac{P}{1-P}\right)$ = Weighted Sum of WCT predictors $$X_\beta = \beta_0 + \beta_1 X_1 + \beta_2 X_2 + \beta_3 X_3 = \mathrm{Ln}\left(\frac{P}{1-P}\right)$$

$$X_\beta = -14.5607 + \underbrace{(\text{WCT duration})(0.0627)}_{\text{WCT Duration}} + \underbrace{(\text{Frontal PAC})(0.0284)}_{\text{Frontal PAC}} + \underbrace{(\text{Horizontal PAC})(0.0395)}_{\text{Horizontal PAC}}$$

$$\underbrace{P}_{\text{VT Probability}} = \left(\frac{e^{-14.5607+(\text{WCT duration})(0.0627)+(\text{Frontal PAC})(0.0284)+(\text{Horizontal PAC})(0.0395)}}{1+e^{-14.5607+(\text{WCT duration})(0.0627)+(\text{Frontal PAC})(0.0284)+(\text{Horizontal PAC})(0.0395)}}\right) = \left(\frac{e^{X_\beta}}{1+e^{X_\beta}}\right)$$

FIG. 6C

| Derivation Cohort (Table 1) ECG characteristics | SWCT (N=168) | VT (N=160) | Total (N=328) | P-value |
|---|---|---|---|---|
| Diagnosing Provider[a] | | | | |
| Heart rhythm cardiologists | 75 (44.6) | 150 (93.8) | 225 (68.6) | <0.001 |
| Non-heart rhythm cardiologists | 54 (32.1) | 5 (3.1) | 59 (18.0) | |
| Non-cardiologists | 39 (23.2) | 5 (3.1) | 44 (13.4) | |
| Time Separation (hours) | | | | |
| Mean (SD) | 572.9 (2906.5) | 172.4 (695.7) | 376.9 (2139.5) | |
| Median | 10.6 | 9.2 | 9.5 | 0.14 |
| Q1, Q3 | 1.4, 46.1 | 1.0, 51.4 | 1.2, 51.4 | |
| Range | (0.0-29800.2) | (0.0-5307.5) | (0.0-29800.2) | |
| Time Separation | | | | |
| <3 hours | 60 (35.7) | 66 (41.3) | 126 (38.4) | 0.30 |
| <24 hours | 49 (29.2) | 33 (20.6) | 82 (25.0) | 0.07 |
| <30 days | 41 (24.4) | 55 (34.2) | 96 (29.3) | 0.05 |
| Mirror ECG[a] | 18 (10.7) | 6 (3.8) | 24 (7.3) | 0.02 |
| ECG Lab Interpretation[a] | | | | |
| Definite VT | 5 (3.0) | 125 (78.1) | 130 (39.6) | <0.001 |
| Probable VT | 13 (7.7) | 20 (12.5) | 33 (10.0) | |
| Definite SWCT | 119 (70.8) | 3 (1.9) | 122 (37.2) | |
| Possible SWCT | 11 (6.5) | 3 (1.9) | 14 (4.3) | |
| Unidentified rhythm | 20 (11.9) | 9 (5.6) | 29 (8.8) | |
| Electrophysiology Procedure[a] | | | | |
| Yes | 25 (14.9) | 82 (51.3) | 107 (32.6) | <0.001 | a Percentage within derivation cohort (%)

FIG. 9

| Derivation Cohort (table 2) Clinical characteristics | SWCT (N=168) | VT (N=160) | Total (N=344) | P-value |
|---|---|---|---|---|
| Age (years) | | | | |
| Mean (SD) | 71.5 (13.2) | 66.1 (13.7) | 68.8 (13.6) | 0.002 |
| Range | (22 - 98) | (30 - 90) | (22 - 98) | |
| Gender * | | | | |
| Male | 106 (63.1) | 130 (82.2) | 236 (72.0) | <0.001 |
| Female | 62 (36.9) | 30 (17.8) | 92 (28.0) | |
| Clinical Characteristics † | | | | |
| Coronary Artery Disease | 79 (47.0) | 105 (65.6) | 184 (56.1) | <0.001 |
| Prior Myocardial Infarction | 45 (26.8) | 90 (56.3) | 135 (41.2) | <0.001 |
| Prior cardiac surgery | 55 (32.7) | 73 (44.6) | 128 (39.0) | 0.02 |
| Congenital Heart Disease | 8 (4.8) | 15 (9.4) | 23 (7.0) | 0.10 |
| Antiarrhythmic drug use | 16 (9.5) | 96 (60.0) | 112 (34.2) | <0.001 |
| Ischemic cardiomyopathy | 30 (17.9) | 76 (47.5) | 106 (32.3) | <0.001 |
| Non-ischemic cardiomyopathy | 39 (23.2) | 54 (33.8) | 93 (28.4) | 0.03 |
| AICD | 7 (4.2) | 107 (66.9) | 114 (34.8) | <0.001 |
| Pacemaker | 15 (8.9) | 3 (1.9) | 18 (5.5) | 0.005 |
| Left Ventricular Ejection Fraction (%) ‡ | | | | |
| LVEF (<=35) | 97 (57.7) | 34 (21.3) | 131 (39.9) | <0.001 |
| LVEF (36-50) | 25 (14.9) | 46 (28.8) | 71 (21.7) | |
| LVEF (>50) | 43 (25.6) | 80 (50.0) | 123 (37.5) | |
| Unknown LVEF | 3 (1.8) | 0 (0.0) | 3 (0.9) | |
| Baseline ECG* | | | | |
| Baseline bundle branch block | 110 (65.5) | 29 (18.1) | 139 (42.4) | <0.001 |
| Baseline ventricular pacing | 10 (6.0) | 69 (43.1) | 79 (24.1) | <0.001 |

*Percentages within derivation cohort group (%)

FIG. 10

| Derivation cohort (table 3) ECG analysis | SWCT (N=168) | VT (N=160) | Total (N=328) | P-value |
|---|---|---|---|---|
| Baseline QRS duration (ms) | 136.3 (27.9) | 147 (43.7) | 141.6 (36.8) | 0.05 |
| Baseline QTc duration (ms) | 482.4 (42.9) | 500.2 (62.8) | 490.9 (54.1) | 0.05 |
| WCT QRS duration (ms) | 144.0 (18.1) | 177.4 (32.4) | 160.3 (30.9) | <0.001 |
| Change in QRS duration (ms) | 9.7 (36.3) | 30.2 (48.4) | 19.7 (43.8) | <0.001 |
| Change in R-wave axis (°) | 25.4 (32.7) | 82.5 (56.5) | 53.3 (54.0) | <0.001 |
| Change in T-wave axis (°) | 41.7 (42.2) | 87.4 (58.2) | 64.0 (55.5) | <0.001 |
| Frontal PAC (%) | 34.9 (28.5) | 123.7 (86.4) | 78.2 (77.6) | <0.001 |
| Horizontal PAC (%) | 44.2 (25.0) | 116.0 (62.5) | 79.2 (59.2) | <0.001 |

* Values represent mean (SD)

FIG. 11

Electrocardiographic Variables Among Baseline ECG Sub-groups

| Electrocardiographic Measurement | Baseline QRS duration < 120 ms VT (n = 55) SWCT (n = 42) | | | Baseline QRS duration ≥ 120 ms VT (n = 105) SWCT (n = 116) | | | Baseline Ventricular Pacing VT (n = 69) SWCT (n = 10) | | |
|---|---|---|---|---|---|---|---|---|---|
| | VT | SWCT | P value | VT | SWCT | P value | VT | SWCT | P value |
| WCT Duration (ms) | 171.1 (32.8) | 143.1 (20.0) | <0.001 | 180.6 (31.9) | 144.3 (17.5) | <0.001 | 187.2 (26.4) | 157.2 (17.7) | <0.001 |
| Change in WCT duration (ms) | 71.4 (32.1) | 41.5 (21.1) | <0.001 | 31.9 (26.8) | 10.9 (16.4) | <0.001 | 37.5 (30.7) | 23.0 (45.0) | 0.19 |
| Change in frontal R wave axis (°) | 93.6 (50.0) | 45.1 (47.6) | <0.001 | 76.7 (59.0) | 18.8 (22.6) | <0.001 | 90.2 (58.2) | 26.6 (26.7) | <0.001 |
| Frontal PAC (%) | 116.5 (58.5) | 47.0 (25.1) | <0.001 | 127.5 (98.0) | 30.9 (28.6) | <0.001 | 135.8 (94.6) | 61.9 (75.6) | 0.004 |
| Horizontal PAC (%) | 129.3 (76.0) | 57.9 (26.7) | <0.001 | 109.0 (56.0) | 39.7 (22.7) | <0.001 | 123.6 (66.4) | 49.2 (25.4) | <0.001 |

FIG. 12D

| WCT event characteristics Validation Cohort (table 4) | SWCT (N=190) | VT (N=123) | Total (N=313) | P-value |
|---|---|---|---|---|
| Diagnosing Provider* | | | | |
| Heart rhythm specialists | 83 (43.7) | 108 (87.8) | 191 (61.0) | <0.001 |
| Non-Heart rhythm cardiologists | 64 (33.7) | 12 (9.8) | 76 (24.3) | |
| Non-cardiologists | 43 (22.6) | 3 (2.4) | 46 (14.7) | |
| Time Separation (hours) | | | | |
| Mean (SD) | 155.6 (848.2) | 134.4 (507.1) | 147.3 (733.0) | 0.45 |
| Median | 4.7 | 4.8 | 4.7 | |
| Q1, Q3 | 0.7-28.1 | 1.0-45.3 | 0.9-33.9 | |
| Range | 0.02-10097.1 | 0.1-4383.9 | 0.02-10097.1 | |
| Time Separation† | | | | |
| <1 hours | 88 (46.3) | 51 (41.5) | 139 (44.4) | 0.40 |
| <24 hours | 50 (26.3) | 33 (26.8) | 83 (26.5) | 0.92 |
| <30 days | 42 (22.1) | 33 (26.8) | 75 (24.0) | 0.34 |
| ≥30 days | 10 (5.3) | 6 (4.9) | 16 (5.1) | 0.88 |
| ECG lab interpretation* | | | | |
| Definite VT | 5 (2.6) | 109 (88.6) | 114 (36.4) | <0.001 |
| Probable VT | 3 (1.6) | 6 (4.9) | 9 (2.9) | |
| Definite SWCT | 171 (90.0) | 4 (3.3) | 175 (55.9) | |
| Probable SWCT | 7 (3.7) | 2 (1.6) | 9 (2.9) | |
| Undetermined | 4 (2.1) | 2 (1.6) | 6 (1.9) | |
| Electrophysiology Procedure* | | | | |
| Yes | 33 (17.4) | 63 (51.2) | 96 (30.7) | <0.001 |

*Percentage within validation cohort (%)

FIG. 14

| Clinical Characteristics Validation Cohort (table 5) | SWCT (N=190) | VT (n=124) | Total (N=314) | P-value |
|---|---|---|---|---|
| Age (mean) | 70.1 (15.4) | 65.7 (12.4) | 68.4 (14.4) | <0.001 |
| Range | (18 - 92) | (27 - 88) | (18 - 92) | |
| Gender | | | | |
| Male | 129 (67.9) | 105 (85.4) | 234 (74.8) | <0.001 |
| Female | 61 (32.1) | 18 (14.6) | 79 (25.2) | |
| Clinical Characteristics | | | | |
| Coronary artery disease | 95 (50.0) | 91 (74.0) | 186 (59.4) | <0.001 |
| Hypertension | 50 (26.3) | 74 (60.2) | 124 (39.6) | <0.001 |
| Prior CABG surgery | 74 (39.0) | 49 (39.8) | 123 (39.3) | 0.87 |
| Congenital heart disease | 11 (5.8) | 5 (4.1) | 16 (5.1) | 0.50 |
| Antiarrhythmic drug use | 37 (19.5) | 73 (59.4) | 110 (35.1) | <0.001 |
| Ischemic cardiomyopathy | 23 (12.1) | 69 (56.1) | 92 (29.4) | <0.001 |
| Nonischemic cardiomyopathy | 45 (23.7) | 35 (28.5) | 80 (25.6) | 0.34 |
| AICD | 15 (7.9) | 74 (60.2) | 89 (28.4) | <0.001 |
| Pacemaker | 16 (8.4) | 2 (1.6) | 18 (5.8) | 0.01 |
| Left Ventricular Ejection Fraction (%) | | | | |
| LVEF (≥50) | 113 (59.5) | 37 (30.1) | 150 (47.9) | <0.001 |
| LVEF (40-50) | 41 (21.6) | 40 (32.5) | 81 (25.9) | |
| LVEF (<40) | 24 (12.6) | 44 (35.8) | 68 (21.7) | |
| LVEF Unknown | 12 (6.3) | 2 (1.6) | 14 (4.5) | |
| Baseline ECG | | | | |
| Baseline Sinus Rhythm at start | 130 (68.4) | 15 (12.2) | 145 (46.3) | <0.001 |
| Baseline ventricular paced | 10 (5.3) | 42 (34.2) | 52 (16.6) | <0.001 |

FIG. 15

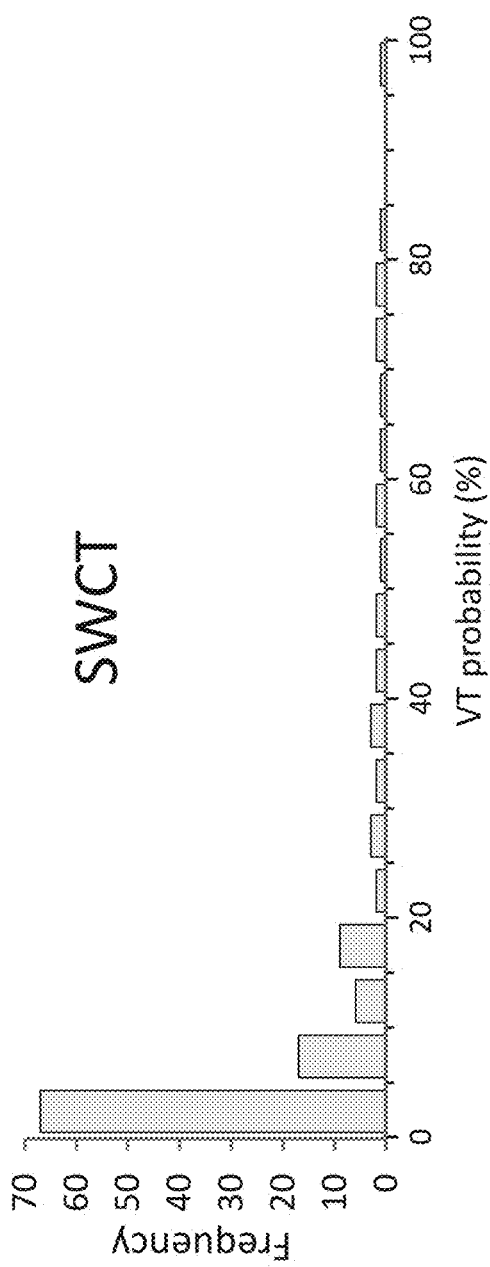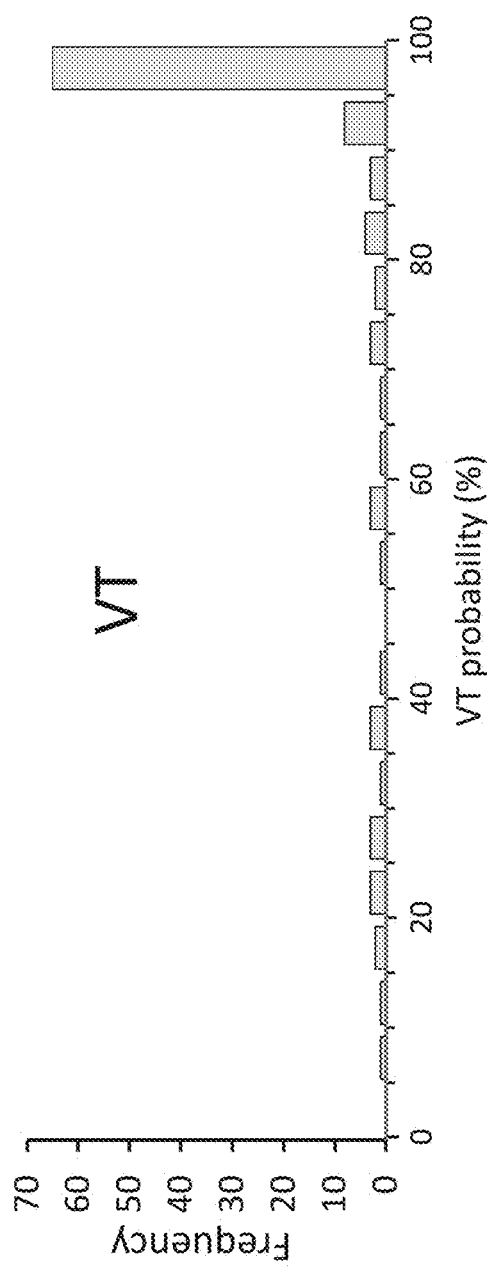
FIG. 16A
FIG. 16B

| VT Probability Cutpoint # (Table 6) | Accuracy (%) | Sensitivity (%)* | Specificity (%) | (+) Likelihood Ratio | (-) Likelihood Ratio |
|---|---|---|---|---|---|
| 99 % | 78.91 | 47.97 (38.88 - 57.16) | 98.95 (96.25 - 99.87) | 45.57 (11.34 - 183.11) | 0.53 (0.44 - 0.62) |
| 50 % | 90.42 | 77.24 (68.81 - 84.31) | 98.95 (96.25 - 99.87) | 73.37 (18.42 - 292.22) | 0.23 (0.17 - 0.32) |
| 75 % | 90.73 | 82.11 (74.18 - 88.44) | 96.32 (92.56 - 98.51) | 22.29 (10.72 - 46.33) | 0.19 (0.13 - 0.27) |
| 50 % | 92.01 | 89.43 (82.60 - 94.25) | 93.68 (89.23 - 96.69) | 14.16 (8.16 - 24.57) | 0.11 (0.07 - 0.19) |
| 25 % | 89.14 | 94.31 (88.63 - 97.68) | 85.79 (80.00 - 90.42) | 6.64 (4.67 - 9.44) | 0.07 (0.03 - 0.14) |
| 10 % | 81.78 | 96.75 (91.88 - 99.11) | 72.11 (65.15 - 78.35) | 3.47 (2.75 - 4.37) | 0.05 (0.02 - 0.12) |
| 1 % | 50.16 | 100.00 (97.05 - 100.00) | 17.37 (12.27 - 23.52) | 1.21 (1.13 - 1.29) | 0.00 |

* Active according to VT diagnosis
Confidence Interval at 95 (α)

FIG. 17

"clinical SWCT" classified as VT

| Formula Diagnosis | Clinical Diagnosis | ECG Laboratory Diagnosis | WCT Formula VT Probability (%) | Frontal PAC (%) | Horizontal PAC (%) | Baseline ECG QRS duration | Baseline ECG Frontal R Axis (°) | Baseline ECG V1 QRS Morphology | Baseline ECG V6 QRS morphology | Baseline ECG Precordial Transition | WCT QRS duration (ms) | WCT Frontal R Axis (°) | WCT V1 QRS Morphology | WCT V6 QRS morphology | WCT Precordial Transition |
|---|---|---|---|---|---|---|---|---|---|---|---|---|---|---|---|
| VT | SWCT | Definite VT | 0.99945 | 146.000 | 221.877 | 104 | 129 | rS | qrs | V5 | 146 | -76 | rS | qR | V6 |
| VT | SWCT | Definite SWCT | 0.99442 | 144.478 | 157.844 | 158 | 82 | QS | QS | none | 150 | 118 | rsR | RS | None |
| VT | SWCT | Definite VT | 0.89827 | 97.656 | 67.834 | 86 | 22 | rS | Rs | V3 | 180 | -62 | rS | qRs | V5 |
| VT | SWCT | Definite SWCT | 0.89372 | 84.193 | 142.417 | 136 | 43 | QS | qRs | V5 | 134 | -70 | rS | R | V5 |
| VT | SWCT | Definite SWCT | 0.83415 | 118.900 | 104.656 | 174 | 63 | QS | R | V5 | 136 | -28 | qR | Rs | None |
| VT | SWCT | Definite SWCT | 0.78983 | 84.320 | 62.144 | 122 | 8 | rS | qR | V5 | 176 | -52 | rS | Rsr | V6 |
| VT | SWCT | Definite SWCT | 0.77830 | 84.173 | 85.923 | 118 | 1 | rS | qR | V4 | 160 | -35 | rS | RS | VG |
| VT | SWCT | Definite SWCT | 0.68131 | 96.304 | 96.368 | 100 | 10 | rS | Rs | V3 | 140 | 56 | R | R | None |
| VT | SWCT | Definite SWCT | 0.61609 | 29.959 | 105.085 | 168 | -28 | QS | R | V6 | 160 | -70 | rS | rS | None |
| VT | SWCT | Definite SWCT | 0.60446 | 29.008 | 80.273 | 118 | -46 | rS | Rs | V5 | 178 | -52 | rS | rS | None |
| VT | SWCT | Definite SWCT | 0.56497 | 97.282 | 41.799 | 108 | 19 | rS | qR | V5 | 166 | -37 | rS | rSr | None |
| VT | SWCT | Definite SWCT | 0.51957 | 62.594 | 48.899 | 154 | -19 | QS | R | V5 | 174 | -58 | QS | qrs | None |

FIG. 19A

"clinical VT" classified as SWCT

| Formula Diagnosis | Clinical Diagnosis | ECG Laboratory Diagnosis | WCT Formula VT Probability (%) | Frontal PAC (%) | Horizontal PAC (%) | Baseline ECG QRS duration | Baseline ECG Frontal R Axis (°) | Baseline ECG V1 QRS Morphology | Baseline ECG V6 QRS morphology | Baseline ECG Precordial Transition | WCT QRS duration (ms) | WCT Frontal R Axis (°) | WCT V1 QRS Morphology | WCT V6 QRS morphology | WCT Precordial Transition |
|---|---|---|---|---|---|---|---|---|---|---|---|---|---|---|---|
| SWCT | VT | Probable SWCT | 0.48237 | 46.650 | 111.071 | 116 | -8 | rS | qR | V6 | 140 | 57 | rS | RS | V6 |
| SWCT | VT | Definite VT | 0.47085 | 28.424 | 53.163 | 136 | -15 | RSR | RS | V2 | 184 | -32 | R | QRs | None |
| SWCT | VT | Definite VT | 0.46747 | 24.642 | 80.935 | 188 | 52 | rS | R | V4 | 168 | 72 | rS | qR | V4 |
| SWCT | VT | Definite VT | 0.42298 | 44.369 | 108.675 | 170 | -86 | R | rS | V3 | 140 | -63 | R | RS | None |
| QS | VT | Definite VT | 0.31679 | 99.149 | 81.050 | 98 | -18 | rS | qR | V4 | 124 | -51 | QS | Rs | V2 |
| SWCT | VT | Definite VT | 0.26450 | 35.826 | 85.223 | 88 | -39 | rS | qRs | V2 | 146 | 36 | rS | QS | V4 |
| SWCT | VT | Definite VT | 0.23879 | 65.972 | 75.964 | 118 | 74 | rS | qR | V5 | 136 | 29 | QS | R | V3 |
| SWCT | VT | Definite VT | 0.19431 | 114.122 | 48.912 | 132 | 18 | rS | qRs | V3 | 126 | -45 | rSr | qRs | V2 |
| SWCT | VT | Definite VT | 0.18438 | 37.407 | 78.684 | 84 | -61 | rS | RS | V4 | 142 | -81 | R | RS | V5 |
| SWCT | VT | Definite SWCT | 0.08858 | 37.588 | 45.260 | 146 | -71 | rSr | rS | None | 154 | 74 | qR | rS | V3 |
| SWCT | VT | Definite VT | 0.06132 | 65.530 | 55.606 | 140 | 84 | rSr | Rs | V4 | 124 | 81 | QS | R | V2 |
| SWCT | VT | Definite VT | 0.03454 | 81.152 | 19.608 | 110 | -53 | rSr | Rs | V6 | 130 | 28 | QS | RS | V5 |
| SWCT | VT | Definite VT | 0.02994 | 29.765 | 49.641 | 110 | -59 | rS | qRs | V3 | 132 | -61 | QS | RS | V5 |

FIG. 19B

- P = Probability of VT
- $X_x$ = Independent WCT predictor
- $β_x$ = Slope of independent WCT predictor
- $β_0$ = Y intercept or Constant
- $X_β = Ln\left(\frac{P}{1-P}\right)$ = Weighted Sum of WCT predictors $$X_β = β_0 + β_1 X_1 + β_2 X_2 + β_3 X_3 = Ln\left(\frac{P}{1-P}\right)$$

$$X_β = -11.04775 + \underbrace{(\text{WCT duration})(0.051762)}_{\text{WCT Duration}} + \underbrace{(\text{Frontal PAC})(0.01675701) + (\text{Frontal PTVAC})(0.01675701)}_{\text{Frontal PTVAC}} + \underbrace{(\text{Horizontal PAC})(0.00868261) + (\text{Horizontal PTVAC})(0.00868261)}_{\text{Horizontal PTVAC}}$$

$$\underbrace{P =}_{\text{VT Probability}} \left(\frac{e^{-11.04775+(\text{WCT duration})(0.051762)+(\text{Frontal PTVAC})(0.01675701)+(\text{Horizontal PTVAC})(0.00868261)}}{1+e^{-11.04775+(\text{WCT duration})(0.051762)+(\text{Frontal PTVAC})(0.01675701)+(\text{Horizontal PTVAC})(0.00868261)}}\right) = \left(\frac{e^{X_β}}{1+e^{X_β}}\right)$$

FIG. 23C

APPARATUS AND METHOD FOR DIFFERENTIATING WIDE COMPLEX HEART BEATS

CROSS-REFERENCE TO RELATED APPLICATIONS

This non-provisional patent application claims priority to U.S. Provisional Patent Application Ser. No. 62/688,265, filed Jun. 21, 2018, entitled "Apparatus and Method for Differentiating Wide Complex Heart Beats," the contents of which is incorporated by reference herein in its entirety.

TECHNICAL FIELD OF THE INVENTION

The present invention relates in general to heart rhythms, and more particularly, to an apparatus and method for differentiating wide complex heart beats.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with classifying wide complex tachycardia (WCT).

The successful differentiation of wide complex tachycardias (WCTs) into ventricular tachycardia (VT) or supraventricular wide complex tachycardia (SWCT) has undeniably important therapeutic and prognostic implications. Ventricular tachycardia (VT) is an abnormal rapid heart rhythm that is often dangerous. Supraventricular wide complex tachycardia (SWCT) is a similar appearing abnormal rapid heart rhythm that is typically less hazardous.

The 12-lead electrocardiogram (ECG) is the most practical test to non-invasively differentiate VT and SWCT, in part, because it is one of the most commonly used diagnostic tests performed in medicine (~300 million ECGs are performed each year in the United states). Unfortunately, the differentiation of VT and SWCT remains problematic despite the availability of numerous manually-operated ECG criteria and algorithms (1-15). These manual interpretation methods do not perform well when used be less experienced ECG interpreters. In fact, few clinicians, aside from expert electrocardiographers, are able use manual methods with reliable accuracy. In addition, published conventional ECG interpretation methods are limited by their (1) compulsory need for manual ECG interpretation, (2) inability to estimate VT probability and (3) uncertain diagnostic performance when applied on WCTs regularly encountered in clinical practice.

SUMMARY OF THE INVENTION

The present invention is able to accurately distinguish VT and SWCT without the need for manual ECG, electrogram (EMG) and/or vectorcardiogram (VCG) interpretation or calculation. The present invention provides an apparatus and method for wide complex beat differentiation that can be automatically implemented using data provided by contemporary ECG, EMG and/or VCG interpretation software.

One embodiment of the present invention provides a computerized method of classifying a wide complex heart beat(s) comprising: providing a computing device having an input/output interface, one or more processors and a memory; receiving one or more wide complex heart beat waveform amplitudes and/or time-voltage areas, and one or more baseline heart beat waveform amplitudes and/or time-voltage areas via the input/output interface or the memory; determining a signal change between the wide complex heart beat waveform amplitudes and/or time-voltage areas and the baseline heart beat waveform amplitudes and/or time-voltage areas using the one or more processors; and providing the signal change via the input/output interface, wherein the signal change provides an indication whether the wide complex heart beat(s) is from a ventricular source or a supraventricular aberrant condition.

In one aspect, the signal change further provides the indication whether the wide complex heart beat(s) is due to ventricular pacing. In another aspect, the wide complex heart beat(s) comprise a wide complex tachycardia (WCT), the ventricular source comprises a ventricular tachycardia (VT), and the supraventricular aberrant condition comprises a supraventricular wide complex tachycardia (SWCT). In another aspect, providing the signal change via the input/output interface comprises: automatically determining a wide complex heart beat classification for the wide complex heart beat(s) by comparing the signal change to a predetermined value using the one or more processors, wherein the wide complex heart beat classification comprises a ventricular source or a supraventricular aberrant condition; and providing the wide complex heart beat classification via the input/output interface. In another aspect, the signal change comprises a VT probability, the wide complex heart beat classification comprises a VT whenever the VT probability is greater than or equal to the predetermined value, and the wide complex heart beat classification comprises a SWCT whenever the VT probability is less than the predetermined value. In another aspect, the method further comprises selecting the predetermined value from a range of 0% to 100%. In another aspect, the predetermined value comprises about 1%, 10%, 25%, 50%, 75%, 90% or 99%. In another aspect, providing the signal change comprises providing a "shock" signal, a "no shock" signal, or no signal. In another aspect, the method further comprises obtaining the wide complex heart beat waveform amplitudes and/or time-voltage areas and the baseline heart beat waveform amplitudes and/or time-voltage areas from an electrocardiogram (ECG) QRS signal, a ventricular electrogram (EMG) signal, and/or a vectorcardiogram (VCG) signal. In another aspect, the wide complex heart beat waveform amplitudes and/or time-voltage areas comprise a plurality of measured amplitudes and/or time-voltage areas of a ECG QRS waveform, a EMG waveform and/or a VCG waveform above and below an isoelectric baseline; and the baseline heart beat waveform amplitudes and/or time-voltage areas comprise a plurality of measured amplitudes and/or time-voltage areas of a baseline ECG QRS waveform, a baseline EMG waveform and/or a baseline VCG waveform above and below the isoelectric baseline.

In another aspect, receiving the one or more wide complex heart beat waveform amplitudes and/or time-voltage areas, and one or more baseline heart beat waveform amplitudes and/or time-voltage areas comprises: receiving a ECG QRS data, a EMG data, a VCG data and/or a mathematically synthesized VCG data via the input/output interface or the memory; receiving a baseline ECG QRS data, a baseline EMG data and/or a baseline VCG data via the input/output interface or the memory; determining the one or more waveform amplitudes and/or time-voltage areas from the ECG QRS data, the EMG data and/or the VCG data using the one or more processors; and determining the one or more baseline waveform amplitudes and/or time-voltage areas from the baseline ECG QRS data, the baseline EMG data and/or the baseline VCG data using the one or more processors. In another aspect, the ECG QRS data, the EMG data and/or the VCG data is generated or recorded before or after the baseline ECG QRS data, the baseline EMG data and/or the baseline VCG data. In another aspect, the ECG QRS data, the EMG data and/or the VCG data is generated or recorded after the baseline ECG QRS data, the baseline EMG data and/or the baseline VCG data and determining the signal change. In another aspect, the method further comprises generating or recording the ECG QRS data, the EMG data and/or the VCG data and the baseline ECG QRS data, the baseline EMG data and/or the baseline VCG data using one or more sensors or devices. In another aspect, the one or more sensors or devices comprise a 12-lead ECG device, a continuous ECG telemetry monitor, a stress testing system, an extended monitoring device, a smartphone-enabled ECG medical device, an external cardioverter-defibrillator therapy device, a subcutaneous implantable cardioverter defibrillators (ICD), a pacemaker, an automated external defibrillators (AED), or an automatic implantable cardioverter defibrillator (AICD). In another aspect, the computing device is integrated into the one or more sensors or devices; or the one or more sensors or devices are integrated into the computing device. In another aspect, determining the signal change between the wide complex heart beat waveform amplitudes and/or time-voltage areas and the baseline heart beat waveform amplitudes and/or time-voltage areas comprises: receiving a wide complex heart beat waveform duration via the input/output interface or the memory; determining, using the one or more processors, a percent amplitude change (PAC) based on the wide complex heart beat waveform amplitudes and the baseline wide complex heart beat waveform amplitudes, and/or a percent time-voltage area change (PTVAC) based on the wide complex heart beat waveform time-voltage areas and the baseline wide complex heart beat waveform time-voltage areas; determining a classification probability based on the wide complex heart beat waveform duration, and the PAC and/or the PTVAC using the one or more processors; and wherein the signal change comprises the classification probability, and the classification probability comprises a VT probability, a SWCT probability, or a ventricular pacing probability. In another aspect, determining the classification probability is further determined based one or more additional classification predictors. In another aspect, the PAC comprises a frontal PAC and a horizontal PAC, and the PTVAC comprises a frontal PTVAC and a horizontal PTVAC.

In another aspect, determining the signal change between the wide complex heart beat waveform amplitudes and/or time-voltage areas and the baseline heart beat waveform amplitudes and/or time-voltage areas comprises: receiving a WCT QRS duration via the input/output interface or the memory; the one or more wide complex heart beat waveform amplitudes and/or time-voltage areas comprise one or more frontal plane WCT positive waveform amplitudes and/or time-voltage areas, one or more horizontal plane WCT positive waveform amplitudes and/or time-voltage areas, one or more frontal plane WCT negative waveform amplitudes and/or time-voltage areas, and one or more horizontal plane WCT negative waveform amplitudes and/or time-voltage areas; the one or more the baseline heart beat waveform amplitudes and/or time-voltage areas comprise one or more frontal plane baseline positive waveform amplitudes and/or time-voltage areas, one or more horizontal plane baseline positive waveform amplitudes and/or time-voltage areas, one or more frontal plane baseline negative waveform amplitudes and/or time-voltage areas, and one or more horizontal baseline negative waveform amplitudes and/or time-voltage areas; determining (1) a frontal percent amplitude change (PAC) based on the one or more frontal plane WCT positive waveform amplitudes, one or more frontal plane WCT negative waveform amplitudes, one or more frontal plane baseline positive waveform amplitudes, and one or more frontal plane baseline negative waveform amplitudes, and/or (2) a frontal percent time-voltage area (PTVAC) based on the one or more frontal plane WCT positive waveform time-voltage areas, one or more frontal plane WCT negative waveform time-voltage areas, one or more frontal plane baseline positive waveform time-voltage areas, and one or more frontal plane baseline negative waveform time-voltage areas; determining (1) a horizontal PAC based on the one or more horizontal plane WCT positive waveform amplitudes, one or more horizontal plane WCT negative waveform amplitudes, one or more horizontal plane baseline positive waveform amplitudes, and one or more horizontal baseline negative waveform amplitudes, and/or (2) a horizontal PTVAC based on the one or more horizontal plane WCT positive waveform time-voltage areas, one or more horizontal plane WCT negative waveform time-voltage areas, one or more horizontal plane baseline positive waveform time-voltage areas, and one or more horizontal baseline negative waveform time-voltage areas; determining a VT probability using a statistical or machine learning process based on the WCT QRS duration and (1) the frontal PAC and the horizontal PAC, and/or (2) the frontal PTVAC and the horizontal PTVAC; and wherein the signal change comprises the VT probability. In another aspect, the statistical or machine learning process comprises a linear regression algorithm, a logistic regression model, a linear discriminate analysis algorithm, a Naive Bayes algorithm, a computational model using artificial neural networks, a computational model based on classification or regression trees, a k-nearest neighbors based model, a support vector machine based model, a boosting algorithm, or an ensemble machine learning algorithm.

In another aspect, the frontal PAC is determined by $$\text{Frontal } PAC\ (\%) = \left(\frac{\text{Frontal } AAC}{\text{Frontal } BA}\right) \times 100,$$

where: Frontal $AAC=TAC_{aVR}+TAC_{aVL}+TAC_{aVF}$, Frontal $BA=TBA_{aVR}+TBA_{aVL}+TBA_{aVF}$, $TAC_{LeadX}=APC_{LeadX}+ANC_{LeadX}$, $TBA_{Baseline:LeadX}=(-)\text{Amplitude}_{Baseline:LeadX}+(+)\text{Amplitude}_{Baseline:LeadX}$, $APC_{LeadX}=|(+)\text{Amplitude}_{WCT:LeadX}-(+)\text{Amplitude}_{Baseline:LeadX}|$, $ANC_{LeadX}=|(-)\text{Amplitude}_{WCT:LeadX}-(-)\text{Amplitude}_{Baseline:LeadX}|$, LeadX denotes V1, V4, V6 (horizontal plane) or aVL, aVR, aVF (frontal plane); the horizontal PAC is determined by $$\text{Horizontal } PAC\ (\%) = \left(\frac{\text{Horizontal } AAC}{\text{Horizontal } BA}\right) \times 100,$$

where: Horizontal AAC=$TAC_{V1}+TAC_{V4}+TAC_{V6}$, Horizontal BA=$TBA_{V1}+TBA_{V4}+TBA_{V6}$; and the VT probability ($P_{VT}$) is determined by:

$$P_{VT} = \frac{e^{(a+b \times WCT_{duration}+c \times PAC_{frontal}+d \times PAC_{horizontal})}}{1+e^{(a+b \times WCT_{duration}+c \times PAC_{frontal}+d \times PAC_{horizontal})}},$$

where a, b, c and d are constants. In another aspect, the frontal PTVAC is determined by $$\text{Frontal } PTV\,AC\,(\%) = \left(\frac{\text{Frontal } ATV\,AC}{\text{Frontal } BTV\,A}\right) \times 100,$$

where: Frontal ATVAC=$TTVAC_{aVR}+TTVAC_{aVL}+TTVAC_{aVF}$, Frontal BTVA=$TBTVA_{aVR}+TBTVA_{aVL}+TBTVA_{aVF}$, $TTVAC_{LeadX}=TVAPC_{LeadX}+TVANC_{LeadX}$, $TBTVA_{Baseline:LeadX}=(-)$TimeVoltage Area$_{Baseline:LeadX}+(+)$TimeVoltage Area$_{Baseline:LeadX}$, $TVAPC_{LeadX}=|(+)$TimeVoltageArea$_{WCT:LeadX}-(+)$TimeVoltageArea$_{Baseline:LeadX}|$, $TVANC_{LeadX}=|(-)$TimeVoltageArea$_{WCT:LeadX}-(-)$TimeVoltageArea$_{Baseline:LeadX}|$, LeadX denotes V1, V4, V6 (horizontal plane) or aVL, aVR, aVF (frontal plane); the horizontal PTVAC is determined by $$\text{Horizontal } PTV\,AC\,(\%) = \left(\frac{\text{Horizontal } ATV\,AC}{\text{Horizontal } BTV\,A}\right) \times 100,$$

where:
Horizontal ATVAC=$TTVAC_{V1}+TTVAC_{V4}+TTVAC_{V6}$,
Horizontal BTVA=$TBTVA_{V1}+TBTVA_{V4}$ $TBTVA_{V6}$; and the VT probability ($P_{VT}$) is determined by:

$$P_{VT} = \frac{e^{(a+b \times WCT_{duration}+c \times PTV\,AC_{frontal}+d \times PTV\,AC_{horizontal})}}{1+e^{(a+b \times WCT_{duration}+c \times PTV\,AC_{frontal}+d \times PTV\,AC_{horizontal})}},$$

where: a, b, c and d are constants.

In another aspect, the input/output interface comprises a remote device, and the remote device is communicably coupled to the one or more processors via one or more networks. In another aspect, the method further comprises providing a recommendation to select or exclude a therapy, medication, diagnostic testing or referral for a patient based on the signal change. In another aspect, the computing device comprises a server computer, a workstation computer, a laptop computer, a mobile communications device, a personal data assistant, or a medical device. Moreover, the method can be implemented using a non-transitory computer readable medium that when executed causes the one or more processors to perform the method.

Another embodiment of the present invention provides an apparatus for classifying a wide complex heart beat(s) comprising an input/output interface, a memory, and one or more processors communicably coupled to the input/output interface and the memory. The one or more processors: receive one or more wide complex heart beat waveform amplitudes and/or time-voltage areas, and one or more baseline heart beat waveform amplitudes and/or time-voltage areas via the input/output interface or the memory, determine a signal change between the wide complex heart beat waveform amplitudes and/or time-voltage areas and the baseline heart beat waveform amplitudes and/or time-voltage areas using the one or more processors, and provide the signal change via the input/output interface, wherein the signal change provides an indication whether the wide complex heart beat(s) is from a ventricular source or a supraventricular aberrant condition.

In one aspect, the signal change further provides the indication whether the wide complex heart beat(s) is due to ventricular pacing. In another aspect, the wide complex heart beat(s) comprise a wide complex tachycardia (WCT), the ventricular source comprises a ventricular tachycardia (VT), and the supraventricular aberrant condition comprises a supraventricular wide complex tachycardia (SWCT). In another aspect, the one or more processors provide the signal change via the input/output interface by: automatically determining a wide complex heart beat classification for the wide complex heart beat(s) by comparing the signal change to a predetermined value, wherein the wide complex heart beat classification comprises the ventricular source or the supraventricular aberrant condition; and providing the wide complex heart beat classification via the input/output interface. In another aspect, the signal change comprises a VT probability, the wide complex heart beat classification comprises a VT whenever the VT probability is greater than or equal to the predetermined value, and the wide complex heart beat classification comprises a SWCT whenever the VT probability is less than the predetermined value. In another aspect, the one or more processors select the predetermined value from a range of 0% to 100%. In another aspect, the predetermined value comprises about 1%, 10%, 25%, 50%, 75%, 90% or 99%. In another aspect, the one or more processors provide the signal change by providing a "shock" signal, a "no shock" signal, or no signal. In another aspect, the wide complex heart beat waveform amplitudes and/or time-voltage areas and the baseline heart beat waveform amplitudes and/or time-voltage areas are obtained from an electrocardiogram (ECG) QRS signal, a ventricular electrogram (EMG) signal, and/or a vectorcardiogram (VCG) signal. In another aspect, the wide complex heart beat waveform amplitudes and/or time-voltage areas comprise a plurality of measured amplitudes and/or time-voltage areas of a ECG QRS waveform, a EMG waveform and/or a VCG waveform above and below an isoelectric baseline; and the baseline heart beat waveform amplitudes and/or time-voltage areas comprise a plurality of measured amplitudes and/or time-voltage areas of a baseline ECG QRS waveform, a baseline EMG waveform and/or a baseline VCG waveform above and below the isoelectric baseline.

In another aspect, the one or more processors receive the one or more wide complex heart beat waveform amplitudes and/or time-voltage areas, and one or more baseline heart beat waveform amplitudes and/or time-voltage areas by: receiving a ECG QRS data, a EMG data, a VCG data and/or a mathematically synthesized VCG data via the input/output interface or the memory; receiving a baseline ECG QRS data, a baseline EMG data and/or a baseline VCG data via the input/output interface or the memory; determining the one or more waveform amplitudes and/or time-voltage areas from the ECG QRS data, the EMG data and/or the VCG data; and determining the one or more baseline waveform amplitudes and/or time-voltage areas from the baseline ECG QRS data, the baseline EMG data and/or the baseline VCG data. In another aspect, the ECG QRS data, the EMG data and/or the VCG data is generated or recorded before or after the baseline ECG QRS data, the baseline EMG data and/or the baseline VCG data. In another aspect, the ECG QRS data, the EMG data and/or the VCG data is generated or recorded after the baseline ECG QRS data, the baseline EMG data and/or the baseline VCG data and determining the signal change. In another aspect, the ECG QRS data, the EMG data and/or the VCG data and the baseline ECG QRS data, the baseline EMG data and/or the baseline VCG data are generated or recorded using one or more sensors or devices. In another aspect, the one or more sensors or devices comprise a 12-lead ECG device, a continuous ECG telemetry monitor, a stress testing system, an extended monitoring device, a smartphone-enabled ECG medical device, a cardioverter-defibrillator therapy device, a subcutaneous implantable cardioverter defibrillators (ICD), a pacemaker, an automated external defibrillators (AED), or an automatic implantable cardioverter defibrillator (AICD). In another aspect, the input/output interface, the memory and the one or more processors are integrated into the one or more sensors or devices; or the one or more sensors or devices are integrated into a computing device comprising the input/output interface, the memory and the one or more processors. In another aspect, the one or more processors determine the signal change between the wide complex heart beat waveform amplitudes and/or time-voltage areas and the baseline heart beat waveform amplitudes and/or time-voltage areas by: receiving a wide complex heart beat waveform duration via the input/output interface or the memory; determining a percent amplitude change (PAC) based on the wide complex heart beat waveform amplitudes and the baseline wide complex heart beat waveform amplitudes, and/or a percent time-voltage area change (PTVAC) based on the wide complex heart beat waveform time-voltage areas and the baseline wide complex heart beat waveform time-voltage areas; determining a classification probability based on the wide complex heart beat waveform duration, the PAC and/or the PTVAC; and wherein the signal change comprises the classification probability, and the classification probability comprises a VT probability, a SWCT probability, or a ventricular pacing probability. In another aspect, determining the classification probability is further determined based one or more additional classification predictors. In another aspect, the PAC comprises a frontal PAC and a horizontal PAC, and the PTVAC comprises a frontal PTVAC and a horizontal PTVAC.

In another aspect, the one or more processors determine the signal change between the wide complex heart beat waveform amplitudes and/or time-voltage areas and the baseline heart beat waveform amplitudes and/or time-voltage areas by: receiving a WCT QRS duration via the input/output interface or the memory; the one or more wide complex heart beat waveform amplitudes and/or time-voltage areas comprise one or more frontal plane WCT positive waveform amplitudes and/or time-voltage areas, one or more horizontal plane WCT positive waveform amplitudes and/or time-voltage areas, one or more frontal plane WCT negative waveform amplitudes and/or time-voltage areas, and one or more horizontal plane WCT negative waveform amplitudes and/or time-voltage areas; the one or more the baseline heart beat waveform amplitudes and/or time-voltage areas comprise one or more frontal plane baseline positive waveform amplitudes and/or time-voltage areas, one or more horizontal plane baseline positive waveform amplitudes and/or time-voltage areas, one or more frontal plane baseline negative waveform amplitudes and/or time-voltage areas, and one or more horizontal baseline negative waveform amplitudes and/or time-voltage areas; determining (1) a frontal percent amplitude change (PAC) based on the one or more frontal plane WCT positive waveform amplitudes, one or more frontal plane WCT negative waveform amplitudes, one or more frontal plane baseline positive waveform amplitudes, and one or more frontal plane baseline negative waveform amplitudes, and/or (2) a frontal percent time-voltage area (PTVAC) based on the one or more frontal plane WCT positive waveform time-voltage areas, one or more frontal plane WCT negative waveform time-voltage areas, one or more frontal plane baseline positive waveform time-voltage areas, and one or more frontal plane baseline negative waveform time-voltage areas; determining (1) a horizontal PAC based on the one or more horizontal plane WCT positive waveform amplitudes, one or more horizontal plane WCT negative waveform amplitudes, one or more horizontal plane baseline positive waveform amplitudes, and one or more horizontal baseline negative waveform amplitudes, and/or (2) a horizontal PTVAC based on the one or more horizontal plane WCT positive waveform time-voltage areas, one or more horizontal plane WCT negative waveform time-voltage areas, one or more horizontal plane baseline positive waveform time-voltage areas, and one or more horizontal baseline negative waveform time-voltage areas; determining a VT probability using a statistical or machine learning process based on the WCT QRS duration and (1) the frontal PAC and the horizontal PAC, and/or (2) the frontal PTVAC and the horizontal PTVAC; and wherein the signal change comprises the VT probability. In another aspect, the statistical or machine learning process comprises a linear regression algorithm, a logistic regression model, a linear discriminate analysis algorithm, a Naive Bayes algorithm, a computational model using artificial neural networks, a computational model based on classification or regression trees, a k-nearest neighbors based model, a support vector machine based model, a boosting algorithm, or an ensemble machine learning algorithm.

In another aspect, the frontal PAC is determined by $$\text{Frontal } PAC\ (\%) = \left(\frac{\text{Frontal } AAC}{\text{Frontal } BA}\right) \times 100,$$

where: Frontal $AAC = TAC_{aVR} + TAC_{aVL} + TAC_{aVF}$, Frontal $BA = TBA_{aVR} + TBA_{aVL} + TBA_{aVF}$, $TAC_{LeadX} = APC_{LeadX} + ANC_{LeadX}$, $TBA_{Baseline:LeadX} = (-)\text{Amplitude}_{Baseline:LeadX} + (+)\text{Amplitude}_{Baseline:LeadX}$, $APC_{LeadX} = |(+)\text{Amplitude}_{WCT:LeadX} - (+)\text{Amplitude}_{Baseline:LeadX}|$, $ANC_{LeadX} = |(-)\text{Amplitude}_{WCT:LeadX} - (-)\text{Amplitude}_{Baseline:LeadX}|$, LeadX denotes V1, V4, V6 (horizontal plane) or aVL, aVR, aVF (frontal plane); the horizontal PAC is determined by $$\text{Horizontal } PAC\ (\%) = \left(\frac{\text{Horizontal } AAC}{\text{Horizontal } BA}\right) \times 100,$$

where: Horizontal $AAC = TAC_{V1} + TAC_{V4} + TAC_{V6}$, Horizontal $BA = TBA_{V1} + TBA_{V4} + TBA_{V6}$; and the VT probability ($P_{VT}$) is determined by:

$$P_{VT} = \frac{e^{(a + b \times WCT_{duration} + c \times PAC_{frontal} + d \times PAC_{horizontal})}}{1 + e^{(a + b \times WCT_{duration} + c \times PAC_{frontal} + d \times PAC_{horizontal})}},$$

where a, b, c and d are constants. In another aspect, the frontal PTVAC is determined by $$\text{Frontal } PTVAC(\%) = \left(\frac{\text{Frontal } ATVAC}{\text{Frontal } BTVA}\right) \times 100,$$

where: Frontal ATVAC=TTVAC$_{aVR}$+TTVAC$_{aVL}$+TTVAC$_{aVF}$, Frontal BTVA=TBTVA$_{aVR}$+TBTVA$_{aVL}$+TBTVA$_{aVF}$, TTVAC$_{LeadX}$=TVAPC$_{LeadX}$+TVANC$_{LeadX}$, TBTVA$_{Baseline:LeadX}$=(−)TimeVoltage Area$_{Baseline:LeadX}$+(+)TimeVoltage Area$_{Baseline:LeadX}$, TVAPC$_{LeadX}$=|(+)TimeVoltageArea$_{WCT:LeadX}$−(+) TimeVoltageArea$_{Baseline:LeadX}$|, TVANC$_{LeadX}$=|(−)TimeVoltageArea$_{WCT:LeadX}$−(−) TimeVoltageArea$_{Baseline:LeadX}$|, LeadX denotes V1, V4, V6 (horizontal plane) or aVL, aVR, aVF (frontal plane); the horizontal PTVAC is determined by $$\text{Horizontal } PTVAC(\%) = \left(\frac{\text{Horizontal } ATVAC}{\text{Horizontal } BTVA}\right) \times 100,$$

where: Horizontal ATVAC=TTVAC$_{V1}$+TTVAC$_{V4}$+TTVAC$_{V6}$,
Horizontal BTVA=TBTVA$_{V1}$+TBTVA$_{V4}$+TBTVA$_{V6}$; and the VT probability (P$_{VT}$) is determined by:

$$P_{VT} = \frac{e^{(a+b \times WCT_{duration} + c \times PTVAC_{frontal} + d \times PTVAC_{horizontal})}}{1 + e^{(a+b \times WCT_{duration} + c \times PTVAC_{frontal} + d \times PTVAC_{horizontal})}},$$

where: a, b, c and d are constants.

In another aspect, the input/output interface comprises a remote device, and the remote device is communicably coupled to the one or more processors via one or more networks. In another aspect, the one or more processors provide a recommendation to select or exclude a therapy, medication, diagnostic testing or referral for a patient based on the signal change. In another aspect, apparatus comprises a server computer, a workstation computer, a laptop computer, a mobile communications device, a personal data assistant, or a medical device.

BRIEF DESCRIPTION OF THE DRAWINGS

For a more complete understanding of the features and advantages of the present invention, reference is now made to the detailed description of the invention along with the accompanying figures and in which:

FIGS. 6A-6C depict the structure of the frontal PAC formula, horizontal PAC formula and amplitude based WCT formula in accordance with one embodiment of the present invention;

FIG. 9 is Table 1 showing the ECG characteristics of the derivation cohort;

FIG. 10 is Table 2 showing the clinical characteristics of the derivation cohort;

FIG. 11 is Table 3 showing the mean and standard deviation (SD) of measured and calculated ECG variables among VT or SWCT groups within the derivation cohort;

FIG. 12D is a table showing electrocardiographic variables among baseline ECG sub-groups in accordance with on embodiment of the present invention;

FIG. 14 is Table 4 showing the ECG characteristics of the validation cohort;

FIG. 15 is Table 5 showing the clinical characteristics of the validation cohort;

FIGS. 16A and 16B are histograms demonstrating the distribution of clinically diagnosed VT and SWCT according to the amplitude based WCT Formula diagnostic performance at on probability estimates (0.000%-99.999%) for the validation cohort;

FIG. 17 is Table 6 showing the diagnostic performance of various VT probability partitions for the validation cohort in accordance with one embodiment of the present invention;

FIGS. 19A and 19B are tables showing the electrocardiographic characteristics of clinical SWCT classified as VT and clinical VT classified as SWCT by the amplitude based WCT Formula's 50% VT probability partition for the validation cohort;

FIGS. 23A-23C depict derivations of the frontal PTVAC formula, horizontal PTVAC formula and time-voltage area based WCT formula in accordance with one embodiment of the present invention;

DETAILED DESCRIPTION OF THE INVENTION

Figure 1A:
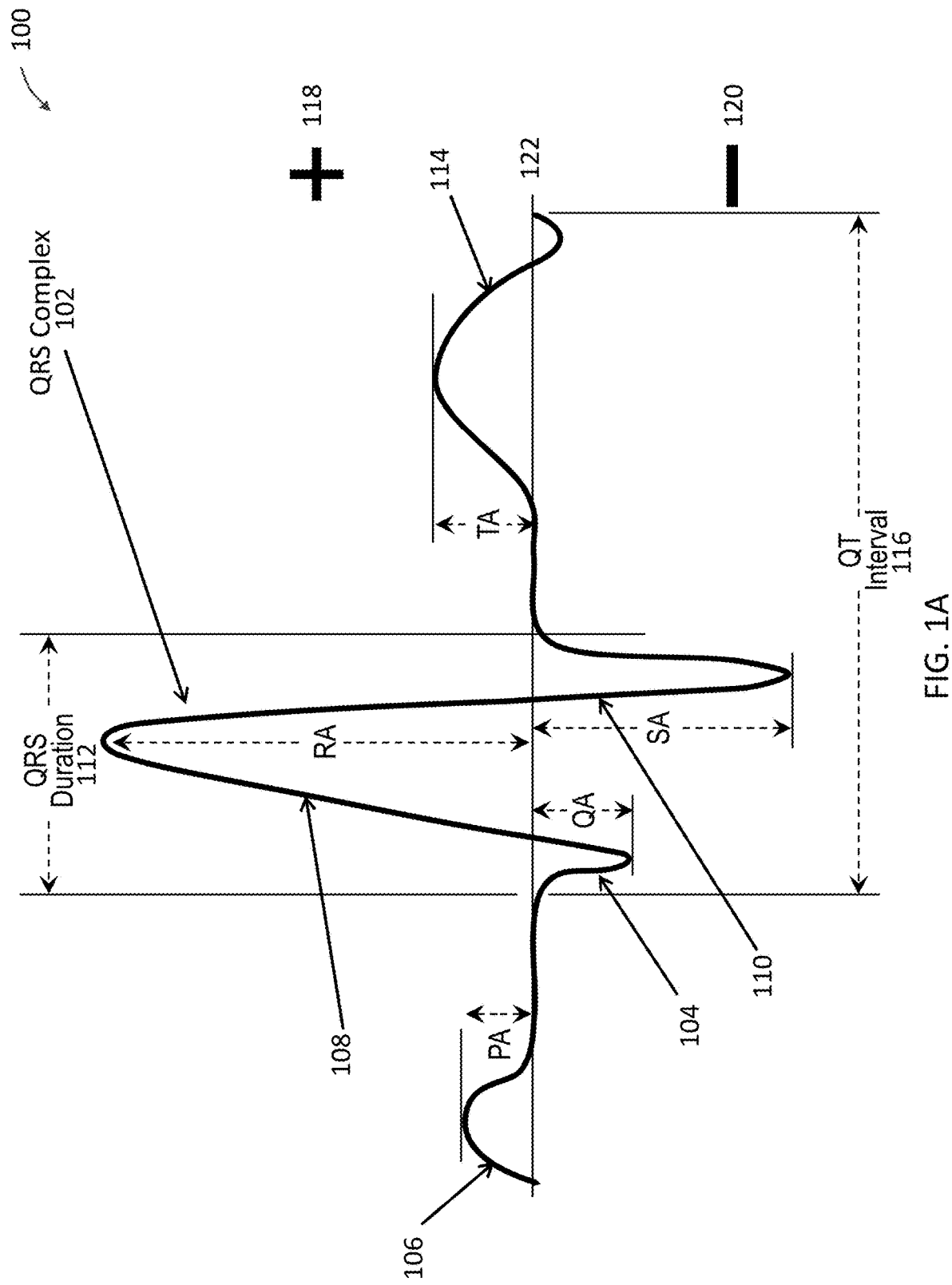
FIG. 1A depicts a schematic representation of a normal ECG.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention provides a new electrophysiological principle (degree of QRS or ventricular electrogram signal change in amplitude and/or time-voltage area between the wide complex tachycardia (WCT) and baseline heart rhythm helps distinguish ventricular tachycardia (VT) and supraventricular wide complex tachycardia (SWCT)) that can be exploited by ECG interpretation software to render precise and accurate predictions of VT verses SWCT. The WCT differentiation method described herein can be automatically implemented by contemporary ECG interpretation software. Note that other medical devices that analyze ECG signals, electrogram (EMG) signals, and/or vectorcardiogram (VCG) signals from the heart (e.g pacemakers, transvenous lead or subcutaneous, automated implantable cardioverter-defibrillators, automated external defibrillators) can utilize the similar methods or systems based on the foregoing principles of this present invention. Note that other formulas or algorithms based on the foregoing principle and other information described herein can be used to predict VT by diagnostic ECG interpretation software. As a result, the present invention is not limited to the WCT Formulas described herein.

The WCT Formulas were designed to effectively, accurately and automatically differentiate WCT into VT, which is usually a dangerous heart rhythm, and SWCT, which is generally a less hazardous heart rhythm. VT and SWCT are most often non-invasively diagnosed using a 12-lead ECG. However, the present invention is applicable to any current or future technology that provides the relevant data using known or unknown detection devices or sensors (i.e., any device that generates and analyzes ECG signals, ventricular EMG signals, and/or VCG signals).

The WCT Formulas are logistic regression models that deliver an automatic prediction VT likelihood (i.e., % VT probability) using ECG measurements (e.g. WCT duration) and calculations (e.g., frontal and horizontal Percent Amplitude Change (PAC), or frontal and horizontal Percent Time-Voltage Area Change (PTVAC)) derived from paired WCT and baseline ECGs. The frontal and horizontal PAC and PTVAC formulas are highly predictive determinants of VT and SWCT, wherein a low PAC (%) or PTVAC (%) indicates SWCT and a high PAC (%) or PTVAC (%) indicates VT. Moreover, the frontal and horizontal PAC or PTVAC calculations are independent predictors of VT. Each calculation is able to provide a reliable means to effectively distinguish VT and SWCT. They can also be used to differentiate discrete ventricular depolarizations due to premature ventricular contractions, ventricular pacing, and supraventricular aberrant conduction.

The WCT Formula using amplitudes will be described in detail below. The WCT Formula using time-voltage areas will be described thereafter.

Now referring to FIGS. 1A and 1B, the 12-lead ECG and resulting data used in the WCT Formula will be described. The ECG currently is the most commonly used test to determine whether a patient's underlying heart rhythm is normal or abnormal. The 12-lead ECG records the electrical activity of the heart using 12 separate leads. Each lead records unique QRS complexes representative of the heart's ventricular depolarization. FIG. 1A is a schematic representation of a stereotypical ECG pattern for a single heart beat 100. The QRS complex waveform 102 is the combination of three graphical deflections: (1) the Q wave 104 having a downward deflection immediately following the P wave 106; (2) the R wave 108 having an upward deflection immediately following the Q wave 104; and (3) the S wave 110 having a downward deflection following the R wave 108. The Q wave 104, R wave 108 and S wave 110 occur in rapid succession and are encompassed within the QRS complex waveform 102 and accompanying time interval, QRS duration 112. The T-wave 114 follows the S wave 110. Each wave has amplitude denoted as PA, QA, RA, SA and TA. In addition, the QT interval 116 is the time interval extending from the onset of the QRS complex waveform 102 to the end of the T wave 114. The QRS complex 102 is divided into positive (+) amplitudes 118 and negative (−) amplitudes 120. The positive (+) amplitudes 118 are the vertical QRS complex deflections above the isoelectric baseline 122, namely the amplitude of r/R wave and r'/R' wave. The negative (−) amplitudes 120 are the vertical QRS complex deflections below the isoelectric baseline 122, namely the amplitude of q or QS wave, s/S wave and s'/S' wave. In addition computerized ECG interpretation software, such as the MUSE provided by GE Healthcare, automatically measures QRS complex waveform 102 attributes, namely q or QS, r/R, s/S, r'/R', s'/S' durations (ms), amplitudes (µV), and time-voltage areas (µV·ms) Note that standard annotation of QRS complex waveforms of small QRS waveforms are in lower case and large QRS waveforms are in upper case.

Figure 1B:
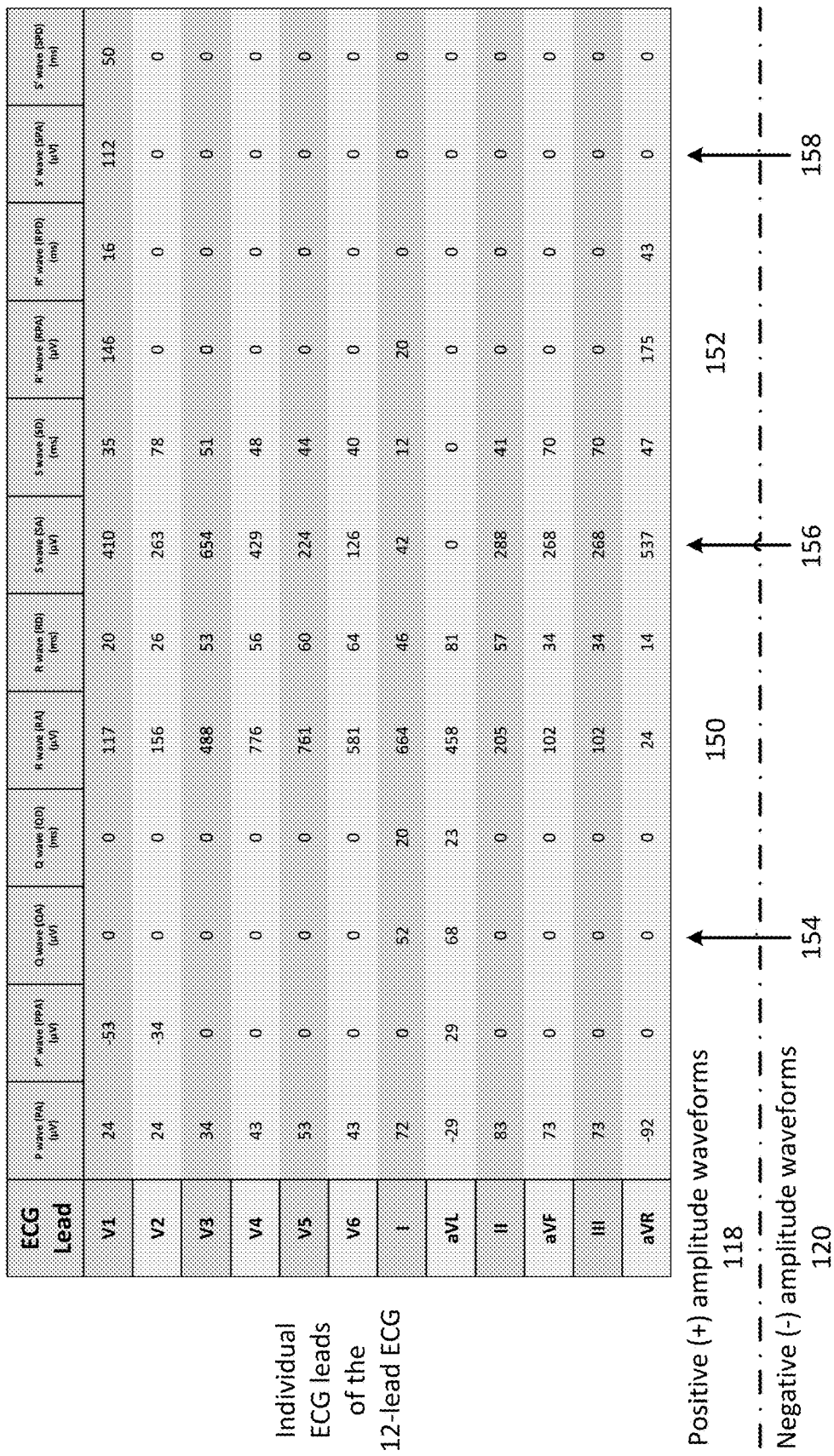
FIG. 1B depicts an example of ECG data collected and recorded from a patient's 12-lead ECG.

FIG. 1B depicts a measurement matrix showing an example of 12-lead ECG data recorded and calculated by computerized ECG interpretation software. The 12 leads are denoted as V1, V2, V3, V4, V5, V6, I, aVL, II, aVF, III, and aVR. In this example, QRS waveform deflection (q or QS, r/R, s/S, r'/R', s'/S') measurements including duration (ms) and amplitude (µV) are provided by GE Healthcare's MUSE ECG interpretation software and databank. In this example, the amplitude (_A) and duration (_D) data for the various waves are denoted as PA, PPA, QA, QD, RA, RD, SA, SD, RPA, RPD, SPA, and SPD. Note that other computerized ECG interpretation software can be used to derive this electrocardiographic data. Note that these measurements are not routinely shown on the ECG paper recording, but are available within the ECG interpretation software databanks. The positive (+) amplitudes 118 are the vertical QRS complex deflections above the isoelectric baseline 122, namely the r/R wave amplitude (µV) 150 and r'/R' wave amplitude (µV) 152. The negative (−) amplitudes 120 are the vertical QRS complex deflections below the isoelectric baseline 122, namely the q or QS wave amplitude (µV) 154, s/S wave amplitude (µV) 156, and s'/S' wave amplitude (µV) 158. As will be described in more detail below, the voltage amplitude measurements from specific leads (frontal ECG plane: aVL, aVF, aVR; and horizontal ECG plane: V1, V4, V6) are used in the frontal and horizontal PAC formulas to generate the frontal and horizontal PACs (%).

Note that contemporary computerized ECG interpretation software also routinely provides standard ECG measurements including QRS duration (ms), QTc duration (ms), and frontal plane R and T wave axes (°). These measurements are typically apparent/reported on the 12-lead ECG paper recording. The difference in QRS duration (ms), frontal plane R wave axis (°) and frontal plane T wave axis (°) between the WCT and baseline ECGs may be automatically calculated by computerized ECG interpretation software. Note that time-voltage area measurements of separate QRS waveform deflections (q or QS, r/R, s/S, r'/R', s'/S') can be automatically provided by computerized ECG interpretation software and electronic databanks (e.g., MUSE from GE Healthcare, etc.).

The new electrophysiology principles that are the backbone of the horizontal and frontal PAC formulas will now be described. The number of ways VT may propagate within and depolarize the ventricular myocardium is ostensibly limitless. Consequently, VTs have an immeasurable number of ways they can be electrocardiographically distinct from their respective baseline ECG. In contrast, the manner SWCTs depolarize the ventricular myocardium is ordinarily confined to the same His-Purkinje network or implantable device system utilized by the baseline heart rhythm; in rarer instances SWCTs may be due to ventricular pre-excitation using separate atrioventricular accessory pathways. As a result, many SWCTs, especially those with pre-existing aberrancy or ventricular pacing, demonstrate substantial electrocardiographic similarity with the baseline ECG. On the contrary, SWCTs with "functional" aberration exhibit recognizably different QRS complex configurations. However, since most functional SWCTs demonstrate antegrade impulse propagation and ventricular depolarization confined in the His-Purkinje network, they are destined to express a relatively constrained variety of electrocardiographically distinct QRS complexes.

Moreover, the amplitude and time-voltage area based WCT Formulas (and its principles) can be similarly applied to these types of defibrillator devices because they either use ECG signals using surface ECG electrodes (or a modification thereof with the subcutaneous ICD) or EMG signals derived from intracardiac and extracardiac electrodes (in the case of AICDs and pacemakers) to help distinguish different heart rhythms. Because these devices acquire ventricular depolarization signals from surface ECG electrodes or EMG electrodes, the invention, and its principles of QRS (or ventricular EMG signal) amplitude (or time-voltage area) change, can be applied to help them more accurately discriminate SWCT and VT.

Since the means by which VT may propagate within and depolarize the ventricular myocardium is essentially unlimited, VTs have an expansive means to which their ventricular electrograms (EMGs) may be morphologically distinct from the ventricular EMGs of the baseline heart rhythm. In contrast, the manner SWCTs depolarize the ventricular myocardium is ordinarily confined to the same His-Purkinje network or implantable device system utilized by the baseline heart rhythm; in rarer instances SWCTs may be to ventricular pre-excitation using separate atrioventricular accessory pathways. As a result, many ventricular EMGs from SWCTs, especially those with pre-existing aberrancy or ventricular pacing, demonstrate marked similarity with the ventricular EMGs for the patient's baseline heart rhythm. On the contrary, SWCTs with "functional" aberration exhibit recognizably different ventricular EMG configurations. However, since functional SWCTs still demonstrate antegrade impulse propagation and ventricular depolarization confined in the His-Purkinje network, they tend to express a relatively constrained variety of ventricular EMG complexes.

As a result, various embodiments of the present invention can be used to further help guide therapy decisions (e.g., "shock patient" for VT OR "do not shock the patient" for SWCT). As a consequence, the likelihood of appropriate device defibrillations (i.e., shocks) may be increased while decreasing the likelihood of inappropriate device defibrillations.

Likewise, various embodiments of the present invention can be used by conventional, transvenous lead based devices like AICDs or pacemakers. These devices analyze multiple separate bipolar EMG signals derived from various intracardiac and extracardiac electrodes combinations (e.g., right ventricular coil to AICD generator housing OR extracardiac SVC coils to AICD generator housing OR RV right ventricular tip to right ventricular coil OR any other combination). In general, commercially available implanted devices usually store 2-4 EMG channels which are analyzed by embedded interpretation algorithms. These EMG channels (separately or in combination) can be examined to establish the degree (or percentage) of ventricular EMG amplitude or time-voltage area change between the WCT and baseline EMG. This procedure/method can help distinguish VT and SWCT.

Figure 2:
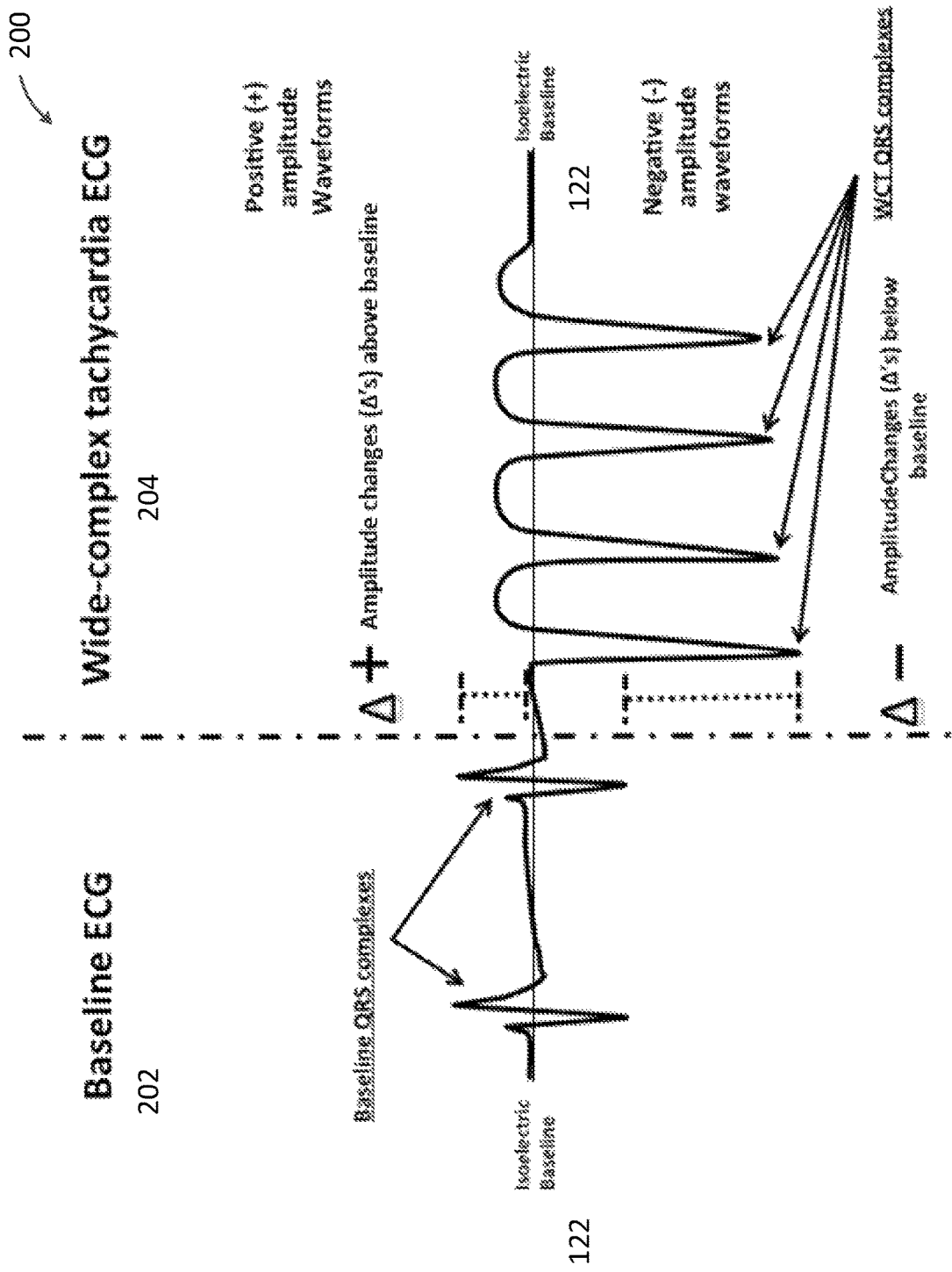
FIG. 2 depicts a schematic representation of the resultant QRS amplitude changes that manifest between a patient's baseline and WCT ECG.
Figures 3A, 3B, 3C, 3D, 3E:
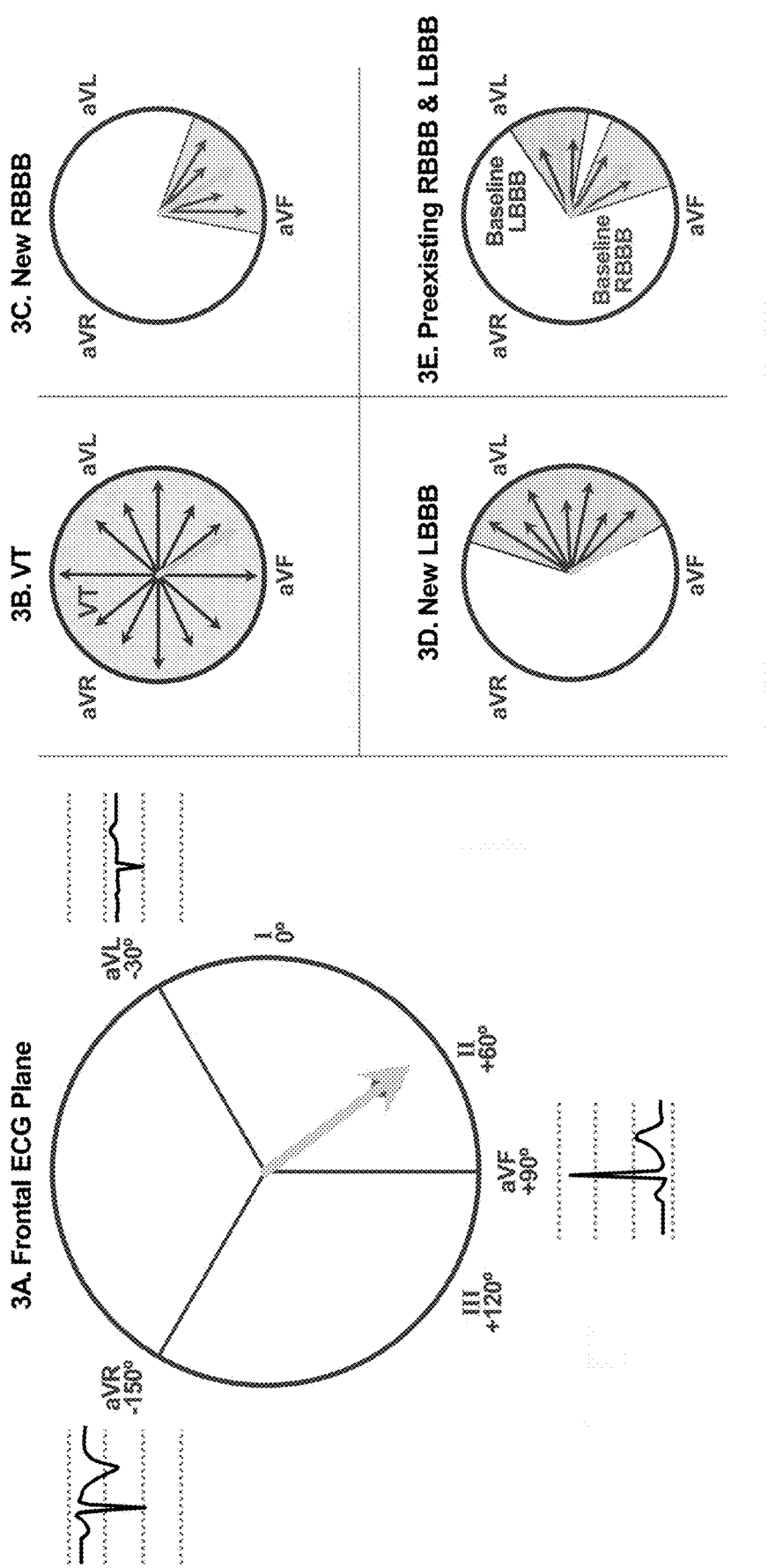
FIGS. 3A-3E depicts panels that summarize the expected range of mean electrical vector changes in the frontal ECG plane after WCT event onset.
Figures 4A, 4B, 4C, 4D, 4E:
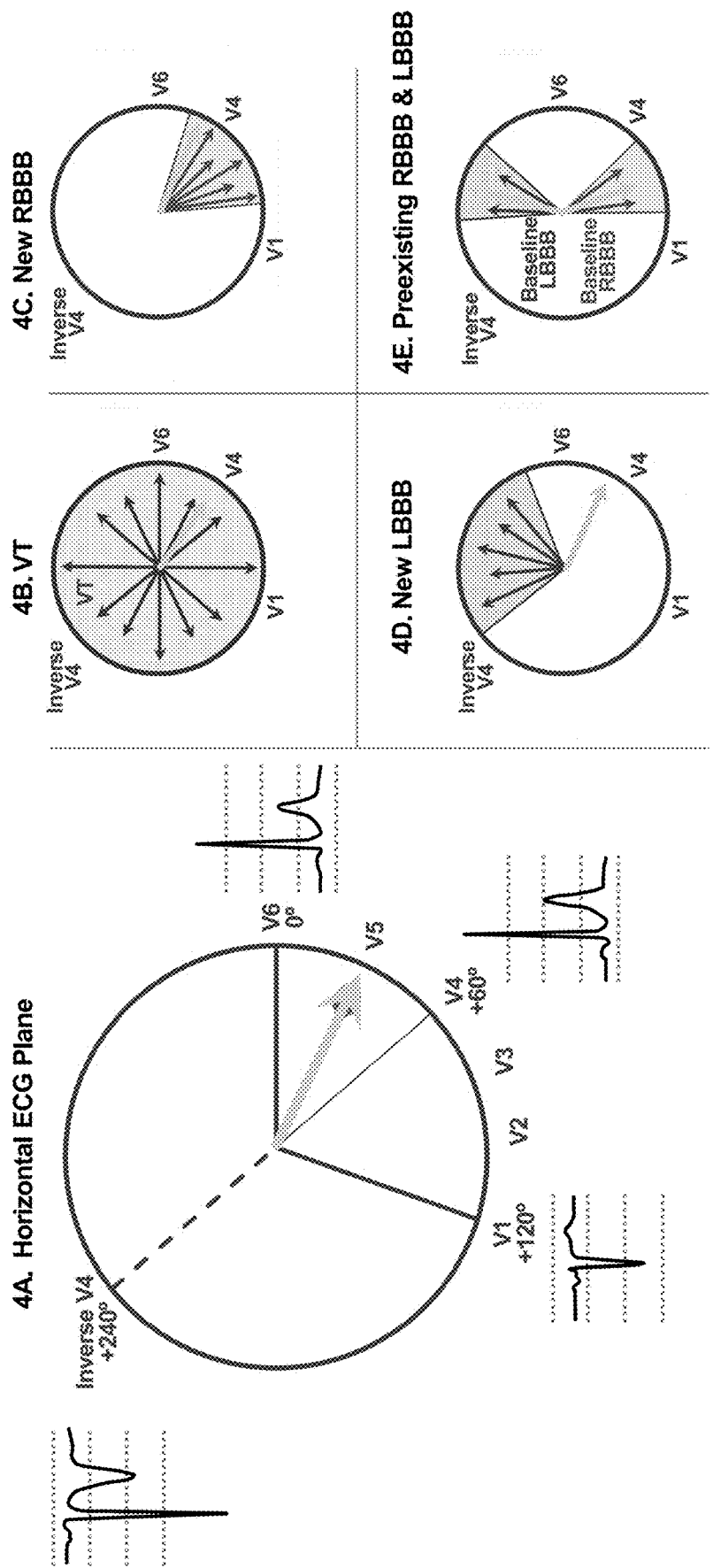
FIGS. 4A-4E depicts panels that summarize the expected range of mean electrical vector changes in the horizontal ECG plane after WCT event onset.

Referring now to FIG. 2, a schematic representation 200 of the resultant QRS amplitude changes that manifest between a patient's baseline ECG 202 and WCT ECG 204 is shown. The transition between a patient's baseline and WCT ECG (or vice versa) is inherently associated with changes (large or small) in QRS amplitude. Note the separate QRS amplitude changes (Δ's) that occur (+) above and (−) below the isoelectric baseline 122. Any change in QRS amplitude essentially signals attendant changes in the mean electrical vector of ventricular depolarization. Given VT's more expansive means of ventricular depolarization, it was hypothesized that it would typically demonstrate greater changes to the mean electrical vector than SWCT in both the frontal and horizontal ECG planes (FIGS. 3A-3E and 4A-4E, respectively). To test this hypothesis, the frontal and horizontal PAC formulas were created to broadly delineate the extent of QRS amplitude change that manifests between the WCT and baseline ECG.

Both calculations determine the percent (%) change in QRS amplitude that occurs at specific ECG lead combinations within the frontal (aVR, aVL, aVF) or horizontal (V1, V4, V6) ECG plane. In order to detect and quantify changes in the net direction (i.e. axis) and/or voltage intensity of the mean electrical vector, each PAC calculation utilizes ECG leads that are in effect separated by approximately 120°. In the case of V4, its mathematical inverse equivalent, "inverse V4," is separated equidistant from V1 and V6 by approximately 120°.

Now referring to FIGS. 3A-3E and 4A-4E, panels that summarize mean electrical vector changes in the frontal (FIGS. 3A-3E) and horizontal (FIGS. 4A-4E) ECG planes after WCT event onset are shown. The mean electrical vector (of the frontal or horizontal ECG plane) represents the summative electrical vector of ventricular depolarization. This value is determined from the QRS amplitudes derived from the 12-lead ECG. Heavy arrows represent the mean electrical vector for an ECG with demonstrating normal sinus rhythm (Panels 3A-3D, 4A-4D) or pre-existing BBB (Panels 3E, 4E). Shaded regions depict the range of potential axes and voltage intensities for mean electrical vectors that occur after WCT onset. Select ECG leads utilized by the frontal (aVR, aVL, aVF) and horizontal (V1, V4, V6) PAC formulas are highlighted. Inverse V4 is the inverted equivalent of its planar opposite: lead V4. Panels 3A, 4A demonstrates the mean electrical vector for a typical normal sinus baseline ECG. Panels 3B-3E, 4B-4E demonstrate the expected range of mean electrical vectors following the onset of various WCTs. Panels 3B, 4B demonstrates VT's incredibly expansive range of potential mean electrical vectors. Panels 3C-3D, 4C-4D demonstrate the relatively constrained mean electrical vector changes for SWCTs due to functional RBBB (Panels 3C, 4C) and LBBB (Panels 3D, 4D). Panels 3E, 4E depict the minimal mean electrical vector changes for SWCTs with pre-existing aberrancy. As shown, SWCTs have "restricted" changes to the mean electrical vector that translates into smaller frontal and horizontal PACs, and VTs tend to demonstrate "expansive" changes in the mean electrical vector that translates into larger frontal and horizontal PACs. Therefore, VT demonstrates much greater frontal and horizontal PACs than SWCT. Correspondingly, the larger frontal and horizontal PACs strongly predict VT, whereas smaller frontal and horizontal PACs predicted SWCT.

Figure 5A:
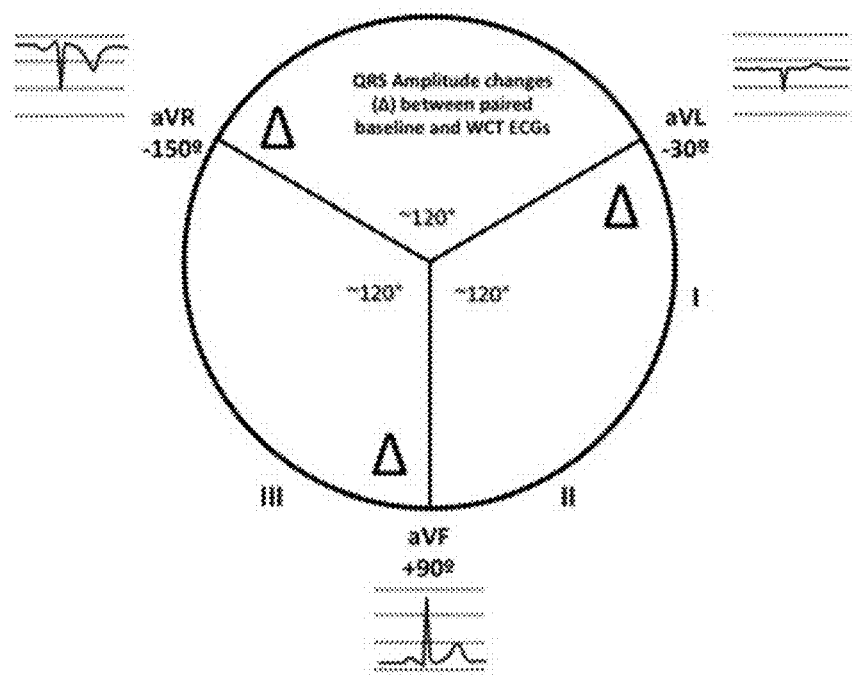
FIGS. 5A-5B are graphic depictions of select ECG lead combinations utilized by the frontal (aVR, aVL, aVF) and horizontal (V1, inverse V4, V6) PAC formulas in accordance with one embodiment of the present invention.
Figure 5B:
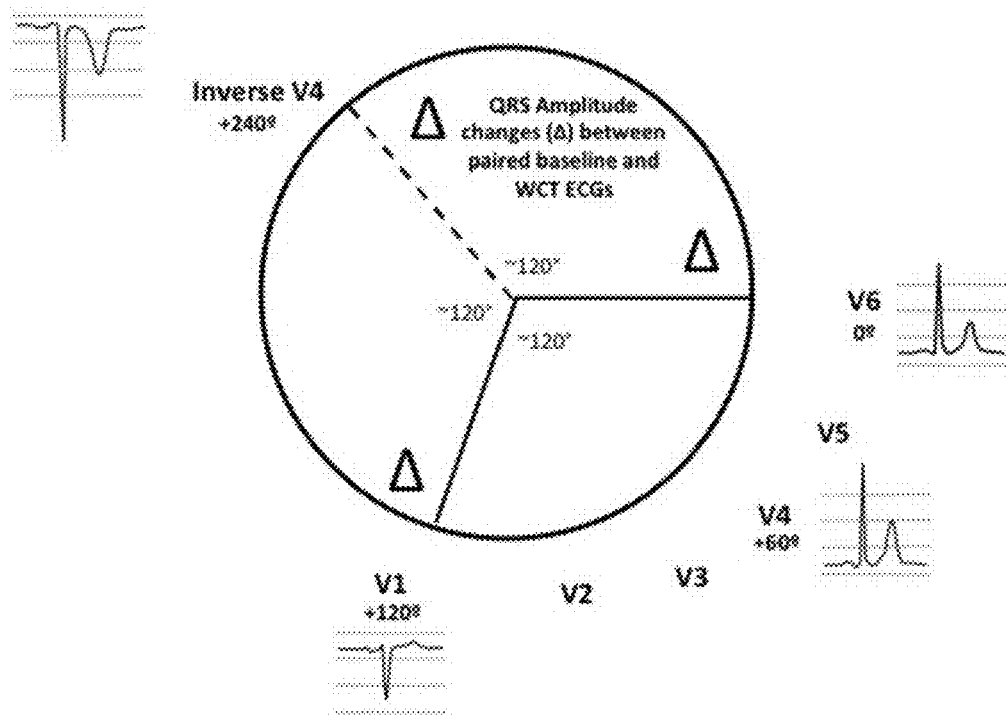

Referring now to FIGS. 5A-5B, graphic depictions of select ECG lead combinations utilized by the frontal (aVR, aVL, aVF) (FIG. 5A) and horizontal (V1, inverse V4, V6) (FIG. 5B) PAC formulas in accordance with one embodiment of the present invention are shown. The QRS amplitude change (Δ) that manifests between the baseline and WCT ECGs at these selected leads is the foundation for each PAC calculation. Note that the absolute QRS amplitude changes (Δ's) that manifest in lead V4 are mathematically equivalent to its planar opposite: inverse V4.

This present invention is in agreement with the multivariate logistic regression analysis reported by Griffith et al in 1991 (7). In their study, WCTs demonstrating large frontal plane QRS axis shifts (>=40°) from the baseline sinus rhythm ECG strongly predicted VT. Notably, they found QRS axis shifts to be the $3^{rd}$ strongest independent WCT predictor (after MI history and lead aVF QRS configuration) among 15 clinical and 11 electrocardiographic variables. Similar to the recognition of large frontal plane QRS axis shifts, each PAC calculation is able to detect sizable changes in the net direction (i.e. axis) of the mean electrical vector. Yet, more importantly, both PAC calculations provide a workable means to quantify changes in the net direction, voltage intensity, and/or QRS morphologic configuration produced by ventricular depolarization.

This present invention also indirectly agrees with the findings reported by Dongas et al in 1985 (16). Their study confirmed that WCTs with similar morphologic configurations as the pre-existing BBB were likely SWCTs, whereas WCTs with different morphologic configurations were likely VTs. Correspondingly, it was observed that SWCT demonstrated much smaller frontal and horizontal PACs than VT among ECG pairs with baseline QRS prolongation (QRS duration=>120 ms). However, it was furthermore observed that SWCT demonstrates smaller frontal and horizontal PACs than VT among ECG pairs without baseline QRS prolongation (QRS duration<120 ms) (see FIG. 12D).

It is well known that WCTs with more prolonged QRS durations are less likely due to SWCTs with aberrant conduction. This observation was first described in 1978 by Wellens et al who showed that VTs generally demonstrate longer QRS durations than SWCTs with functional aberrancy (3). This understanding later evolved into proposed QRS duration cut-offs for VT diagnoses: QRS>140 ms for WCTs with right BBB configuration and QRS>160 ms for WCTs with left BBB configuration (4). However, subsequent study (17-20) has found the sole use of QRS duration cut-offs to be problematic because SWCTs often demonstrate QRS durations greater than 160 ms. This most commonly occurs among patients with ongoing AAD use, pre-existing BBB or advanced cardiomyopathy. In addition, several series have also shown that VTs often demonstrate QRS durations less than 140 ms (3, 4, 18, 19). This tends to occur among VTs that rapidly utilize the His-Purkinje network or develop in patients without structural heart disease. The findings described herein support that VTs demonstrate longer QRS durations than SWCTs (see e.g., FIG. 11).

A logistic regression formula (i.e. WCT Formula) capable of accurate VT probability predictions using measurements and calculation provided by contemporary ECG interpretation software was created. Note that the present invention is not limited to use of a logistic regression model, such as the amplitude based WCT Formula. Other "machine learning" or artificial intelligence prediction methods (e.g., artificial neural networks, support vector machines, Random Forests, etc.) can be used with the frontal and horizontal PAC formulas. The amplitude based WCT Formula incorporates the strong independent WCT predictors including (1) WCT QRS duration (ms), (2) frontal PAC (%) and (3) horizontal PAC (%). The predictive contribution of each WCT predictor is concomitantly "weighed" according to their influence on the binary outcome (VT vs. SWCT) to render a precise VT probability estimation. Given each WCT predictor's direct relationship with VT likelihood, the amplitude based WCT Formula estimates higher VT probabilities for ECG pairs demonstrating greater WCT QRS durations, frontal PAC and/or horizontal PAC. Similarly, the amplitude based WCT Formula estimates lower VT probability for ECG pairs with smaller WCT QRS durations, frontal PAC and/or horizontal PAC.

The use of a multivariate logistic regression model to formulate the WCT Formulas allows (1) delivery of precise VT probability predictions and (2) later inclusion of other well-established, enhanced and/or newly formulated WCT predictors. Step-wise decision-tree approaches to diagnosis were avoided because of their tendency to prematurely commit to WCT diagnoses without considering the predictive strengths of other relevant predictors. The use of specific value cut-offs for VT diagnoses (e.g., QRS duration=>160 ms or frontal PAC>=75%) was avoided because this tends to cause (1) misclassifications due to VT and SWCT overlap and (2) ambiguity concerning the strength of WCT diagnoses for values distributed well above, well below, or at the margin of the designated cut-offs.

The WCT Formula's logistic regression model structure uses select independent WCT predictors (WCT QRS duration (ms), frontal PAC (%) and horizontal PAC (%)) to render a precise prediction of VT probability (%). Each WCT predictor ($X_x$) was assigned beta coefficients ($\beta_x$) according to their influence on the binary outcome (VT vs. non-VT). The "constant" term ($B_0$) represents the y-intercept of the least squares regression line. Discrete measured or calculated WCT predictor values derived from paired baseline and WCT ECGs are incorporated into the amplitude based WCT Formula to calculate VT probability ($P_{VT}$).

A calculation series is used to quantify the degree of QRS amplitude change that manifests between the baseline ECG and WCT event by converting raw ECG measurements into the frontal and horizontal PAC. The measured amplitudes (µV) of QRS waveforms above (+) (r/R and r'/R') and below (−) (q/QS, s/S, and s'/S') the isoelectric baseline from select frontal (aVR, aVL, aVF) and horizontal (V1, V4, V6) ECG leads were used to derive each calculation. Calculations were computed using JMP Pro 10 statistical software. Baseline Amplitude (BA), Absolute Amplitude Change (AAC) and Percent Amplitude Change (PAC) were calculated for both the frontal and horizontal ECG planes.

$APC_{LeadX} = |(+)\text{Amplitude}_{WCT:LeadX} - (+)\text{Amplitude}_{Baseline:LeadX}|$ $ANC_{LeadX} = |(-)\text{Amplitude}_{WCT:LeadX} - (-)\text{Amplitude}_{Baseline:LeadX}|$ $TAC_{LeadX} = APC_{LeadX} + ANC_{LeadX}$ $TBA_{Baseline:LeadX} = (-)\text{Amplitude}_{Baseline:LeadX} + (+)\text{Amplitude}_{Baseline:LeadX}$ where: LeadX denotes V1, V4, V6 (horizontal plane) or aVL, aVR, aVF (frontal plane). Note that (−) Amplitude=q/QS+s/S+s'/S' and (+) Amplitude=r/R+r'/R'. Note that ANC and APC equations have the "absolute" mathematical annotation (e.g. |equation's contents|).

Absolute Amplitude Change (AAC) represents the absolute summative difference in QRS amplitude between the WCT and baseline ECG.

Frontal AAC=$TAC_{aVR}+TAC_{aVL}+TAC_{aVF}$

Horizontal AAC=$TAC_{V1}+TAC_{V4}+TAC_{V6}$

Baseline Amplitude (BA) represents the total sum amplitude of (+) and (−) QRS waveforms in the baseline ECG.

Frontal BA=$TBA_{aVR}+TBA_{aVL}+TBA_{aVF}$

Horizontal BA=$TBA_{V1}+TBA_{V4}+TBA_{V6}$

Percent Amplitude Change (PAC) represents the percent change in QRS amplitude between the WCT and baseline ECG.

$$\text{Frontal } PAC(\%) = \left(\frac{\text{Frontal } AAC}{\text{Frontal } BA}\right) \times 100$$

$$\text{Horizontal } PAC(\%) = \left(\frac{\text{Horizontal } AAC}{\text{Horizontal } BA}\right) \times 100$$

Figure 6A:
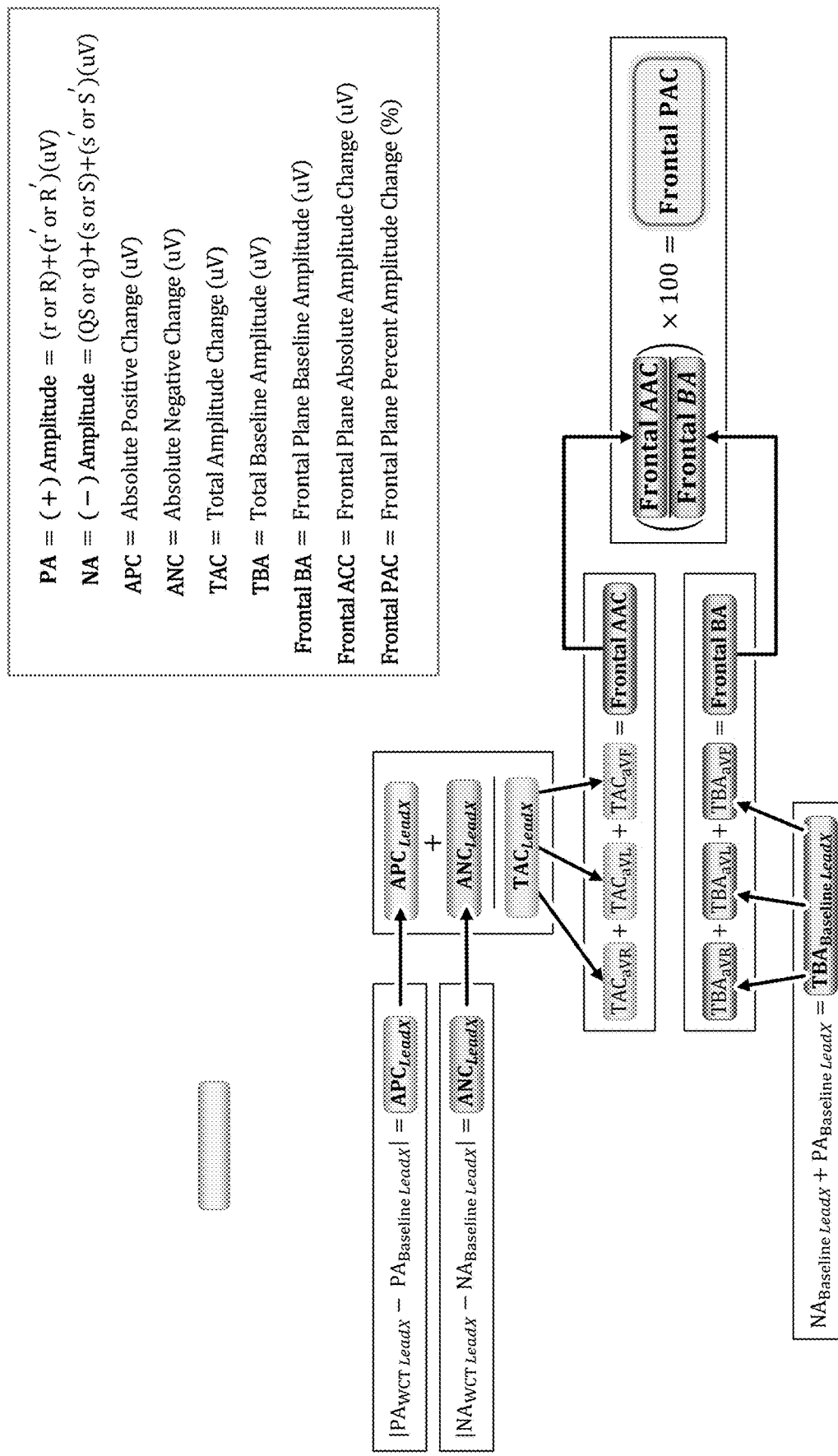
Figure 6B:
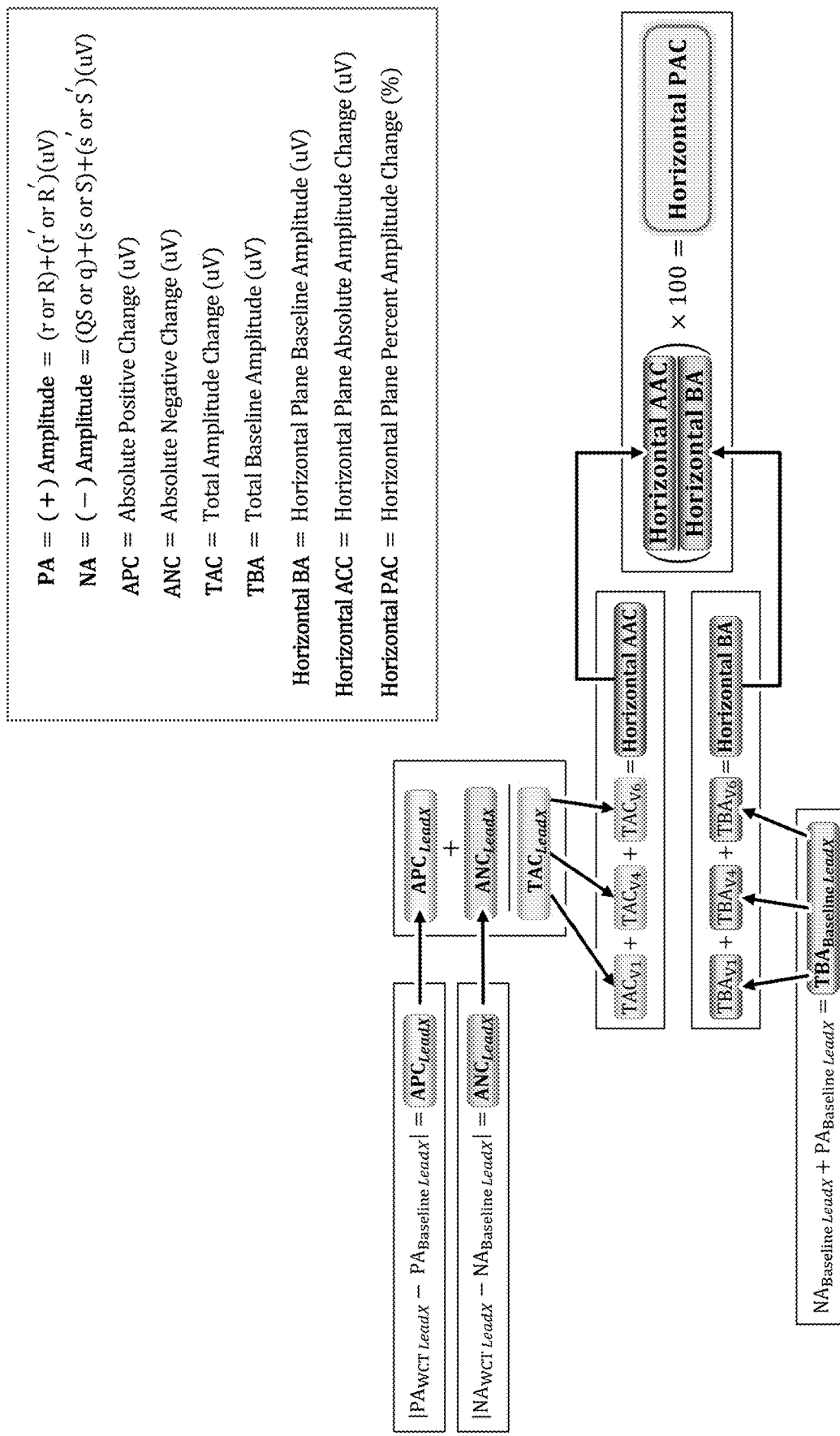

A diagram showing the derivation of the frontal PAC formula and horizontal PAC formula are shown in FIGS. 6A and 6B, respectively.

As previously mentioned, the amplitude based WCT Formula is a binary outcome logistic regression model that uses select independent WCT predictors: (1) WCT duration (ms), (2) frontal PAC (%) and (3) horizontal PAC (%). Each WCT predictor ($X_x$) was assigned beta coefficients ($\beta_x$) according to their influence on the binary outcome (VT vs. non-VT). The "constant" term ($B_0$) represents the y-intercept of the least squares regression line. Discrete measured or calculated WCT predictor values derived from paired baseline and WCT ECGs are incorporated into the WCT Formula to calculate VT probability (P).

$$X_\beta = \ln\left(\frac{P_{VT}}{1 - P_{VT}}\right) = \beta_0 + \beta_1 X_1 + \beta_2 X_2 + \beta_3 X_3.$$

where:
  $X_\beta$ is the weighted sum of the WCT predictors;
  $P_{VT}$ is the probability of VT;
  $\beta_0$ is the Y intercept or constant;
  $\beta_n$ is the slope of the independent WCT predictor n;
  $X_n$ is the independent WCT predictor n; and
  independent WCT predictors n are $WCT_{duration}$, $PAC_{frontal}$, and $PAC_{horizontal}$ $$P_{VT} = \frac{e^{X_\beta}}{1 + e^{X_\beta}}$$

$$P_{VT} = \frac{e^{(a+b \times WCT_{duration} + c \times PAC_{frontal} + d \times PAC_{horizontal})}}{1 + e^{(a+b \times WCT_{duration} + c \times PAC_{frontal} + d \times PAC_{horizontal})}}$$

where a, b, c and d are constants:
  a=intercept=−14.5607;
  b=WCT QRS duration=0.0627;
  c=frontal % change in area=0.284; and
  d=horizontal % change in area=0.0395.

$$P_{VT} = \frac{e^{(-14.5607 + 0.0627 \times WCT_{duration} + 0.284 \times PAC_{frontal} + 0.0395 \times PAC_{horizontal})}}{1 + e^{(-14.5607 + 0.0627 \times WCT_{duration} + 0.284 \times PAC_{frontal} + 0.0395 \times PAC_{horizontal})}}.$$

A diagram showing the amplitude based WCT Formula's logistic regression structure is shown in FIG. 6C.

Figure 7:
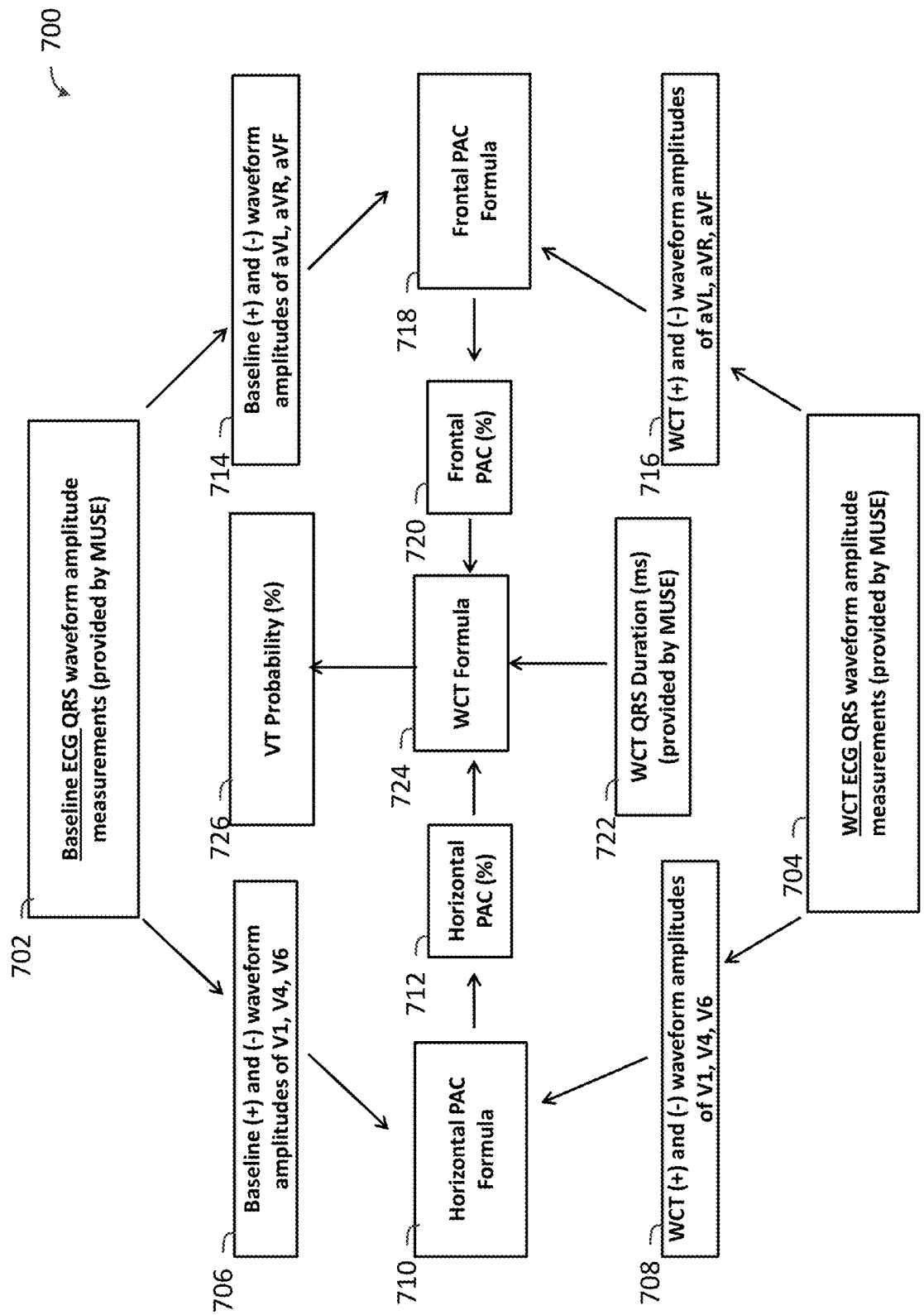
FIG. 7 depicts a flow diagram representing the inputs and output of the amplitude based WCT Formula in accordance with one embodiment of the present invention.

Referring now to FIG. 7, a flow diagram 700 representing the inputs and output of the amplitude based WCT Formula in accordance with one embodiment of the present invention is shown. The baseline ECG QRS waveform measurements may be obtained from GE Healthcare's MUSE or other computerized ECG interpretation software in block 702, and the WCT ECG QRS waveform measurements may be obtained from GE Healthcare's MUSE or other computerized ECG interpretation software in block 704. The baseline (+) and (−) waveform amplitudes of V1, V4, V6 in block 706 and WCT (+) and (−) waveform amplitudes of V1, V4, V6 in block 708 are used in the horizontal PAC formula in block 710 to provide the horizontal PAC (%) in block 712. The baseline (+) and (−) waveform amplitudes of aVL, aVR, aVF in block 714 and WCT (+) and (−) waveform amplitudes of aVL, aVR, aVF in block 716 are used in the frontal PAC formula in block 718 to provide the horizontal PAC (%) in block 720. The WCT QRS duration is provided in block 722, which is used along with the horizontal PAC (%) in block 712 and frontal PAC (%) in block 720 by the amplitude based WCT Formula in block 724 to provide the VT Probability (%) in block 726.

A two-part study was designed to build and validate the amplitude based WCT Formula capable of automatic VT probability estimation. In Part 1, a derivation cohort of paired WCT and subsequent baseline ECGs was used to construct a logistic regression model using the strongest independent predictors of VT and SWCT. Independent predictors including WCT QRS duration (ms), frontal ECG plane percent amplitude change (PAC) (%) and horizontal ECG plane percent amplitude change (PAC) (%) were incorporated into the amplitude based WCT Formula. In Part 2, the amplitude based WCT Formula's performance was prospectively tested using a separate validation cohort of paired WCT and subsequent baseline ECGs.

Paired WCT and subsequent baseline ECGs were derived from the Mayo Clinic Rochester and affiliated hospitals between September 2011 and November 2016. All ECGs were 12-lead recordings using standard paper speed (25 mm/s) and amplification (10 mm/mV). Electrocardiogram pairs were identified using a MUSE ECG databank system (GE Healthcare). Electrocardiograms fulfilling WCT criteria (QRS duration≥120 ms, heart rate≥100 bpm) plus an ECG laboratory interpretation diagnosis of (1) "ventricular tachycardia," (2) "supraventricular tachycardia," or (3) "wide complex tachycardia" were defined as WCT events. Baseline ECGs were defined as the most proximate non-WCT ECG obtained after the WCT event. Electrocardiogram pairs were excluded if the WCT did not have a subsequent baseline ECG or definite clinical diagnosis recorded within the patient's electronic medical record. Polymorphic VTs and irregular SWCTs with varying atrioventricular (AV) conduction were excluded. Abbreviated WCTs that were not the dominant rhythm featured on the 12-lead ECG were excluded. Electrocardiogram pairs found to have irreconcilable faulty measurements (eg. QRS amplitude measurement of a pacing spike) or alternative lead placements (eg. right-sided chest leads) were excluded.

This version of the WCT Formula was developed and tested using two cohorts. The derivation cohort consisted of 328 paired WCT (160 VT, 168 SWCT) and baseline ECGs from 229 patients presenting to the Mayo Clinic Rochester (September 2011-March 2015). The validation cohort was comprised of 313 paired WCT (123 VT, 190 SWCT) and baseline ECGs from 228 patients presenting to the Mayo Clinic Rochester and/or Mayo Clinic Health System of South Eastern Minnesota—including 40 additional patient care locations: community hospitals, emergency departments, and outpatient clinics (April 2015-November 2016).

Figure 8:
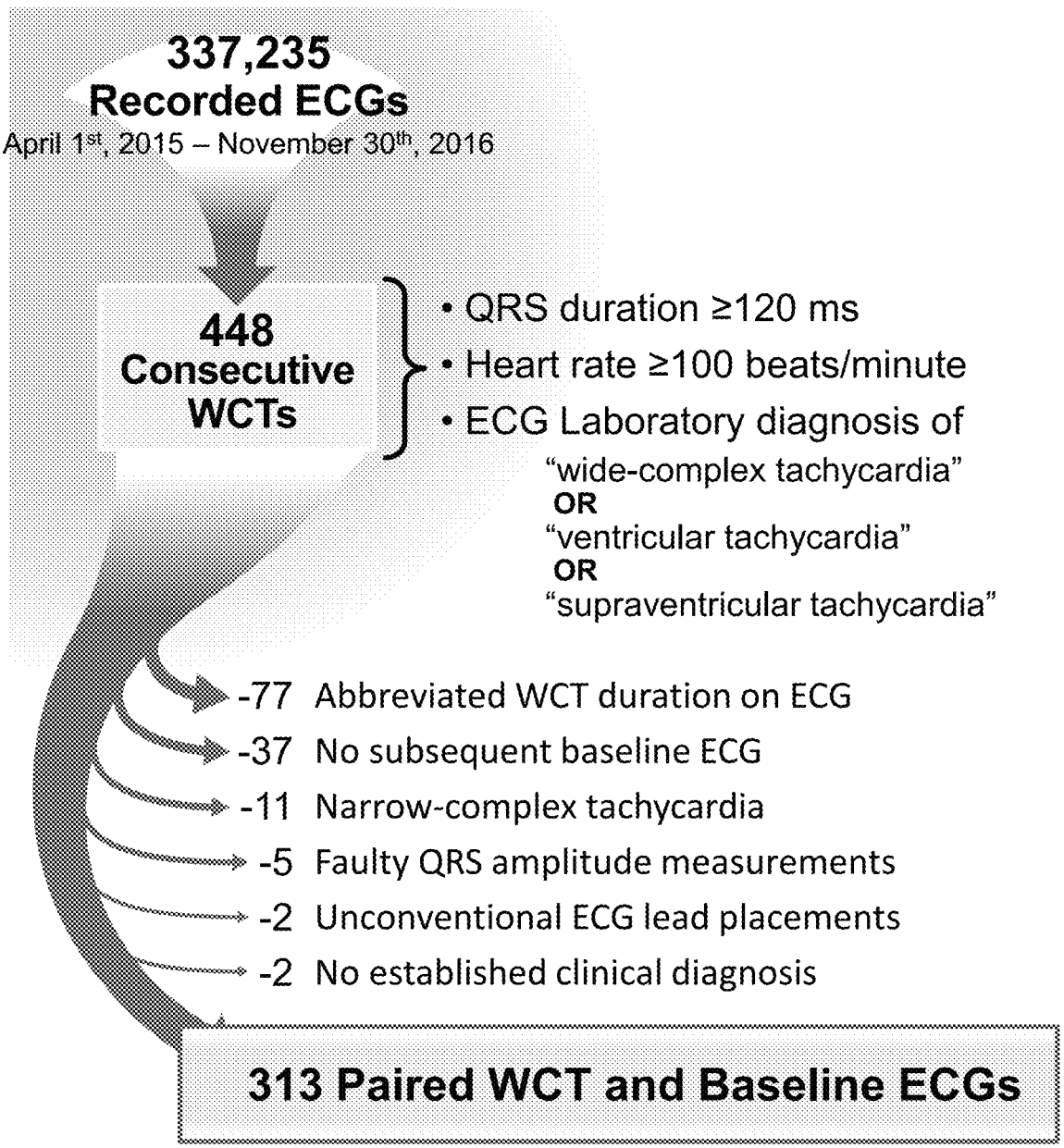
FIG. 8 illustrates the inclusion criteria and reasons for exclusion during validation cohort selection.

As shown in FIG. 8, various ECG pairs were excluded during validation cohort selection. Of the 337,235 recorded ECGs between Apr. 1, 2015 and Nov. 30, 2016, 448 consecutive WCTs were found that had a QRS duration greater than or equal to 120 ms, a heart rate greater than or equal to 100 beats/min and a ECG laboratory diagnosis of WCT or VT or SVT. One-hundred thirty-five out of 448 consecutive WCTs were excluded. More specifically, seventy-seven abbreviated WCTs that were not the dominant rhythm featured on the 12 lead ECG were excluded. Thirty-seven WCTs were excluded because there was no subsequent baseline ECG. Eleven WCTs demonstrated inappropriately prolonged QRS duration measurements for narrow complex SVTs. Five of the ECG pairs were excluded because of faulty QRS amplitude measurements of ventricular assist device artifact (n=1) or pacing spikes (n=4). Two of the ECG pairs were excluded due to unconventional ECG lead placements (i.e., right-sided chest leads). Two of the ECG pairs were exempted because they did not have an established clinical diagnosis. As a result, 313 paired WCT and baseline ECGs were used in the analysis.

All selected ECGs were formally interpreted at the Mayo Clinic ECG laboratory. ECG interpretation was under the supervision of a rotating consortium of attending cardiologists and electrophysiologists. Each supervising interpreter possessed extensive ECG interpretation experience along with complete access to the patient's electronic medical record (including archived 12-lead ECGs). The interpretation strategy utilized for each WCT was up to the supervising interpreter's discretion. The degree of diagnostic certainty reported by the ECG laboratory for each WCT was semi-quantitatively re-categorized: (1) definite VT, (2) probable VT, (3) definite SWCT, (4) probable SWCT and (5) undifferentiated. The time separation between the WCT and subsequent baseline ECG was recorded.

The patient's clinical diagnosis (VT or SWCT) was identified from the electronic medical record. The medical providers responsible for WCT diagnoses were categorized according to their level of expertise: (1) heart rhythm cardiologist, (2) non-heart rhythm cardiologist and (3) non-cardiologist. The final WCT rhythm diagnosis was determined by the patient's "most experienced" overseeing medical provider (heart rhythm cardiologist>non-heart rhythm cardiologist>non-cardiologist). Each diagnosing provider had access to the ECG laboratory's formal WCT interpretation. The completion of an electrophysiology procedure supporting the clinical diagnosis was recorded.

Clinical demographics including history of coronary artery disease (CAD), prior myocardial infarction (MI), prior cardiac surgery, congenital heart disease, cardiomyopathy (ischemic vs. non-ischemic), most proximate valuation of left ventricular ejection fraction (LVEF) (>=50%; 49-31%; <=30%), prior pacemaker or automatic implantable cardioverter-defibrillator (AICD) implantation, and ongoing Vaughan-Williams Class I and III antiarrhythmic drug (AAD) use were recorded from the electronic medical record.

Overall comparisons of continuous variables were completed using Wilcoxon rank-sum tests. Categorical variables were compared using Chi-square tests. Receiver operator curves were used to summarize selected independent continuous variables. Select independent predictors of VT and SWCT identified in the derivation cohort were used to generate the amplitude based WCT Formula. Designate independent variables (1) WCT duration (ms), (2) frontal PAC (%) and (3) horizontal PAC (%) were assigned beta coefficients according to their influence on the binary outcome (VT vs. non-VT). The amplitude based WCT Formula assigned an estimated VT probability (0.000%-99.999%) for each ECG pair of the validation cohort. The diagnostic value of various VT probability partitions were evaluated according to their agreement with clinical diagnosis. A 50% VT probability partition (VT=>50%; SWCT<50%) was used to assess for the amplitude based WCT Formula's agreement with ECG laboratory interpretation and clinical diagnosis. Diagnoses rendered by various VT probability partitions were used to assess its diagnostic performance (e.g., accuracy, sensitivity, specificity, positive likelihood ratio, negative likelihood ratio). Kappa statistics were applied to describe the diagnostic agreement between (1) clinical diagnosis, (2) ECG laboratory interpretation and (3) the amplitude based WCT Formula's 50% VT probability partition. McNemar's test was used to test for differences among diagnostic standards. Statistical analyses were completed using SAS version 9.4.

Now referring to FIG. 9, Table 1 shows the ECG characteristics of the derivation cohort, which consisted of 160 VTs and 168 SWCTs from 229 patients. The majority of clinical diagnoses were established by heart rhythm cardiologists or non-heart rhythm cardiologists (86.6%). The VT group had comparatively more clinical diagnoses established by heart rhythm cardiologists than the SWCT group (VT 93.8% vs. SWCT 44.6%, p<0.001). The SWCT group had a substantially higher percentage of clinical diagnoses established by non-cardiologists (SWCT 23.2% vs. VT 3.1%, p<0.001). The majority of WCTs were given definitive or probable interpretive diagnoses by the ECG laboratory (91.2%). Median time separation between the WCT event and subsequent baseline ECG was 9.5 hours. Most baseline ECGs were acquired within 24 hours of the WCT event (63.4%). Most clinical WCT diagnoses were not supplemented by the findings of an electrophysiology procedure (67.4%).

Referring now to FIG. 10, Table 2 shows the clinical characteristics of the derivation cohort. The majority of WCTs were derived from males (72.0%). The SWCT group included more events derived from females than the VT group (SWCT 36.9% vs. VT 17.8%, p<0.001). The average age of the VT group was 5.4 years younger than the SWCT group. The VT group included more events from patients with known CAD (p<0.001), prior MI (p<0.001), prior cardiac surgery (p=0.02), ongoing AAD use (p<0.001), ischemic cardiomyopathy (p<0.001), non-ischemic cardiomyopathy (p=0.03) and implanted AICD (p<0.001), while the SWCT group had more events from patients with pacemakers without defibrillator capability (p=0.005). The VT group possessed more events from patients with an LVEF<=30% (VT 50.0% vs. SWCT 25.6%, p<0.001), while the SWCT group had more events from patients with an LVEF>=50% (SWCT 57.7% vs. VT 21.3%, p<0.001). The SWCT group included more ECG pairs with baseline bundle branch block (BBB) (SWCT 65.5% vs. VT 18.1%, p<0.001). The VT group included more ECG pairs with baseline ventricular pacing (VT 43.1% vs. SWCT 6.0%, p<0.001).

Now referring to FIG. 11, Table 3 shows the ECG analysis for the derivation cohort. Significant differences between VT and SWCT groups were noted for baseline QRS duration (ms) (p=0.05), baseline QTc interval duration (ms) (p=0.05), WCT QRS duration (ms) (p<0.001), change in QRS duration (ms) (p<0.001), change in R wave axis (°) (p<0.001), change in T wave axis (°) (p<0.001), frontal PAC (%) (p<0.001) and horizontal PAC (%) (p<0.001).

Figure 12C:
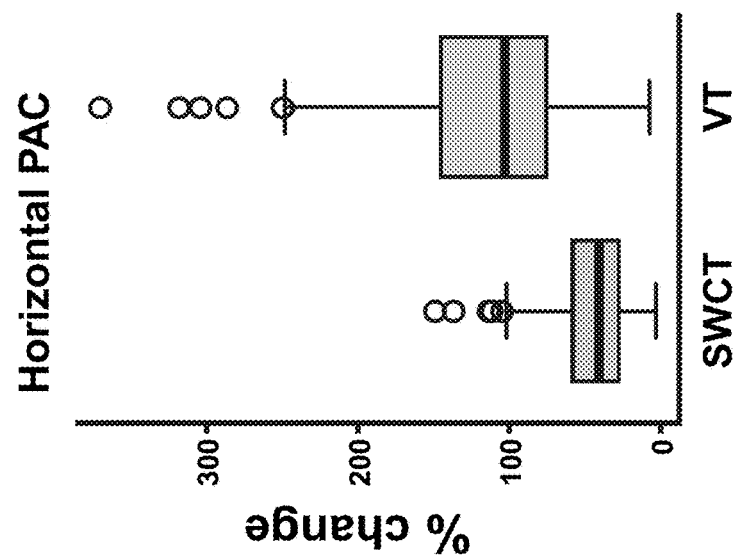
FIGS. 12A-12C are box-plots demonstrating the median and proportional distribution of WCT QRS duration (ms) (FIG. 12A), frontal PAC (%) (FIG. 12B) and Horizontal PAC (%) (FIG. 12C) for VT and SWCT groups in accordance with one embodiment of the present invention.
Figure 12B:
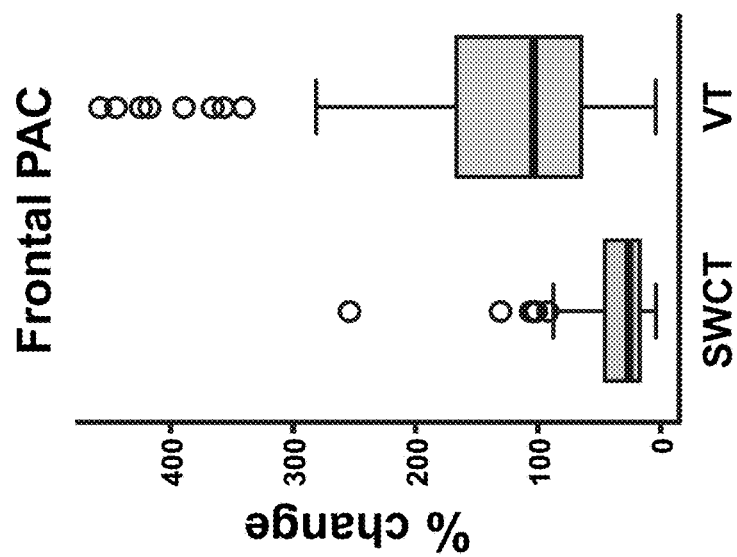
Figure 12A:
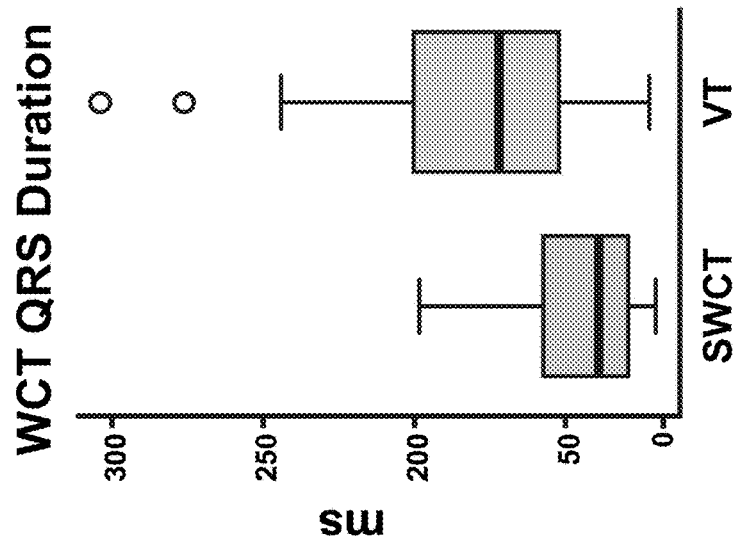

The mean and proportional distribution of WCT QRS duration (ms) was greater in the VT group (SWCT 144.0 vs. VT 177.4, p<0.001) (FIG. 12A). Differences in WCT QRS duration were also appreciated among baseline ECG sub-groups: QRS duration>=120 ms (SWCT 144.3 vs. VT 180.6, p<0.001), QRS duration<120 ms (SWCT 143.1 vs. VT 171.1, p<0.001) and ventricular pacing (SWCT 157.2 vs. VT 187.2, p<0.001) (see FIG. 12D).

The mean and proportional distribution of frontal PAC (%) was greater in the VT group (SWCT 34.9 vs. VT 123.7, p<0.001) (FIG. 12B). Differences in frontal PAC were also appreciated among baseline ECG sub-groups: QRS duration>=120 ms (SWCT 30.9 vs. VT 127.5, p<0.001), QRS duration<120 ms (SWCT 47.0 vs. VT 116.5, p<0.001) and ventricular pacing (SWCT 61.9 vs. VT 135.8, p=0.004) (see FIG. 12D).

The mean and proportional distribution of horizontal PAC (%) was greater in the VT group (SWCT 44.2 vs. VT 116.0, p<0.001) (FIG. 12C). Differences in horizontal PAC were also appreciated among baseline ECG sub-groups: QRS duration>=120 ms (SWCT 39.7 vs. VT 109.0, p<0.001), QRS duration<120 ms (SWCT 57.9 vs. VT 129.3, p<0.001) and ventricular pacing (SWCT 49.2 vs. VT 123.6, p<0.001) (see FIG. 12D).

Figure 13:
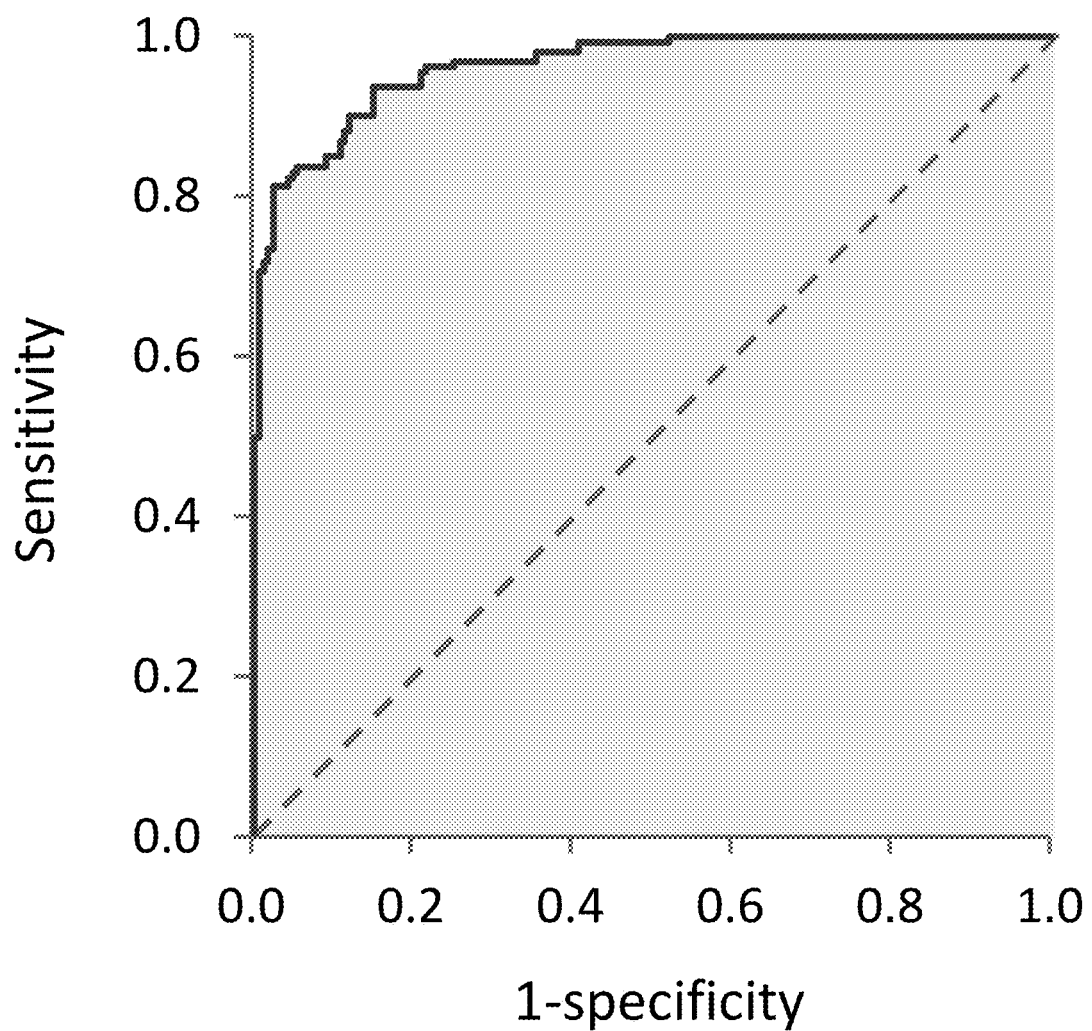
FIG. 13 is a graph of a receiver operating characteristic (ROC) curve depicting amplitude based WCT Formula diagnostic performance in accordance with one embodiment of the present invention.

As shown in FIG. 11, WCT predictors included baseline QRS duration (ms) (p=0.05), baseline QTc interval duration (ms) (p=0.05), WCT QRS duration (ms) (p<0.001), change in QRS duration (ms) (p<0.001), change in R wave axis (°) (p<0.001), change in T wave axis (°) (p<0.001), frontal PAC (%) (p<0.001) and horizontal PAC (%) (p<0.001). As shown in FIG. 13, the amplitude based WCT Formula diagnostic performance including (1) WCT QRS duration (ms), (2) frontal PAC (%) and (3) horizontal PAC (%) demonstrated favorable VT and SWCT differentiation (AUC of 0.96) using the derivation cohort (collection of paired WCT and baseline ECGs).

Referring now to FIG. 14, Table 4 shows the WCT event characteristics of the validation cohort, which consisted of 123 VTs and 190 SWCTs from 228 patients. The majority of clinical diagnoses were established by heart rhythm cardiologists or non-heart rhythm cardiologists (85.3%). The VT group had comparatively more clinical diagnoses established by heart rhythm cardiologists than the SWCT group (VT 87.8% vs. SWCT 43.7%, p<0.001). The SWCT group had a substantially higher percentage of clinical diagnoses established by non-cardiologists (SWCT 22.6% vs. VT 2.4%, p<0.001). The validation cohort included comparatively more WCTs with definitive or probable interpretive diagnoses coded by the ECG laboratory than the derivation cohort (98.1% vs. 91.2%, p<0.001). Median time separation between the WCT event and subsequent baseline ECG was 4.7 hours. Most baseline ECGs were acquired within 24 hours of the WCT event (70.9%). Most clinical WCT diagnoses were not supplemented by the findings of an electrophysiology procedure (69.3%).

Now referring to FIG. 15, Table 5 shows the clinical characteristics of the validation cohort. The majority of WCTs were derived from males (74.8%). The SWCT group included more events derived from females than the VT group (SWCT 32.1% vs. VT 14.6%, p<0.001). The average age of the VT group was 4.4 years younger than the SWCT group. The VT group included more events from patients with known CAD (p<0.001), prior MI (p<0.001), ongoing AAD use (p<0.001), ischemic cardiomyopathy (p<0.001) and implanted AICD (p<0.001), while the SWCT group had more events from patients with pacemakers without defibrillator capability (p=0.01). The VT group possessed more events from patients with an LVEF<=30% (VT 35.8% vs. SWCT 12.6%, p<0.001), while the SWCT group had more events from patients with an LVEF>=50% (SWCT 59.5% vs. VT 30.1%, p<0.001). The SWCT group included more ECG pairs with baseline BBB (SWCT 68.4% vs. VT 12.2%, p<0.001). The VT group included more ECG pairs with baseline ventricular pacing (VT 34.2% vs. SWCT 5.3%, p<0.001).

Referring now to FIGS. 16A and 16B, histograms demonstrating the distribution of clinical SWCT and VT for the validation cohort according to the amplitude based WCT Formula diagnostic performance at VT probability estimates (0.000%-99.999%) are shown in accordance with one embodiment of the present invention. Note that VT probability bins on the x-axis are arranged by 5.0% increments. Most VTs (77.2%) were categorized as having high VT probability (=>90.0%) with a compatible positive predictive value (97.9%). Most SWCTs (72.1%) were categorized as having low VT probability (<10.0%) with a compatible negative predictive value (97.2%).

Now referring to FIG. 17, Table 6 shows the VT probability partitions in accordance with one embodiment of the present invention. This version of the WCT Formula demonstrated favorable diagnostic characteristics across a wide variety of VT probability partitions. A VT probability partition of 50% (VT>=50%; SWCT<50%) yielded strong overall accuracy (92.0%) with high sensitivity (89.4%) and specificity (93.7%). A VT probability partition of 25% (VT=>25%; SWCT<25%) yielded higher sensitivity (94.3%) with a minimal reduction in overall accuracy (89.1%) and specificity (85.8%).

Figure 18A:
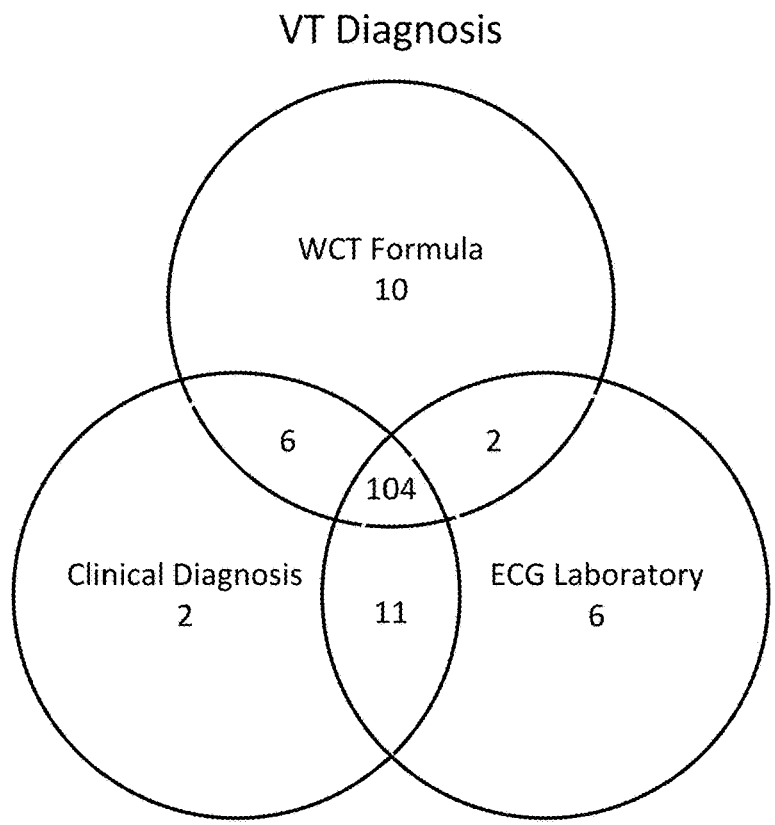
FIGS. 18A and 18B are Venn diagrams summarizing the distribution of shared and non-shared VT (FIG. 18A) and SWCT (FIG. 18B) diagnoses established by three diagnostic standards for the validation cohort: (1) clinical diagnosis, (2) ECG laboratory interpretation and (3) amplitude based WCT Formula's 50% VT probability partition.
Figure 18B:
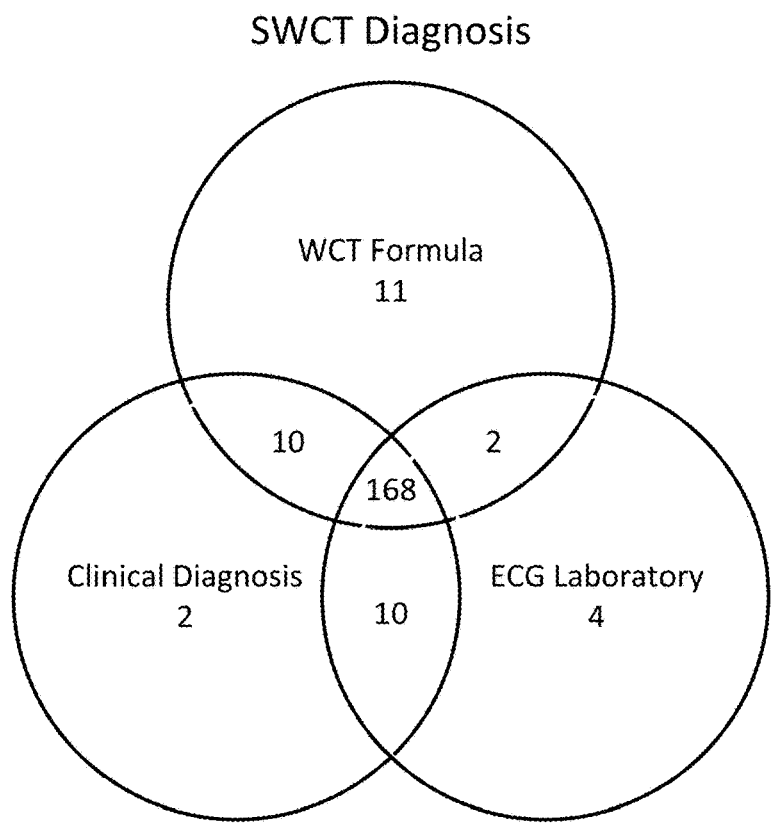

Referring now to FIGS. 18A and 18B, Venn diagrams summarizing the distribution of shared and non-shared VT (FIG. 18A) and SWCT (FIG. 18B) diagnoses established by three diagnostic standards: (1) clinical diagnosis, (2) ECG laboratory interpretation and (3) amplitude based WCT Formula's 50% VT probability cut-point are shown. Wide complex tachycardias without definitive VT or SWCT diagnoses coded by the ECG laboratory (ie. undifferentiated) were not included (6 total). The distribution of (1) clinical diagnoses, (2) ECG laboratory interpretations and (3) amplitude based WCT Formula diagnoses according to a VT probability cut-point of 50% reveals strong agreement between each diagnostic standard. The amplitude based WCT Formula's agreement with either or both ECG laboratory interpretation and clinical diagnosis for VT diagnoses was 91.1% and 84.6%, respectively. The amplitude based WCT Formula's agreement with either or both ECG laboratory interpretation and clinical diagnosis for SWCT diagnoses was 94.7% and 88.4%, respectively. The degree of agreement between each diagnostic standard for VT diagnoses was strong: (1) WCT Formula vs. ECG laboratory (κ=0.78, CI 0.71-0.85), (2) WCT Formula vs. clinical diagnosis (κ=0.83, CI 0.77-0.90) and (3) clinical diagnosis vs. ECG laboratory (κ=0.89, CI 0.84-0.94). Similarly, the degree of agreement between each diagnostic standard for SWCT diagnoses was strong: (1) WCT Formula vs. ECG laboratory (κ=0.72, CI 0.65-0.80), (2) WCT Formula vs. clinical diagnosis (κ=0.83, CI 0.77-0.90) and (3) clinical diagnosis vs. ECG laboratory (κ=0.85, CI 0.79-0.91). The WCT Formula and ECG laboratory did not differ in their degree of agreement with clinical diagnosis (p=0.86).

As show in in FIG. 19A, thirteen out of 123 (10.6%) "clinical VTs" were categorized as SWCT using the amplitude based WCT Formula's 50% VT probability partition—6 expressed a QRS duration<140 ms; 10 demonstrated a frontal plane R axis shift<40°; 4 exhibited an unchanged QRS configuration at lead V1; 3 exhibited an unchanged QRS configuration at lead V6.

As shown in FIG. 19B, twelve out of 190 (6.3%) "clinical SWCTs" were categorized as VT using the amplitude based WCT Formula's 50% VT probability partition—7 expressed a QRS duration=>160 ms; 9 demonstrated a frontal plane R axis shift>=40°; 5 exhibited QRS morphology changes at lead V1; 12 exhibited QRS morphology differences at lead.

This version of the WCT Formula accurately predicted the vast majority of WCTs in a prospective evaluation using paired WCT and baseline ECGs derived from clinical practice. Approximately 75% of WCTs from the validation cohort were accurately allocated as having high (=>90%) or low (<10%) VT probability. Additionally, the amplitude based WCT Formula's 50% and 25% VT probability partitions yielded favorable overall accuracy with strong sensitivity and specificity for VT.

The amplitude based WCT Formula's diagnoses agreed strongly with those provided by our institution's clinical diagnosis and ECG laboratory interpretation practices. Remarkably, despite the ECG laboratory's presumably strong influence on patients' final clinical diagnosis, the amplitude based WCT Formula was able to "match" the ECG laboratory's agreement with clinical diagnosis.

The amplitude based WCT Formula's 50% VT probability partition did not match the exceptional performance originally ascribed to the Brugada algorithm (accuracy 98.0%; sensitivity 98.7%; specificity 96.5%) or Lead II R-wave to peak time (RWPT) criterion (sensitivity 93.2%; specificity 99.3%) (6, 14). When compared to results first reported for Vereckei's lead aVR algorithm (12), the amplitude based WCT Formula's 50% VT probability cut-point appears to be less sensitive (lead aVR 96.5% vs. WCT Formula 89.4%) but more specific (lead aVR 75.0% vs. WCT Formula 93.7%). However, the amplitude based WCT Formula compares quite favorably to these other methods when they were appraised by independent authors (12, 15, 21-28). In general, independent validation studies have found that established manual methods typically misdiagnose 15-30% of evaluated WCTs. One emblematic study which compared five different methods (Brugada, Griffith, Bayesian, lead aVR, and RWPT) in a head-to-head fashion found that they achieved only moderate diagnostic accuracy (range 68.8%-77.5%) (25). Each method, aside from the RWPT criterion, demonstrated good sensitivity (range 87.1%-94.2%) but poor specificity (range 39.8%-59.2%) for VT. Contrariwise, the RWPT criterion was found to be non-sensitive (60.0%) and moderately specific (82.7%).

It is well understood that the success of contemporary, manually-applied algorithms or criteria is highly dependent upon the examiner interpreting the ECG. It is also important to understand that most studies that have derived or validated manual WCT differentiation methods used only experienced electrocardiographers within controlled research settings (1-9, 11, 12, 14, 15, 17-20, 24, 25, 27, 29). Although some independent studies utilized less experienced ECG interpreters (21-23, 26, 28, 30), no study has attempted to test interpreter proficiency within authentic clinical settings.

Moreover, in clinical practice, it can be readily observed that the reliable differentiation of WCTs using 12-lead ECGs belongs only to knowledgeable providers who have a firm grasp of the advantages and disadvantages of multiple ECG criteria or algorithms, and are capable of their careful, systematic and simultaneous application. Apart from cardiologists and electrophysiologists this ability is not commonplace. Therefore, the efficacy of the published manual methods are likely lost through their misapplication or failed utilization by less skilled ECG interpreters This is especially likely when clinicians unexpectedly thrusted into the clinically challenging situation of managing a patient with WCT. The present invention, similar to any other automated diagnostic algorithm, does not suffer from these limitations.

The principal difference between the amplitude based WCT Formula and other established ECG interpretation methods is that it does not require manual ECG interpretation. Alternatively, the WCT Formula was designed to be automatically implemented by modern-day ECG interpretation software. Consequently, these methods escape the conventional challenges concerning provider recall (e.g., "What is the first step of the Brugada algorithm again?"), subjective interpretation (e.g., "Are those dissociated p waves?"), inter-observer disagreement (21, 23, 26, 27, 30), and precise manual measurement (e.g., Vi/Vt of Vereckei's aVR algorithm) characteristically present among manual interpretation strategies (1-15). Instead, the WCT Formula provides an automatic and reliable means to differentiate WCTs irrespective of the user's ECG interpretation abilities. As a result, the WCT Formulas can help protect against or supersede faulty diagnoses established by providers who incorrectly apply or fail to utilize manual interpretation methods.

The over-arching purpose of every ECG interpretation criteria or algorithm is to help providers accurately differentiate WCTs. The preferred strategy utilized by most methods is an "absolute" committed rhythm classification (VT vs. SWCT) according to the presence or absence of select differentiation criteria (6, 8, 9, 11-14). While this approach is meant to lead clinicians to the correct WCT diagnosis, it often leaves providers unaware of the likelihood that their diagnosis is actually correct because the published diagnostic sensitivity and specificity of the various ECG interpretation methods are usually not immediately available or remembered. Another drawback to this aforementioned strategy is that it tends to overlook the predictive contributions of other relevant criteria found (or not found) on a patient's ECG.

On the other hand, the amplitude based WCT Formula was designed to simultaneously evaluate and precisely "weigh" multiple coexistent WCT predictors to provide an automatic estimation of VT probability. As a result, the amplitude based WCT Formula is able to deliver to its users an accurate and timely VT probability estimation to help them commit to or reconsider VT or SWCT diagnoses. Additionally, the WCT Formula's logistic regression structure can allow the incorporation of other ECG measurements or calculations that may help to differentiate WCTs.

Furthermore, after decades of research into manually-operated ECG criteria or algorithms, researchers still do not have a clear understanding of their overall practical value. This is partially explained by the fact that all published ECG interpretation methods utilized select patient populations referred for electrophysiology procedures to derive (3, 5, 6, 11, 12, 14, 15) or evaluate (4, 8-10, 18, 19, 21-27, 29) their respective criteria or algorithms. Although this strategy is quite justified as it helps confirm the veracity of WCT diagnoses, it consequently leads to an underrepresentation of WCTs diagnosed and managed non-invasively (e.g., SWCTs due to pre-existing aberrancy), as well as an over-representation of WCTs needing further evaluation and/or ablative therapies (e.g., idiopathic VTs or SWCTs due to pre-excitation). Furthermore, most prior studies either intentionally excluded or did not sufficiently report the inclusion of patients with pre-existing BBB (3, 6, 8, 10, 14, 18, 19, 21-23, 27), ongoing AAD use (3, 6-10, 14, 18, 21, 22, 27), congenital heart disease (3-10, 12, 14, 15, 19, 21-23, 27), idiopathic VTs (3, 6, 8, 14, 21, 22, 27), or pre-excited SWCTs (3, 5-8, 14, 19, 21-23, 27). This observation is particularly important because several established ECG methods have been shown to have reduced accuracy when applied to WCT populations including these various subgroups (17, 20, 24-26, 29, 31).

In this study, approximately ⅔'s of WCTs did not have an accompanying electrophysiology procedure. As a result, the study population was comprised of many clinically encountered WCTs not customarily included in other studies. For example, the study cohorts included a higher percentage of patients with pre-existing BBB and ongoing AAD use than other studies (3-8, 10-12, 15, 18, 21-23, 25, 26). The SWCT groups were proportionally larger and included more events from patients with advanced age, CAD, prior MI and cardiomyopathy than other studies (4, 5, 11, 12, 15, 19, 23, 25, 26). Additionally, despite not being intentionally excluded, no pre-excited SWCTs were identified within the study cohorts. Although these dissimilarities primarily reflect the differing WCT selection strategy, they also indicate that the studies responsible for the derivation and evaluation of established ECG interpretation methods used select WCT populations different from what is regularly encountered in clinical practice.

According to the amplitude based WCT Formula's structure, "actual" VTs may be erroneously classified as SWCT if they demonstrate narrow QRS durations (e.g. fascicular VT) and/or very similar mean electrical vectors compared to the baseline ECG (e.g. bundle branch re-entry). Correspondingly, examples were observed where the amplitude based WCT Formula "missed VTs" with narrower QRS durations and/or similar QRS configurations compared to the baseline ECG (FIG. 19A). On the other hand, the amplitude based WCT Formula may erroneously classify "actual" SWCTs as VT if they express wider QRS durations (e.g. QRS prolongation due to ongoing antiarrhythmic drug use) and/or pronounced changes to the mean electrical vector (e.g. new left BBB aberrancy). Accordingly, we observed examples where the amplitude based WCT Formula erroneously predicted VT for clinical SWCTs exhibiting wider QRS durations and/or dissimilar QRS configurations compared to the baseline ECG (FIG. 19A).

The WCT Formula using time-voltage areas (ms/mV) of WCT ECG QRS waveforms instead of amplitudes will now be described. The included analyses pertaining to the time-voltage area based WCT Formula were derived from 641 paired WCT and baseline ECGs that constitute the summation of the derivation and validation cohorts.

Figure 20:
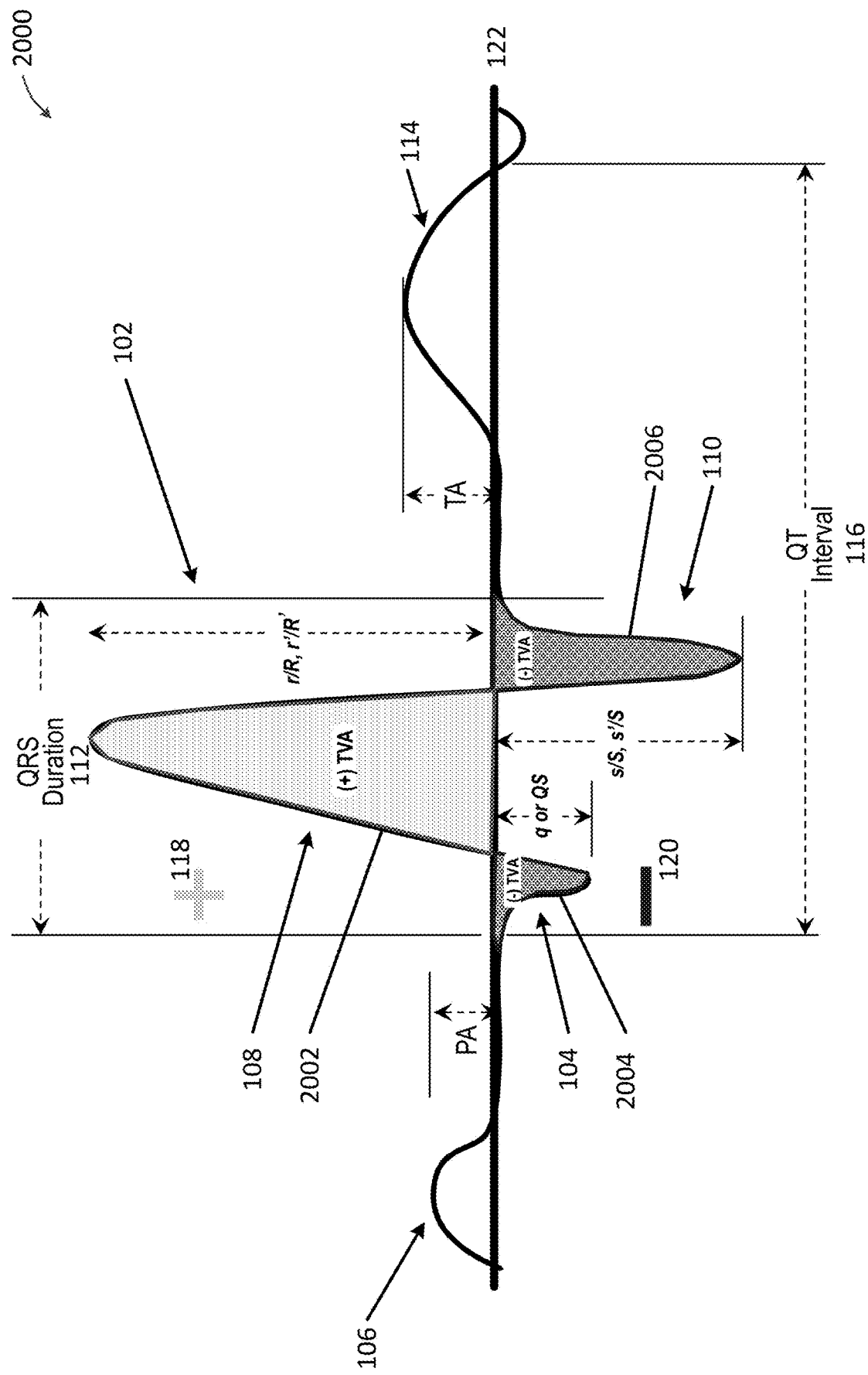
FIG. 20 depicts a schematic representation of a normal ECG with time-voltage areas.

Now referring to FIG. 20, a schematic representation of a stereotypical ECG pattern for a single heart beat 2000 is shown. The various waves were previously described in reference to FIG. 1A and common reference numerals are used for both figures. Each wave has amplitude denoted as PA, q (QS not shown), r/R (r'/R' not shown), or s/S (s'/S' not shown) and TA. In addition, the QT interval 116 is the time interval extending from the onset of the QRS complex waveform 102 to the end of the T wave 114. The QRS complex 102 is divided into positive (+) time-voltage areas (TVA) 118 and negative (−) TVAs 120. The positive (+) TVAs 118 are the TVAs of the vertical QRS complex deflections above the isoelectric baseline 122, namely the TVAs of r/R wave (and r'/R' not shown), wave 2002. The negative (−) TVAs 120 are the TVAs of the vertical QRS complex deflections below the isoelectric baseline 122, namely the TVAs of q (or QS wave not shown) 2004, and s/S (and s'/S' not shown) wave 2006. Computerized ECG interpretation software, such as the MUSE software provided by GE Healthcare, automatically measures QRS complex waveform 102 attributes, namely q or QS, r/R, s/S, r'/R', s'/S' durations (ms), amplitudes (μV), and time-voltage areas (μV·ms). Note that standard annotation of QRS complex waveforms of small QRS waveforms are in lower case and large QRS waveforms are in upper case.

Figure 21A:
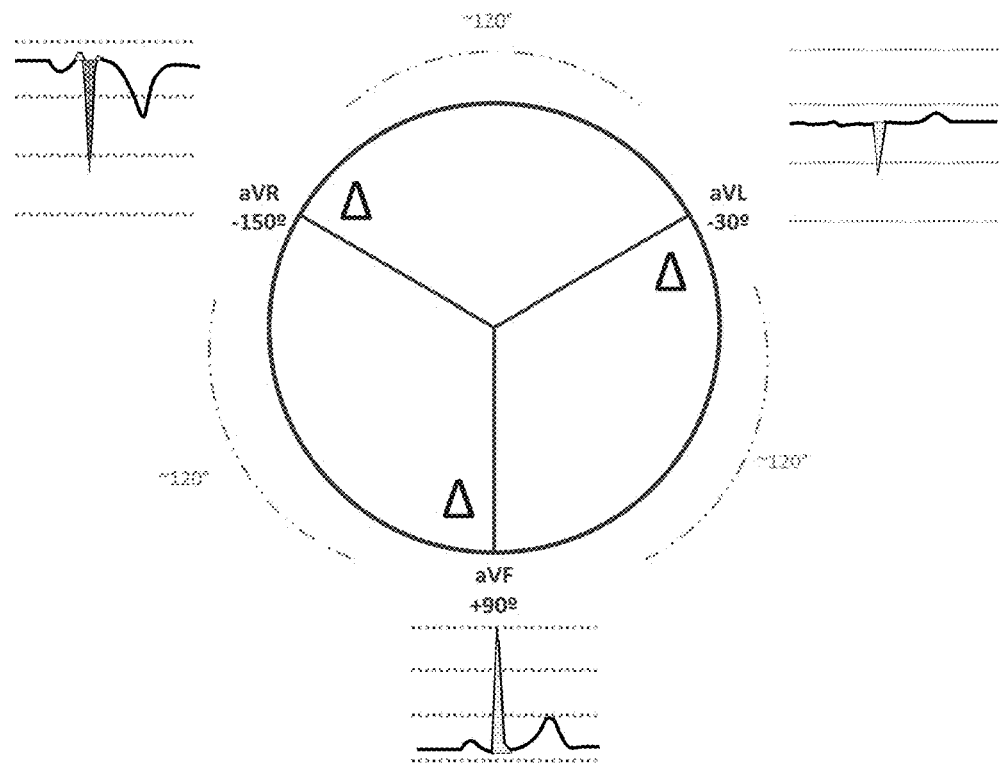
FIGS. 21A-21B are graphic depictions of select ECG lead combinations utilized by the frontal (aVR, aVL, aVF) and horizontal (V1, inverse V4, V6) PAC formulas with respect to time-voltage areas in accordance with one embodiment of the present invention.
Figure 21B:
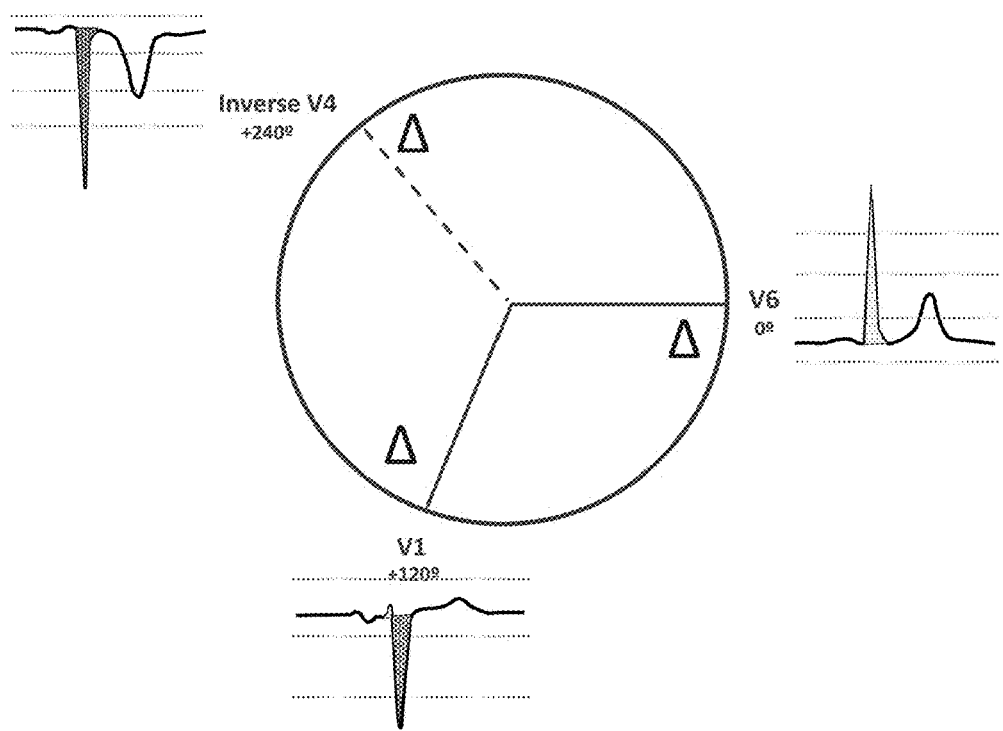
Figure 22:
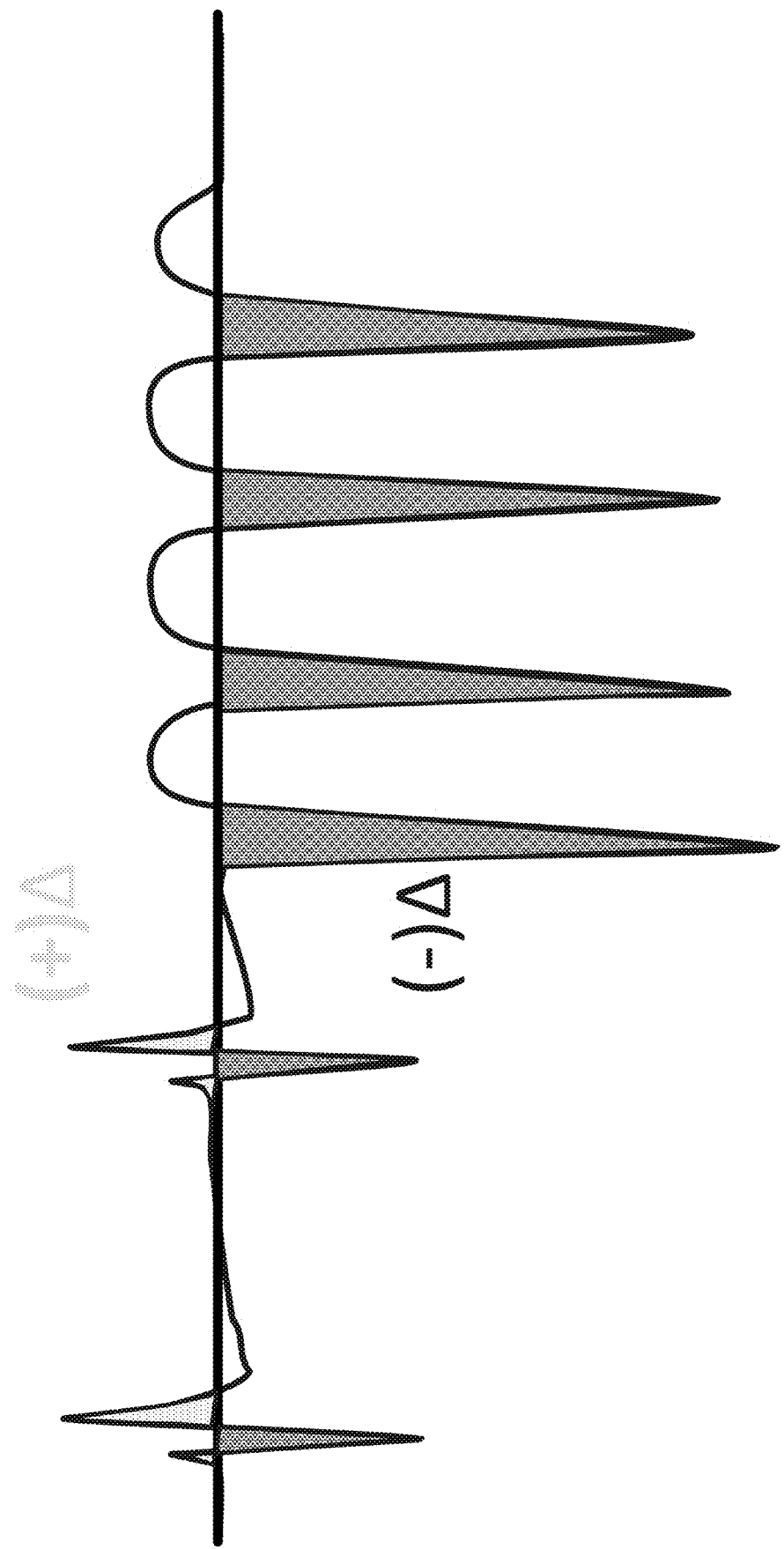
FIG. 22 depicts a schematic representation of the resultant QRS time-voltage area changes that manifest between a patient's baseline and WCT ECG.

Referring now to FIGS. 21A-21B, graphic depictions of select ECG lead combinations utilized by the frontal (aVR, aVL, aVF)(FIG. 21A) and horizontal (V1, inverse V4, V6)(FIG. 21B) percent time-voltage area change (PTVAC) formulas in accordance with one embodiment of the present invention are shown. The QRS time-voltage are change (Δ) that manifests between the baseline and WCT ECGs at these selected leads is the foundation for each PTVAC calculation. Note that the absolute QRS time-voltage area changes (Δ's) that manifest in lead V4 are mathematically equivalent to its planar opposite: inverse V4. FIG. 22 depicts a schematic representation of the resultant QRS time-voltage area changes that manifest between a patient's baseline and WCT ECG.

Figure 23A:
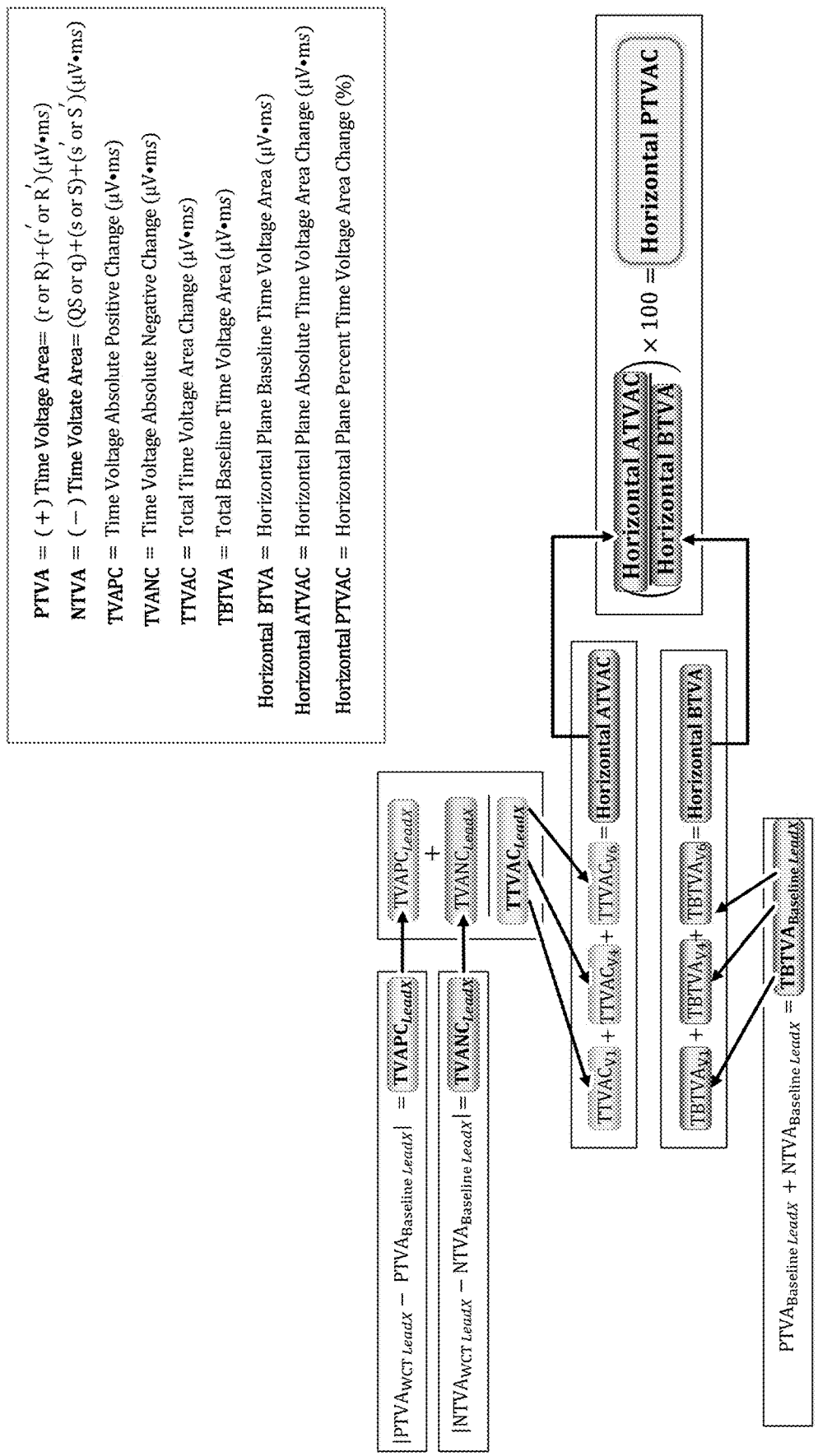
Figure 23B:
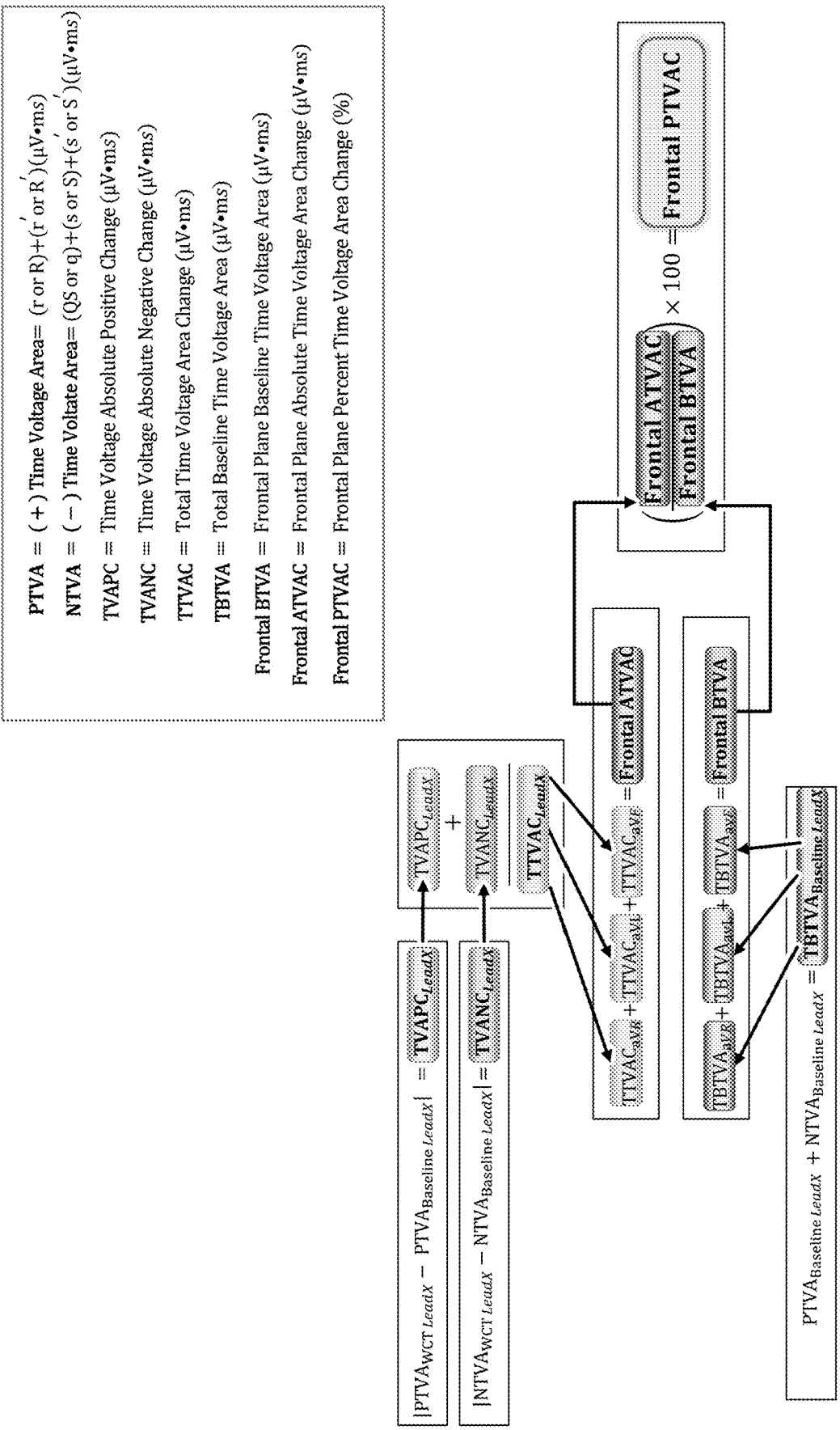

Now referring to FIGS. 23A-23B, the formulas for the horizontal PTVAC and frontal PTVAC are shown. The time-voltage area based WCT Formula incorporates the strong independent WCT predictors including (1) WCT QRS duration (ms), (2) frontal PTVAC (%) and (3) horizontal PTVAC (%). The predictive contribution of each WCT predictor is concomitantly "weighed" according to their influence on the binary outcome (VT vs. SWCT) to render a precise VT probability estimation. Given each WCT predictor's direct relationship with VT likelihood, the time-voltage area based WCT Formula estimates higher VT probabilities for ECG pairs demonstrating greater WCT QRS durations, frontal PTVAC and/or horizontal PTVAC. Similarly, the time-voltage area based WCT Formula estimates lower VT probability for ECG pairs with smaller WCT QRS durations, frontal PTVAC and/or horizontal PTVAC.

Similar to the amplitude based WCT Formula, the time-voltage area based WCT Formula is a multivariate logistic regression model that allows (1) delivery of precise VT probability predictions and (2) later inclusion of other well-established, enhanced and/or newly formulated WCT predictors. Other "machine learning" or artificial intelligence prediction methods (e.g., artificial neural networks, support vector machines, Random Forests, etc.) can be used with the frontal and horizontal PTVAC formulas. A step-wise decision-tree approach to diagnosis was avoided because of its tendency to prematurely commit to WCT diagnoses without considering the predictive strengths of other relevant predictors. The use of specific value cut-offs for VT diagnoses (e.g., QRS duration=>160 ms or frontal PAC>=75%) was avoided because they tend to cause (1) misclassifications due to VT and SWCT overlap and (2) ambiguity concerning the strength of WCT diagnoses for values distributed well above, well below, or at the margin of the designated cut-offs.

The time-voltage area based WCT Formula is a logistic regression formula that uses select independent WCT predictors (WCT QRS duration (ms), frontal PTVAC (%) and horizontal PTVAC (%)) to render a precise prediction of VT probability (%). Each WCT predictor ($X_x$) was assigned beta coefficients ($\beta_x$) according to their influence on the binary outcome (VT vs. non-VT). The "constant" term ($B_0$) represents the y-intercept of the least squares regression line. Discrete measured or calculated WCT predictor values derived from paired baseline and WCT ECGs are incorporated into the time-voltage area based WCT Formula to calculate VT probability ($P_{VT}$).

A calculation series is used to quantify the degree of QRS time-voltage area change that manifests between the baseline ECG and WCT event by converting raw ECG measurements into the frontal and horizontal PTVAC. The measured time-voltage areas (μV·ms) of QRS waveforms above (+) (r/R and r'/R') and below (−) (q/QS, s/S, and s'/S') the isoelectric baseline from select frontal (aVR, aVL, aVF) and horizontal (V1, V4, V6) ECG leads were used to derive each calculation. Baseline Time-Voltage Area (BTVA), Absolute Time-Voltage Area Change (ATVAC) and Percent Time-Voltage Area Change (PTVAC) were calculated for both the frontal and horizontal ECG planes.

$$TVAPC_{LeadX} = |(+)TimeVoltageArea_{WCT:LeadX} - (+)TimeVoltageArea_{Baseline:LeadX}|$$

$$TVANC_{LeadX} = |(-)TimeVoltageArea_{WCT:LeadX} - (-)TimeVoltageArea_{Baseline:LeadX}|$$

$$TTVAC_{LeadX} = ATAPC_{LeadX} + TVANC_{LeadX}$$

$$TBTVA_{Baseline:LeadX} = (-)TimeVoltageArea_{Baseline:LeadX} + (+)TimeVoltageArea_{Baseline:LeadX}$$

where: LeadX denotes V1, V4, V6 (horizontal plane) or aVL, aVR, aVF (frontal plane). Note that (−) TVA=q/QS+s/S+s'/S' and (+) TVA=r/R+r'/R'. Note that TVANC and TVAPC equations exhibit an "absolute" mathematical annotation (e.g. |equation's contents|).

Absolute Time-Voltage Area Change (ATVAC) represents the absolute summative difference in QRS time-voltage area between the WCT and baseline ECG.

$$Frontal\ ATVAC = TTVAC_{aVR} + TTVAC_{aVL} + TTVAC_{aVF}$$

$$Horizontal\ ATVAC = TTVAC_{V1} + TTVAC_{V4} + TTVAC_{V6}$$

Baseline Time-Voltage Area (BTVA) represents the total sum time-voltage area of (+) and (−) QRS waveforms in the baseline ECG.

$$Frontal\ BTVA = TBTVA_{aVR} + TBTVA_{aVL} + TBTVA_{aVF}$$

$$Horizontal\ BTVA = TBTVA_{V1} + TBTVA_{V4} + TBTVA_{V6}$$

Percent Time-Voltage Area Change (PTVAC) represents the percent change in QRS time-voltage area between the WCT and baseline ECG.

$$Frontal\ PTVAC(\%) = \left(\frac{Frontal\ ATVAC}{Frontal\ BTVA}\right) \times 100$$

$$Horizontal\ PTVAC(\%) = \left(\frac{Horizontal\ ATVAC}{Horizontal\ BTVA}\right) \times 100$$

As previously mentioned, the time-voltage area based WCT Formula is a binary outcome logistic regression formula that uses select independent WCT predictors: (1) WCT duration (ms), (2) frontal PTVAC (%) and (3) horizontal PTVAC (%). Each WCT predictor ($X_x$) was assigned beta coefficients ($\beta_x$) according to their influence on the binary outcome (VT vs. non-VT). The "constant" term ($B_0$) represents the y-intercept of the least squares regression line. Discrete measured or calculated WCT predictor values derived from paired baseline and WCT ECGs are incorporated into the time-voltage area based WCT Formula to calculate VT probability (P).

$$X_\beta = \ln\left(\frac{P_{VT}}{1 - P_{VT}}\right) = \beta_0 + \beta_1 X_1 + \beta_2 X_2 + \beta_3 X_3.$$

where:
  $X_\beta$ is the weighted sum of the WCT predictors;
  $P_{VT}$ is the probability of VT;
  $\beta_0$ is the Y intercept or constant;
  $\beta_n$ is the slope of the independent WCT predictor n;
  $X_n$ is the independent WCT predictor n; and
  independent WCT predictors n are $WCT_{duration}$, $PTVAC_{frontal}$, and $PTVAC_{horizontal}$ $$P_{VT} = \frac{e^{X_\beta}}{1+e^{X_\beta}}$$

$$P_{VT} = \frac{e^{(a+b\times WCT_{duration}+c\times PTVAC_{frontal}+d\times PTVAC_{horizontal})}}{1+e^{(a+b\times WCT_{duration}+c\times PTVAC_{frontal}+d\times PTVAC_{horizontal})}}$$

where a, b, c and d are constants:
  a=intercept=−11.047775;
  b=WCT QRS duration=0.051762;
  c=frontal % change in time-voltage area=0.01675701; and
  d=horizontal % change in time-voltage area=0.00868261.

$$P_{VT} = \frac{e^{(-11.047775+0.051762\times WCT_{duration}+0.01675701\times PTVAC_{frontal}+0.00868261\times PTVAC_{horizontal})}}{1+e^{(-11.047775+0.051762\times WCT_{duration}+0.01675701\times PTVAC_{frontal}+0.00868261\times PTVAC_{horizontal})}}.$$

A diagram showing the amplitude based WCT Formula's logistic regression structure is shown in FIG. 23C.

Figure 24A:
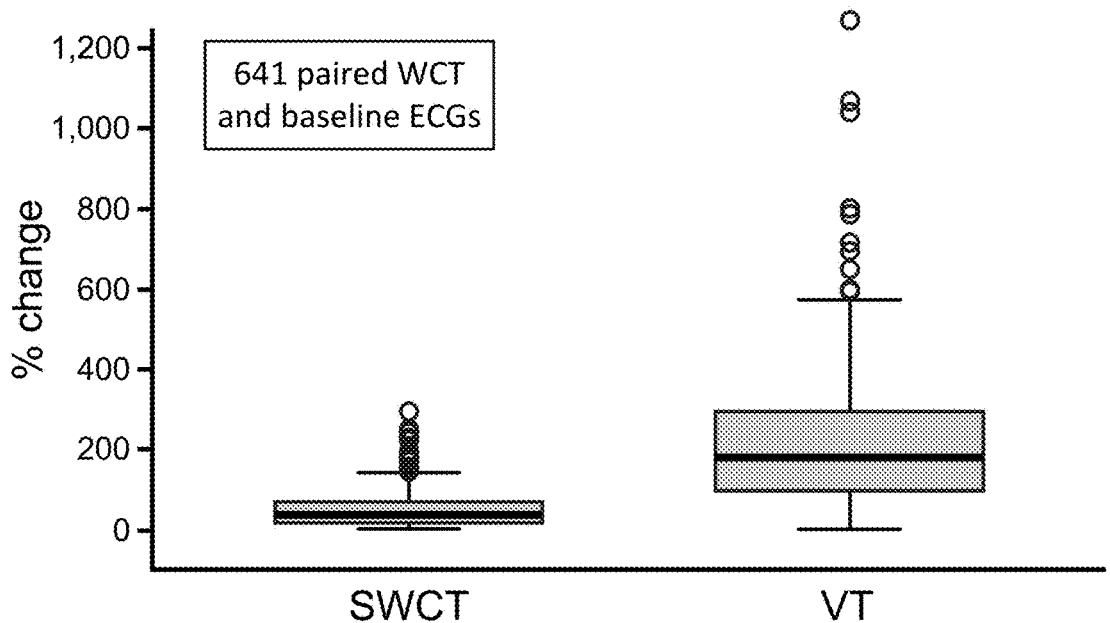
FIGS. 24A-24B are box-plots demonstrating the median and proportional distribution of frontal PTVAC (%) (FIG. 24A) and horizontal PTVAC (%) (FIG. 24B) for VT and SWCT groups in accordance with one embodiment of the present invention.
Figure 24B:
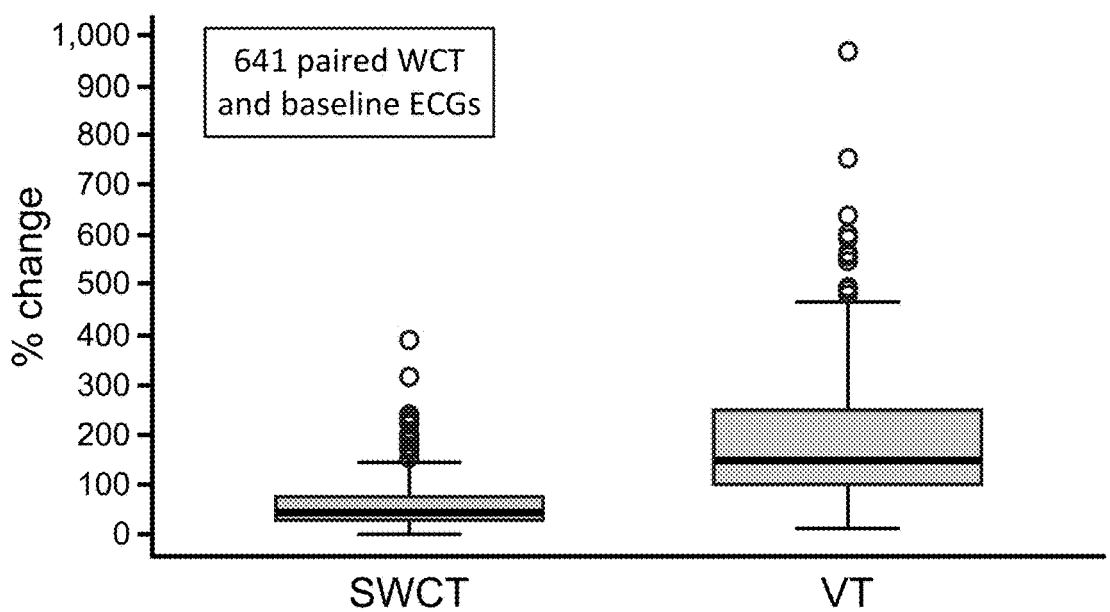

FIGS. 24A-24B are box-plots demonstrating the median and proportional distribution of frontal PTVAC (%) (FIG. 24A) and horizontal PTVAC (%) (FIG. 24B) for VT and SWCT groups in accordance with one embodiment of the present invention.

Figure 25A:
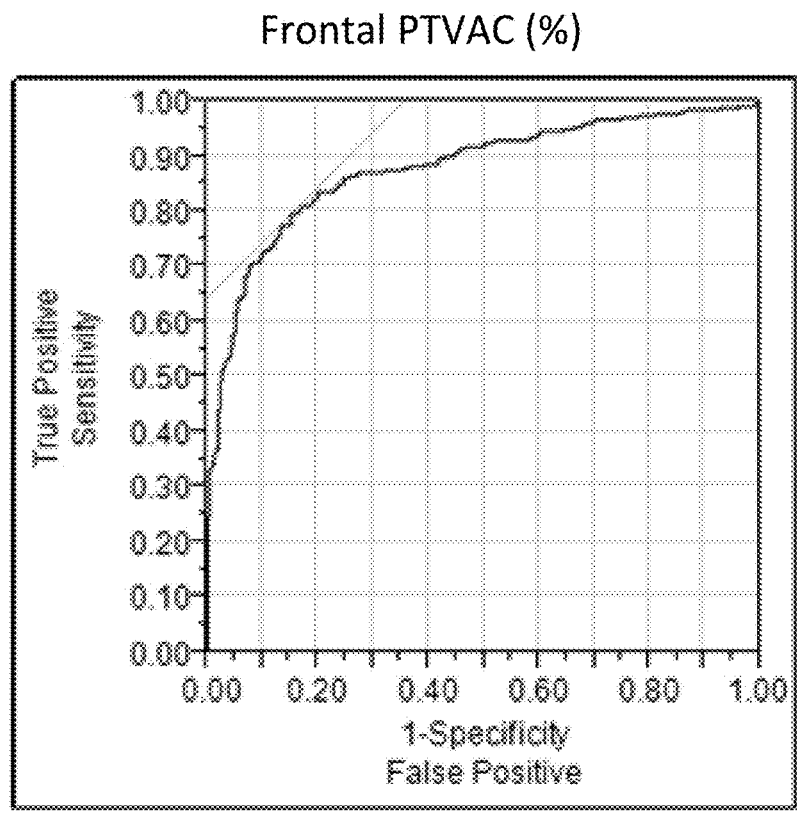
FIGS. 25A-25B are ROC graphs depicting the diagnostic performance of frontal PTVAC (%) (FIG. 25A) and horizontal PTVAC (%) (FIG. 25B) in accordance with one embodiment of the present invention.
Figure 25B:
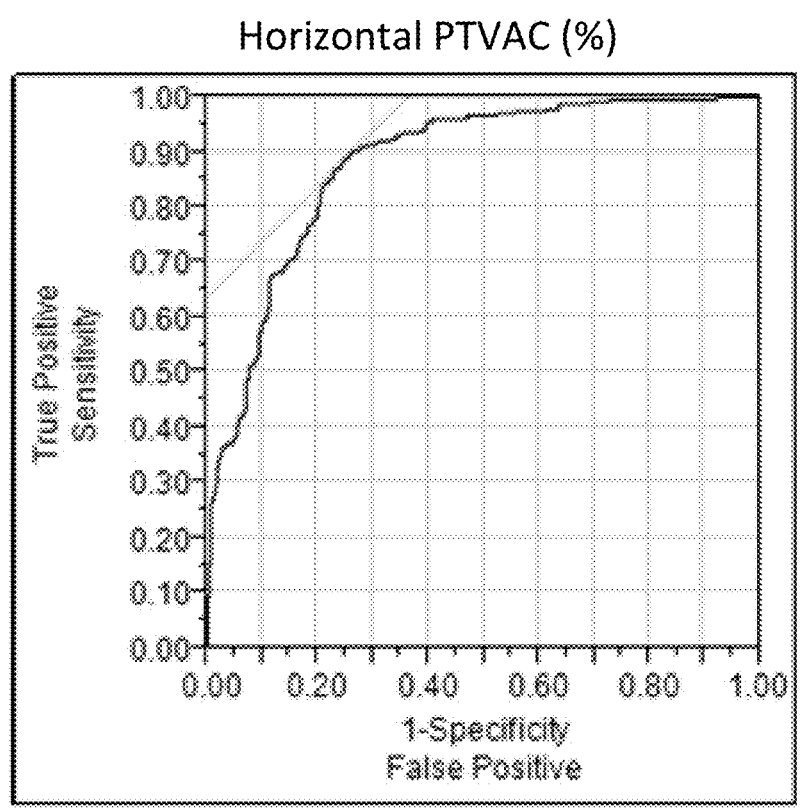

FIGS. 25A-25B are graphs depicting the frontal PTVAC (%) (FIG. 25A) and horizontal PTVAC (%) (FIG. 25B) in accordance with one embodiment of the present invention.

Figure 26:
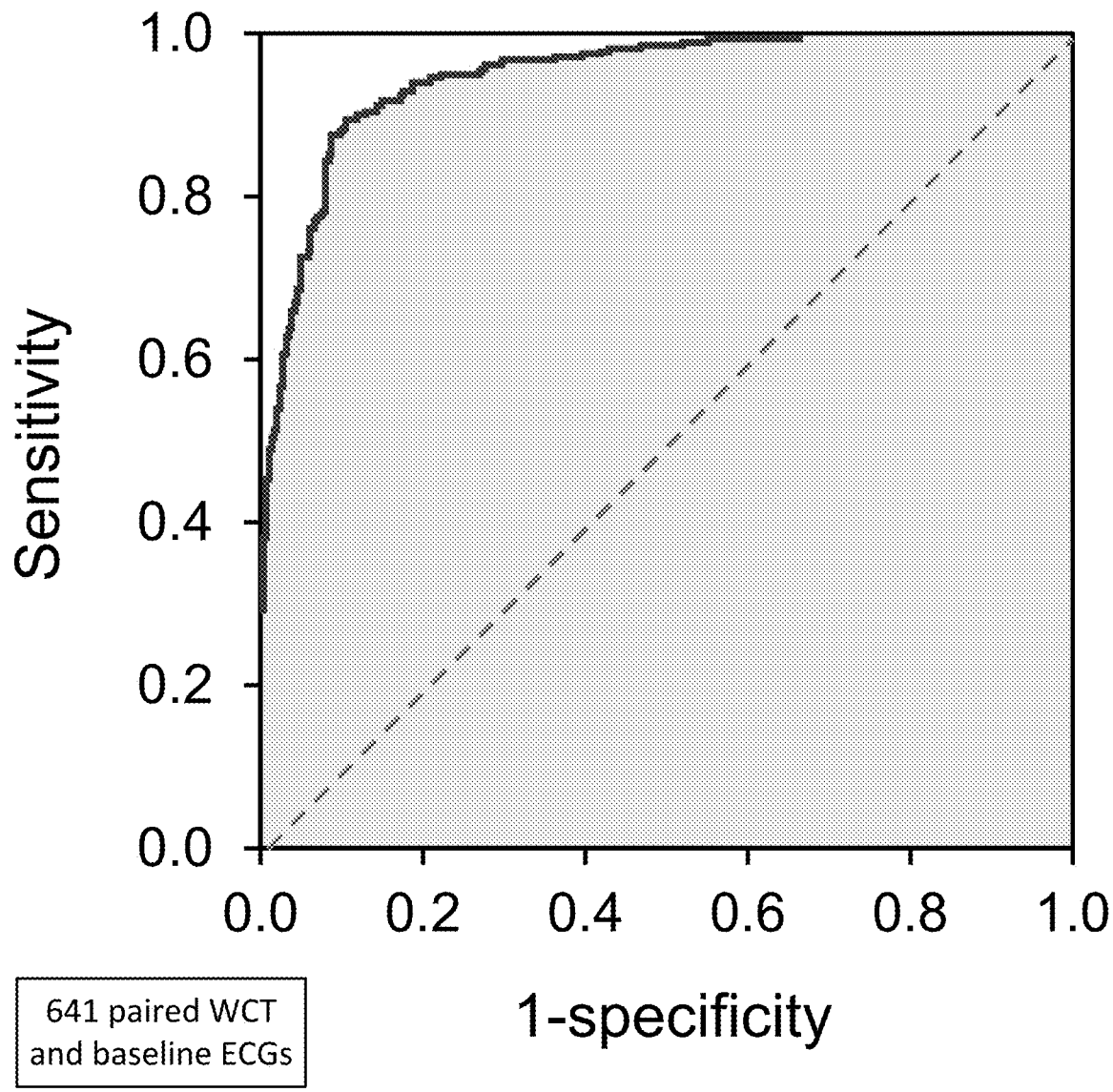
FIG. 26 is a graph depicting the time-voltage area based WCT Formula's diagnostic performance for the derivation cohort (AUC of 0.95) in accordance with one embodiment of the present invention.

FIG. 26 is a graph depicting the time-voltage area based WCT Formula diagnostic performance (AUC of 0.95) in accordance with one embodiment of the present invention.

Figure 27A:
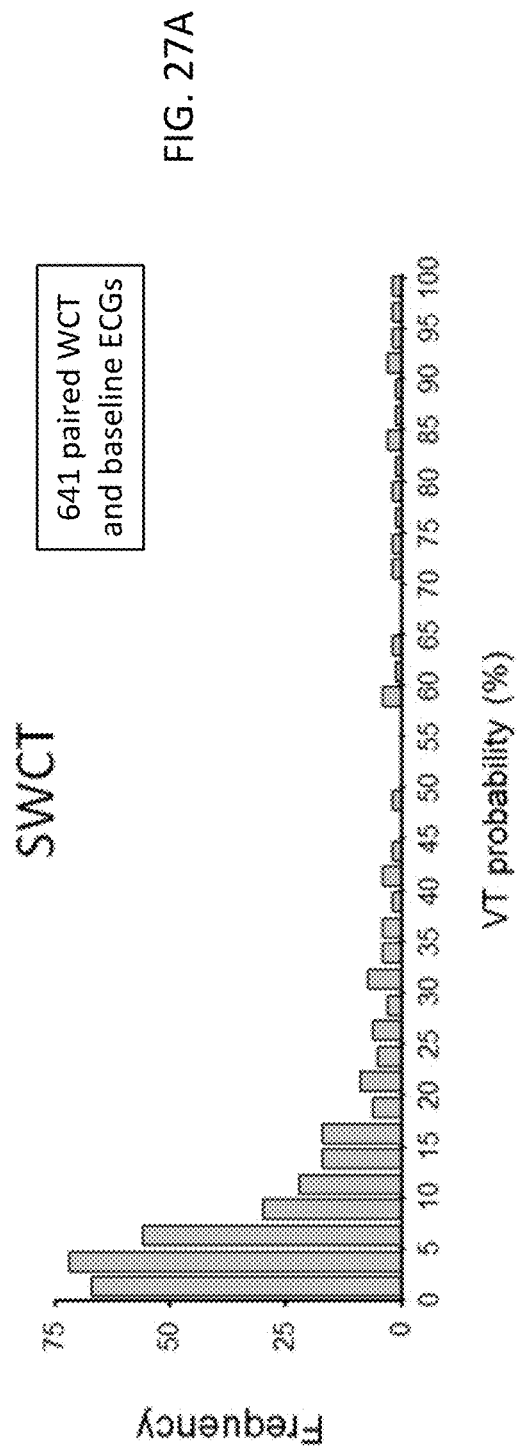
FIGS. 27A and 27B are histograms demonstrating the distribution of clinical VT and SWCT according to the time-voltage area based WCT Formula diagnostic performance at VT probability estimates (0.000%-99.999%)
Figure 27B:
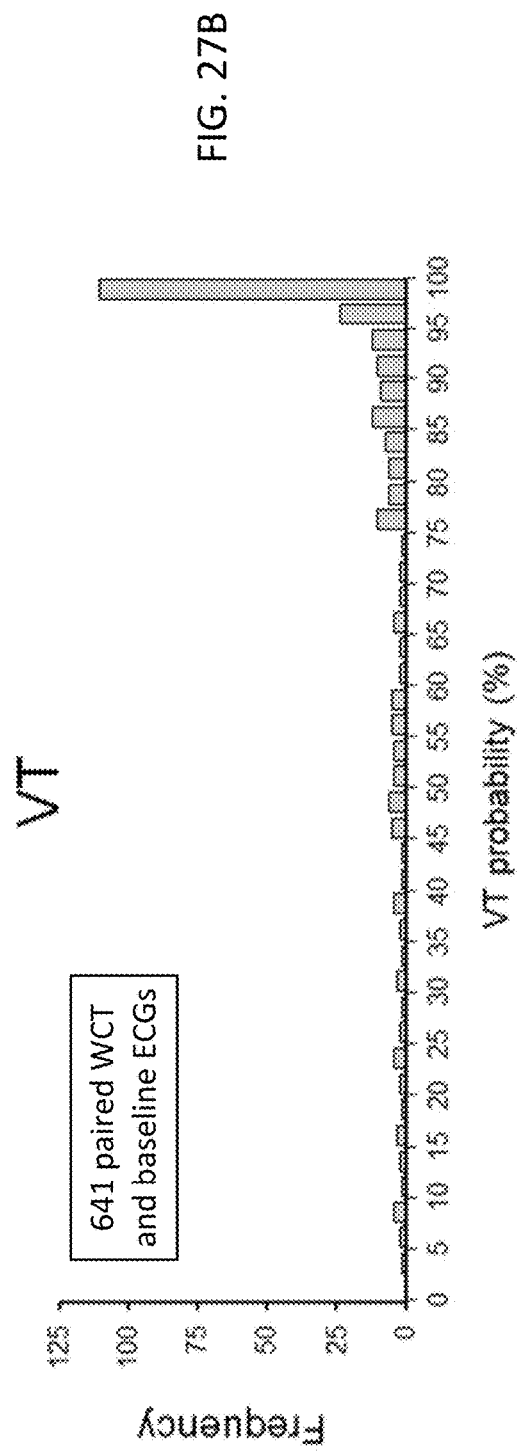

FIGS. 27A and 27B are histograms demonstrating the distribution of clinical VT probabilities according to the time-voltage area based WCT Formula diagnostic performance at VT probability estimates (0.000%-99.999%). The 641 paired WCT and baseline ECGs include both the validation and derivation cohorts.

The following discussion refers to both the amplitude and time-voltage area versions of the WCT Formula. The WCT Formulas relies upon the presumed accuracy of ECG software measurements. Moreover, the WCT Formulas require the simultaneous evaluation of the WCT and baseline ECG. Before the technological advances of ECG interpretation software and electronic databank storage systems, the automatic application of sophisticated computer algorithms using data from multiple ECGs was not feasible. Fortunately, contemporary ECG interpretation software is now able to simultaneously record, store and integrate data from multiple ECGs occurring before and after WCT events. Although the WCT Formulas' derivation and evaluation used only subsequent baseline ECGs, its performance would be quite similar if applied baseline ECGs preceding the WCT event. For clinical situations where WCT patients present without previously recorded ECGs, providers will need to rely upon conventional ECG interpretation methods until they obtain the patient's baseline ECG.

The WCT Formulas were derived from paired WCT and baseline ECGs acquired from clinical practice. Included WCTs did not require electrophysiology testing for further diagnostic confirmation. Although this selection strategy helps to avoid selection biases, it does not "guarantee" the accuracy of WCT diagnoses established by the ECG laboratory and clinicians. Nor does it allow a more comprehensive understanding of the strengths and weaknesses of both WCT Formulas that would be accomplished with electrophysiology testing.

The WCT Formulas were derived and evaluated using paired WCT and baseline ECGs separated by varying, sometimes lengthy, time intervals. As a consequence, deviations in ECG electrode placement and/or major changes to the patient's baseline ECG (e.g. new ventricular pacing following AICD implantation) may have influenced study results.

It is expected that the WCT formulas, or its electrophysiological principles, can be used on not only for 12-lead ECGs, but for any extended heart rhythm monitoring devices such as continuous ECG telemetry monitors, stress testing systems, extended monitoring devices (e.g., Holter monitors, etc.), smartphone-enabled ECG medical devices, cardioverter-defibrillator therapy devices, such as wearable cardioverter defibrillators (e.g., Zoll Life Vest), subcutaneous implantable cardioverter defibrillators (ICD) (e.g., Emblem S-ICD by Boston Scientific), pacemakers, automated external defibrillators (AED) (e.g., HeartStart OnSite AED by Phillips), and conventional automatic implantable cardioverter defibrillators (AICD).

In the foregoing study, the new WCT differentiation methods were found to be very accurate. The methods described could be automatically implemented by contemporary ECG interpretation software. The amplitude based and time-voltage area based WCT Formulas accurately predicted the vast majority of WCTs according to an institution's current clinical diagnosis practices. Although direct head-to-head comparisons were not undertaken, both WCT Formula methods compare favorably to the diagnostic performances ascribed to other ECG criteria or algorithms. Moreover, unlike established manual interpretation methods, the WCT Formulas are able to automatically provide accurate VT probability estimations for WCTs routinely encountered in clinical practice.

The fundamental purpose of every ECG criteria or algorithm is to help providers successfully differentiate WCTs. This invention provides examples of how modern-day ECG interpretation software could be used to help providers successfully differentiate VT and SWCT. This alternative approach to diagnosis has the natural advantage of automatically delivering precise estimations of VT probability to clinicians irrespective of their ECG interpretation abilities. In this manner, automated methods, like the amplitude based and time-voltage area based WCT Formulas, are particularly well-suited to help providers with less experience and/or differing clinical expertise provide accurate and timely WCT diagnoses. The incorporation of the present invention into computerized ECG interpretation software systems will not only supplement current diagnostic strategies but may also improve the quality of care provided to patients with WCT.

Furthermore, the WCT Formulas' principles could be applied by diagnostic ECG interpretation software to predict VT. As a result, the present invention is not limited to the WCT or PAC or PTVAC formulas. This new electrophysiological principle (degree of QRS complex change in amplitude or time-voltage area between the WCT and baseline ECG helps distinguish VT and SWCT) can be utilized by ECG interpretation software to render precise and accurate predictions of VT or SWCT.

Other embodiments of these similar WCT differentiation methods may be automatically implemented by computerized ECG interpretation (CEI) software. For example, another method which uses mathematically-synthesized signals and a more sophisticated machine learning techniques would serve as an alternative means to apply the electrophysiological principles of the WCT differentiation method.

Figure 28:
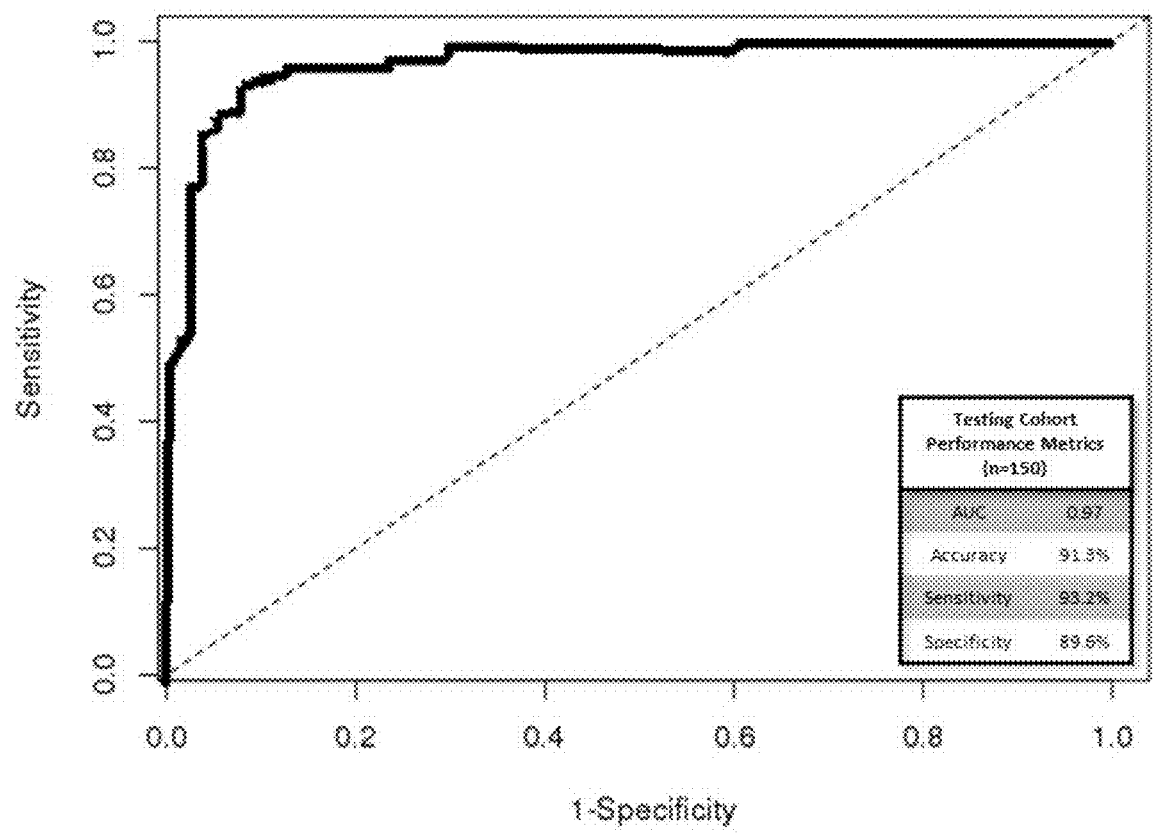
FIG. 28 is a graph depicting the VCG-VT Model's diagnostic performance for the testing cohort (AUC of 0.97) in accordance with one embodiment of the present invention.

For example, in a two-part analysis, paired WCT and baseline ECGs were used to derive and test a Random Forests model (i.e. VCG-VT Model) comprised of standard computerized ECG measurements and novel computations formulated from mathematically-synthesized vectorcardiogram (VCG) signals. These mathematically-synthesized vectorcardiogram (VCG) signals are derived from the electrical signals acquired from the 12-lead ECG. A derivation cohort comprised of 450 WCT (199 VT, 251 SWCT) and baseline ECG pairs was used to train a VCG-VT Model comprised of WCT QRS duration (ms), X-lead percent QRS amplitude change (%), Y-lead percent QRS amplitude change (%), and Z-lead percent QRS amplitude change (%). VCG-VT Model implementation on the testing cohort of 150 WCT (73 VT, 77 SWCT) and baseline ECG pairs resulted in an overall AUC, accuracy, sensitivity, and specificity of 0.97 (CI 0.94-0.99), 91.3% (CI 85.6%-95.3%), 93.2% (CI 84.7%-97.7%), and 89.6% (CI 80.6%-95.4%), respectively as shown in FIG. 28.

Additionally, the WCT Formula's electrophysiological principles may be applied to a wide variety of ECG, EMG and/or VCG analysis platforms beyond the diagnostic 12-lead ECG, including continuous ECG telemetry monitors, stress testing systems, extended monitoring devices (e.g., Holter monitors, etc.), smartphone-enabled ECG medical devices, cardioverter-defibrillator therapy devices, such as wearable cardioverter defibrillators (e.g., Zoll Life Vest), subcutaneous implantable cardioverter defibrillators (ICD) (e.g., Emblem S-ICD by Boston Scientific), pacemakers, automated external defibrillators (AED) (e.g., HeartStart OnSite AED by Phillips), and conventional automatic implantable cardioverter defibrillators (AICD). Measurements and calculations of EMG signals recorded from intracardiac (e.g. right ventricular AICD coil) and/or extracardiac electrodes (e.g. AICD generator housing) may also be used to established the degree (or percentage) of change in amplitude or time-voltage area between the WCT and baseline ventricular EMGs to help distinguish VT and SWCT. This discrimination process could be used to determine the need to deliver of device-related therapies, including anti-tachycardia pacing and defibrillator shocks.

Various embodiments of the present invention will now be described. These embodiments are merely examples and are not intended to limit the scope of the invention.

Figure 29:
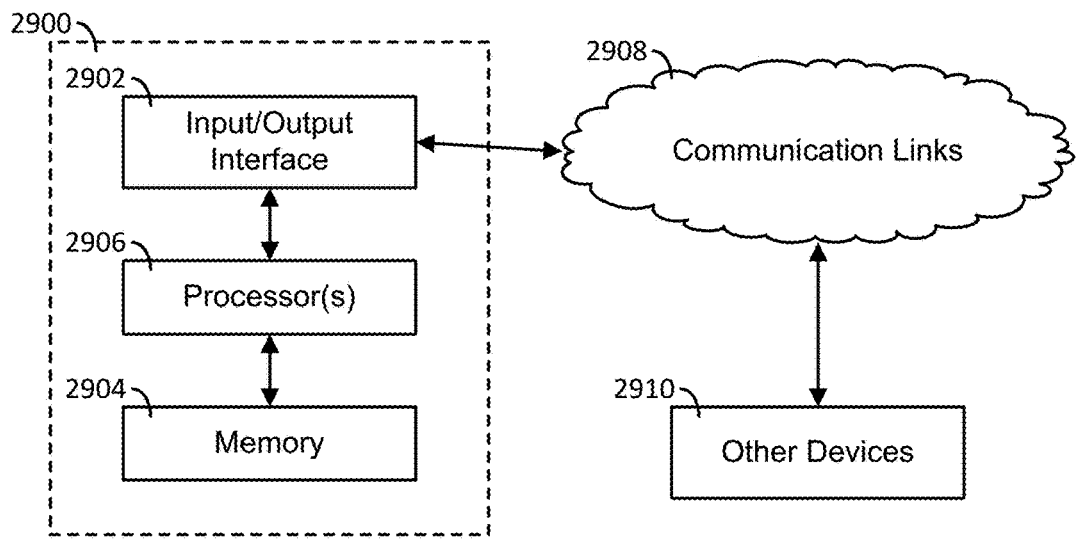
FIG. 29 is a block diagram of an apparatus in accordance with one embodiment of the present invention.

Now referring to FIG. 29, an apparatus 2900 for classifying a wide complex tachycardia (WCT) in accordance with the present invention is shown. The apparatus 2900 can be a server computer, a workstation computer, a laptop computer, a mobile communications device, a personal data assistant, a medical device or any other device capable of performing the functions described herein. The apparatus 2900 includes an input/output interface 2902, a memory 2904, and one or more processors 2906 communicably coupled to the input/output interface 2902 and the memory 2904. Note that the apparatus 2900 may include other components not specifically described herein. The memory 2904 can be local, remote or distributed. Likewise, the one or more processors 2906 can be local, remote or distributed. The input/output interface 2902 can be any mechanism for facilitating the input and/or output of information (e.g., web-based interface, touchscreen, keyboard, mouse, display, printer, etc.) Moreover, the input/output interface 2902 can be a remote device communicably coupled to the one or more processors 2906 via one or more communication links 2908 (e.g., network(s), cable(s), wireless, satellite, etc.). The one or more communication links 2908 can communicably couple the apparatus 2900 to other devices 2910 (e.g., databases, remote devices, hospitals, doctors, researchers, patients, etc.).

The one or more processors 2906 receive one or more wide complex heart beat waveform amplitudes and/or time-voltage areas, and one or more baseline heart beat waveform amplitudes and/or time-voltage areas via the input/output interface 2902 or the memory 2904, determine a signal change between the wide complex heart beat waveform amplitudes and/or time-voltage areas and the baseline heart beat waveform amplitudes and/or time-voltage areas, and provide the signal change via the input/output interface 2902, wherein the signal change provides an indication whether the wide complex heart beat(s) is from a ventricular source or a supraventricular aberrant condition. In one embodiment, the delivery of a signal change, such as % VT probability, to clinicians provides an invaluable diagnostic tool that allows them to use their clinical judgement as how to manage the patient. In another embodiment, the one or more processors 2906 provide the signal change via the input/output interface 2902 by automatically determining a wide complex heart beat classification for the wide complex heart beat(s) by comparing the signal change to a predetermined value using the one or more processors, and providing the wide complex heart beat classification via the input/output interface 2902.

Figure 30:
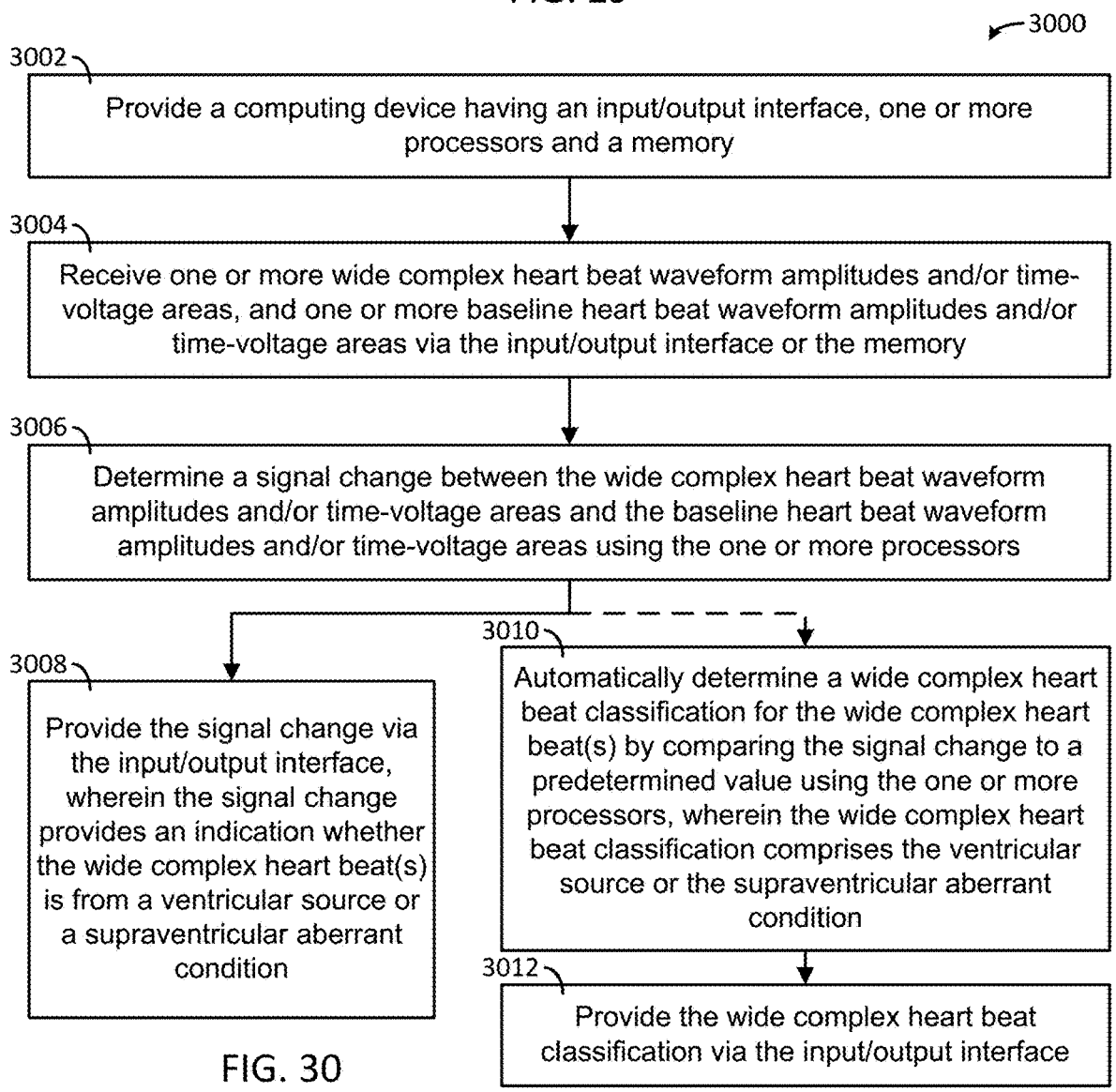
FIG. 30 is a flow chart of a method in accordance with one embodiment of the present invention.

Referring now to FIG. 30, a flow chart of a computerized method 3000 of automatically classifying a wide complex heart beat(s) is shown. A computing device having an input/output interface, one or more processors and a memory is provided in block 3002. One or more wide complex heart beat waveform amplitudes and/or time-voltage areas, and one or more baseline heart beat waveform amplitudes and/or time-voltage areas are received via the input/output interface or the memory in block 3004. A signal change between the wide complex heart beat waveform amplitudes and/or time-voltage areas and the baseline heart beat waveform amplitudes and/or time-voltage areas is determined using the one or more processors in block 3006. The signal change is provided via the input/output interface in block 3008, wherein the signal change provides an indication whether the wide complex heart beat(s) is from a ventricular source or a supraventricular aberrant condition. In another embodiment, a wide complex heart beat classification for the wide complex heart beat(s) is automatically determined by comparing the signal change to a predetermined value in block 3010, wherein the wide complex heart beat classification comprises the ventricular source or the supraventricular aberrant condition. The wide complex heart beat classification is provided via the input/output interface in block 3012. The signal change can be concomitantly "weighted" with other predictors of VT, SWCT or ventricular pacing. Moreover, the method can be implemented using a non-transitory computer readable medium that when executed causes the one or more processors to perform the method.

Now referring to FIGS. 29 and 30, other aspects of the present invention that are applicable to the apparatus 2900 and the method 3000 will now be described. In one aspect, the signal change further provides the indication whether the wide complex heart beat(s) is due to ventricular pacing. In another aspect, the wide complex heart beat(s) comprise a wide complex tachycardia (WCT), the ventricular source comprises a ventricular tachycardia (VT), and the supraventricular aberrant condition comprises a supraventricular wide complex tachycardia (SWCT). In another aspect, the signal change comprises a VT probability, the wide complex heart beat classification comprises a VT whenever the VT probability is greater than or equal to the predetermined value, and the wide complex heart beat classification comprises a SWCT whenever the VT probability is less than the predetermined value. In another aspect, the one or more processors select the predetermined value from a range of 0% to 100%. In another aspect, the predetermined value comprises about 1%, 10%, 25%, 50%, 75%, 90% or 99%. In another aspect, the one or more processors provide the signal change by providing a "shock" signal, a "no shock" signal, or no signal. In another aspect, the wide complex heart beat waveform amplitudes and/or time-voltage areas and the baseline heart beat waveform amplitudes and/or time-voltage areas are obtained from an electrocardiogram (ECG) QRS signal, a ventricular electrogram (EMG) signal, and/or a vectorcardiogram (VCG) signal. In another aspect, the wide complex heart beat waveform amplitudes and/or time-voltage areas comprise a plurality of measured amplitudes and/or time-voltage areas of a ECG QRS waveform, a EMG waveform and/or a VCG waveform above and below an isoelectric baseline; and the baseline heart beat waveform amplitudes and/or time-voltage areas comprise a plurality of measured amplitudes and/or time-voltage areas of a baseline ECG QRS waveform, a baseline EMG waveform and/or a baseline VCG waveform above and below the isoelectric baseline.

In another aspect, the one or more processors receive the one or more wide complex heart beat waveform amplitudes and/or time-voltage areas, and one or more baseline heart beat waveform amplitudes and/or time-voltage areas by: receiving a ECG QRS data, a EMG data, a VCG data and/or a mathematically synthesized VCG data via the input/output interface or the memory; receiving a baseline ECG QRS data, a baseline EMG data and/or a baseline VCG data via the input/output interface or the memory; determining the one or more waveform amplitudes and/or time-voltage areas from the ECG QRS data, the EMG data and/or the VCG data; and determining the one or more baseline waveform amplitudes and/or time-voltage areas from the baseline ECG QRS data, the baseline EMG data and/or the baseline VCG data. In another aspect, the ECG QRS data, the EMG data and/or the VCG data is generated or recorded before or after the baseline ECG QRS data, the baseline EMG data and/or the baseline VCG data. In another aspect, the ECG QRS data, the EMG data and/or the VCG data is generated or recorded after the baseline ECG QRS data, the baseline EMG data and/or the baseline VCG data and determining the signal change. In another aspect, the ECG QRS data, the EMG data and/or the VCG data and the baseline ECG QRS data, the baseline EMG data and/or the baseline VCG data are generated or recorded using one or more sensors or devices. In another aspect, the one or more sensors or devices comprise a 12-lead ECG device, a continuous ECG telemetry monitor, a stress testing system, an extended monitoring device, a smartphone-enabled ECG medical device, a cardioverter-defibrillator therapy device, a subcutaneous implantable cardioverter defibrillators (ICD), a pacemaker, an automated external defibrillators (AED), or an automatic implantable cardioverter defibrillator (AICD). In another aspect, the input/output interface, the memory and the one or more processors are integrated into the one or more sensors or devices; or the one or more sensors or devices are integrated into a computing device comprising the input/output interface, the memory and the one or more processors. In another aspect, the one or more processors determine the signal change between the wide complex heart beat waveform amplitudes and/or time-voltage areas and the baseline heart beat waveform amplitudes and/or time-voltage areas by: receiving a wide complex heart beat waveform duration via the input/output interface or the memory; determining a percent amplitude change (PAC) based on the wide complex heart beat waveform amplitudes and the baseline wide complex heart beat waveform amplitudes, and/or a percent time-voltage area change (PTVAC) based on the wide complex heart beat waveform time-voltage areas and the baseline wide complex heart beat waveform time-voltage areas; determining a classification probability based on the wide complex heart beat waveform duration, and the PAC and/or the PTVAC; and wherein the signal change comprises the classification probability, and the classification probability comprises a VT probability, a SWCT probability, or a ventricular pacing probability. In another aspect, determining the classification probability is further determined based one or more additional classification predictors. In another aspect, the PAC comprises a frontal PAC and a horizontal PAC, and the PTVAC comprises a frontal PTVAC and a horizontal PTVAC.

In another aspect, the one or more processors determine the signal change between the wide complex heart beat waveform amplitudes and/or time-voltage areas and the baseline heart beat waveform amplitudes and/or time-voltage areas by: receiving a WCT QRS duration via the input/output interface or the memory; the one or more wide complex heart beat waveform amplitudes and/or time-voltage areas comprise one or more frontal plane WCT positive waveform amplitudes and/or time-voltage areas, one or more horizontal plane WCT positive waveform amplitudes and/or time-voltage areas, one or more frontal plane WCT negative waveform amplitudes and/or time-voltage areas, and one or more horizontal plane WCT negative waveform amplitudes and/or time-voltage areas; the one or more the baseline heart beat waveform amplitudes and/or time-voltage areas comprise one or more frontal plane baseline positive waveform amplitudes and/or time-voltage areas, one or more horizontal plane baseline positive waveform amplitudes and/or time-voltage areas, one or more frontal plane baseline negative waveform amplitudes and/or time-voltage areas, and one or more horizontal baseline negative waveform amplitudes and/or time-voltage areas; determining (1) a frontal percent amplitude change (PAC) based on the one or more frontal plane WCT positive waveform amplitudes, one or more frontal plane WCT negative waveform amplitudes, one or more frontal plane baseline positive waveform amplitudes, and one or more frontal plane baseline negative waveform amplitudes, and/or (2) a frontal percent time-voltage area (PTVAC) based on the one or more frontal plane WCT positive waveform time-voltage areas, one or more frontal plane WCT negative waveform time-voltage areas, one or more frontal plane baseline positive waveform time-voltage areas, and one or more frontal plane baseline negative waveform time-voltage areas; determining (1) a horizontal PAC based on the one or more horizontal plane WCT positive waveform amplitudes, one or more horizontal plane WCT negative waveform amplitudes, one or more horizontal plane baseline positive waveform amplitudes, and one or more horizontal baseline negative waveform amplitudes, and/or (2) a horizontal PTVAC based on the one or more horizontal plane WCT positive waveform time-voltage areas, one or more horizontal plane WCT negative waveform time-voltage areas, one or more horizontal plane baseline positive waveform time-voltage areas, and one or more horizontal baseline negative waveform time-voltage areas; determining a VT probability using a statistical or machine learning process based on the WCT QRS duration and (1) the frontal PAC and the horizontal PAC, and/or (2) the frontal PTVAC and the horizontal PTVAC; and wherein the signal change comprises the VT probability. In another aspect, the statistical or machine learning process comprises a linear regression algorithm, a logistic regression model, a linear discriminate analysis algorithm, a Naive Bayes algorithm, a computational model using artificial neural networks, a computational model based on classification or regression trees, a k-nearest neighbors based model, a support vector machine based model, a boosting algorithm, or an ensemble machine learning algorithm.

In another aspect, the frontal PAC is determined by $$\text{Frontal } PAC(\%) = \left(\frac{\text{Frontal } AAC}{\text{Frontal } BA}\right) \times 100,$$

where: Frontal $AAC=TAC_{aVR}+TAC_{aVL}+TAC_{aVF}$, Frontal $BA=TBA_{aVR}+TBA_{aVL}+TBA_{aVF}$, $TAC_{LeadX}=APC_{LeadX}+ANC_{LeadX}$, $TBA_{Baseline:LeadX}=(-)\text{Amplitude}_{Baseline:LeadX}+(+)\text{Amplitude}_{Baseline:LeadX}$, $APC_{LeadX}=|(+)\text{Amplitude}_{WCT:LeadX}-(+)\text{Amplitude}_{Baseline:LeadX}|$, $ANC_{LeadX}=|(-)\text{Amplitude}_{WCT:LeadX}-(-)\text{Amplitude}_{Baseline:LeadX}|$, LeadX denotes V1, V4, V6 (horizontal plane) or aVL, aVR, aVF (frontal plane); the horizontal PAC is determined by $$\text{Horizontal } PAC(\%) = \left(\frac{\text{Horizontal } AAC}{\text{Horizontal } BA}\right) \times 100,$$

where: Horizontal $AAC=TAC_{V1}+TAC_{V4}+TAC_{V6}$, Horizontal $BA=TBA_{V1}+TBA_{V4}+TBA_{V6}$; and the VT probability ($P_{VT}$) is determined by:

$$P_{VT} = \frac{e^{(a+b \times WCT_{duration}+c \times PAC_{frontal}+d \times PAC_{horizontal})}}{1+e^{(a+b \times WCT_{duration}+c \times PAC_{frontal}+d \times PAC_{horizontal})}},$$

where a, b, c and d are constants. In another aspect, the frontal PTVAC is determined by $$\text{Frontal } PTVAC(\%) = \left(\frac{\text{Frontal } ATVAC}{\text{Frontal } BTVA}\right) \times 100,$$

where: Frontal $ATVAC=TTVAC_{aVR}+TTVAC_{aVL}+TTVAC_{aVF}$, Frontal $BTVA=TBTVA_{aVR}+TBTVA_{aVL}+TBTVA_{aVF}$, $TTVAC_{LeadX}=TVAPC_{LeadX}+TVANC_{LeadX}$, $TBTVA_{Baseline:LeadX}=(-)\text{TimeVoltageArea}_{Baseline:LeadX}+(+)\text{TimeVoltageArea}_{Baseline:LeadX}$, $TVAPC_{LeadX}=|(+)\text{TimeVoltageArea}_{WCT:LeadX}-(+)\text{TimeVoltageArea}_{Baseline:LeadX}|$, $TVANC_{LeadX}=|(-)\text{TimeVoltageArea}_{WCT:LeadX}-(-)\text{TimeVoltageArea}_{Baseline:LeadX}|$, LeadX denotes V1, V4, V6 (horizontal plane) or aVL, aVR, aVF (frontal plane); the horizontal PTVAC is determined by $$\text{Horizontal } PTVAC(\%) = \left(\frac{\text{Horizontal } ATVAC}{\text{Horizontal } BTVA}\right) \times 100,$$

where: Horizontal $ATVAC=TTVAC_{V1}+TTVAC_{V4}+TTVAC_{V6}$, Horizontal $BTVA=TBTVA_{V1}+TBTVA_{V4}+TBTVA_{V6}$; and the VT probability ($P_{VT}$) is determined by:

$$P_{VT} = \frac{e^{(a+b \times WCT_{duration}+c \times PTVAC_{frontal}+d \times PTVAC_{horizontal})}}{1+e^{(a+b \times WCT_{duration}+c \times PTVAC_{frontal}+d \times PTVAC_{horizontal})}},$$

where: a, b, c and d are constants.

In another aspect, the input/output interface comprises a remote device, and the remote device is communicably coupled to the one or more processors via one or more networks. In another aspect, the one or more processors provide a recommendation to select or exclude a therapy, medication, diagnostic testing or referral for a patient based on the signal change. In another aspect, apparatus comprises a server computer, a workstation computer, a laptop computer, a mobile communications device, a personal data assistant, or a medical device.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Sandler I A, Marriott H J. The Differential Morphology of Anomalous Ventricular Complexes of Rbbb-Type in Lead V; Ventricular Ectopy Versus Aberration. Circulation. 1965; 31:551-6.
2. Swanick E J, LaCamera F, Jr., Marriott H J. Morphologic features of right ventricular ectopic beats. Am J Cardiol. 1972; 30(8):888-91.
3. Wellens H J, Bar F W, Lie K I. The value of the electrocardiogram in the differential diagnosis of a tachycardia with a widened QRS complex. Am J Med. 1978; 64(1):27-33.
4. Akhtar M, Shenasa M, Jazayeri M, Caceres J, Tchou P J. Wide QRS complex tachycardia. Reappraisal of a common clinical problem. Ann Intern Med. 1988; 109(11): 905-12.
5. Kindwall K E, Brown J, Josephson M E. Electrocardiographic criteria for ventricular tachycardia in wide complex left bundle branch block morphology tachycardias. Am J Cardiol. 1988; 61(15):1279-83.
6. Brugada P, Brugada J, Mont L, Smeets J, Andries E W. A new approach to the differential diagnosis of a regular tachycardia with a wide QRS complex. Circulation. 1991; 83(5):1649-59.
7. Griffith M J, de Belder M A, Linker N J, Ward D E, Camm A J. Multivariate analysis to simplify the differential diagnosis of broad complex tachycardia. Br Heart J. 1991; 66(2):166-74.
8. Griffith M J, Garratt C J, Mounsey P, Camm A J. Ventricular tachycardia as default diagnosis in broad complex tachycardia. Lancet. 1994; 343(8894):386-8.
9. Steurer G, Gursoy S, Frey B, Simonis F, Andries E, Kuck K, et al. The differential diagnosis on the electrocardiogram between ventricular tachycardia and preexcited tachycardia. Clin Cardiol. 1994; 17(6):306-8.
10. Lau E W, Pathamanathan R K, Ng G A, Cooper J, Skehan J D, Griffith M J. The Bayesian approach improves the electrocardiographic diagnosis of broad complex tachycardia. Pacing Clin Electrophysiol. 2000; 23(10 Pt 1):1519-26.
11. Vereckei A, Duray G, Szenasi G, Altemose G T, Miller J M. Application of a new algorithm in the differential diagnosis of wide QRS complex tachycardia. Eur Heart J. 2007; 28(5):589-600.
12. Vereckei A, Duray G, Szenasi G, Altemose G T, Miller J M. New algorithm using only lead aVR for differential diagnosis of wide QRS complex tachycardia. Heart Rhythm. 2008; 5(1):89-98.
13. Sasaki K. A New, Simple Algorithm for Diagnosing Wide QRS Complex Tachycardia: Comparison With Brugada, Vereckei and aVR Algorithms. Circulation. 2009; 120(Issue Supplement 18).
14. Pava L F, Perafan P, Badiel M, Arango J J, Mont L, Morillo C A, et al. R-wave peak time at DII: a new criterion for differentiating between wide complex QRS tachycardias. Heart Rhythm. 2010; 7(7):922-6.
15. Jastrzebski M, Sasaki K, Kukla P, Fijorek K, Stec S, Czarnecka D. The ventricular tachycardia score: a novel approach to electrocardiographic diagnosis of ventricular tachycardia. Europace. 2016; 18(4):578-84.
16. Dongas J, Lehmann M H, Mahmud R, Denker S, Soni J, Akhtar M. Value of preexisting bundle branch block in the electrocardiographic differentiation of supraventricular from ventricular origin of wide QRS tachycardia. The American journal of cardiology. 1985; 55(6):717-21.

17. Alberca T, Almendral J, Sanz P, Almazan A, Cantalapiedra J L, Delcan J L. Evaluation of the specificity of morphological electrocardiographic criteria for the differential diagnosis of wide QRS complex tachycardia in patients with intraventricular conduction defects. Circulation. 1997; 96(10):3527-33.
18. Miller J M, Das M K, Yadav A V, Bhakta D, Nair G, Alberte C. Value of the 12-lead ECG in wide QRS tachycardia. Cardiol Clin. 2006; 24(3):439-51, ix-x.
19. Drew B J, Scheinman M M. ECG criteria to distinguish between aberrantly conducted supraventricular tachycardia and ventricular tachycardia: practical aspects for the immediate care setting. Pacing Clin Electrophysiol. 1995; 18(12 Pt 1):2194-208.
20. Datino T, Almendral J, Avila P, Gonzalez-Torrecilla E, Atienza F, Arenal A, et al. Specificity of electrocardiographic criteria for the differential diagnosis of wide QRS complex tachycardia in patients with intraventricular conduction defect. Heart Rhythm. 2013; 10(9):1393-401.
21. Isenhour J L, Craig S, Gibbs M, Littmann L, Rose G, Risch R. Wide-complex tachycardia: continued evaluation of diagnostic criteria. Acad Emerg Med. 2000; 7(7): 769-73.
22. Lau E W, Ng G A. Comparison of the performance of three diagnostic algorithms for regular broad complex tachycardia in practical application. Pacing Clin Electrophysiol. 2002; 25(5): 822-7.
23. Baxi R P, Hart K W, Vereckei A, Miller J, Chung S, Chang W, et al. Vereckei criteria used as a diagnostic tool by emergency medicine residents to distinguish between ventricular tachycardia and supra-ventricular tachycardia with aberrancy. J Cardiol. 2012; 59(3):307-12.
24. Jastrzebski M, Kukla P, Czarnecka D, Kawecka-Jaszcz K. Specificity of the wide QRS complex tachycardia algorithms in recipients of cardiac resynchronization therapy. J Electrocardiol. 2012; 45(3):319-26.
25. Jastrzebski M, Kukla P, Czarnecka D, Kawecka-Jaszcz K. Comparison of five electrocardiographic methods for differentiation of wide QRS-complex tachycardias. Europace. 2012; 14(8):1165-71.
26. Szelenyi Z, Duray G, Katona G, Frituz G, Szego E, Kovacs E, et al. Comparison of the "real-life" diagnostic value of two recently published electrocardiogram methods for the differential diagnosis of wide QRS complex tachycardias. Acad Emerg Med. 2013; 20(11):1121-30.
27. Kaiser E, Darrieux F C, Barbosa S A, Grinberg R, Assis-Carmo A, Sousa J C, et al. Differential diagnosis of wide QRS tachycardias: comparison of two electrocardiographic algorithms. Europace. 2015; 17(9):1422-7.
28. May A, Brenes-Salazar J, Vaidya V, Ternus B, Kebed D, Brady P. Multistep electrocardiographic algorithms demonstrate inferior specificity for identifying ventricular tachycardia when applied by non-cardiologists. Europace [Internet]. 2015; 17((Supplement 3), iii156).
29. Griffith M J, Debelder M A, Linker N J, Ward D E, Camm A J. Difficulties in the Use of Electrocardiographic Criteria for the Differential-Diagnosis of Left-Bundle-Branch Block Pattern Tachycardia in Patients with a Structurally Normal Heart. European Heart Journal. 1992; 13(4):478-83.
30. Herbert M E, Votey S R, Morgan M T, Cameron P, Dziukas L. Failure to agree on the electrocardiographic diagnosis of ventricular tachycardia. Ann Emerg Med. 1996; 27(1):35-8.
31. Ceresnak S R, Liberman L, Avasarala K, Tanel R, Motonaga K S, Dubin A M. Are wide complex tachycardia algorithms applicable in children and patients with congenital heart disease? J Electrocardiol. 2010; 43(6): 694-700.

What is claimed is:

1. A computerized method of classifying a wide complex heart beat(s) comprising: providing a computing device having an input/output interface, one or more processors, and a memory; receiving one or more wide complex heart beat waveform amplitudes and/or time-voltage areas and one or more baseline heart beat waveform amplitudes and/or time-voltage areas via the input/output interface or the memory; determining a classification probability based on the one or more wide complex heart beat waveform amplitudes and/or time-voltage areas and the one or more baseline heart beat waveform amplitudes and/or time-voltage areas using the one or more processors; determining a signal change based on the classification probability; the determination of a signal change comprising automatically determining a wide complex heart beat classification for the wide complex heart beat(s) by comparing the classification probability to a predetermined value using the one or more processors, wherein the classification probability comprises a ventricular tachycardia (VT) probability; wherein the wide complex heart beat classification comprises the ventricular source or the supraventricular aberrant condition and the wide complex heart beat classification comprises a VT whenever the VT probability is greater than or equal to the predetermined value; and the wide complex heart beat classification comprises a supraventricular wide complex tachycardia (SWCT) whenever the VT probability is less than the predetermined value;

providing the wide complex heart beat classification via the input/output interface;

providing a recommendation to select or exclude a therapy, medication, diagnostic testing or referral for a patient based on the signal change; and selecting or excluding the therapy, medication, diagnostic testing or referral for the patient based on the recommendation.

2. The method of claim 1, wherein the signal change further provides the indication whether the wide complex heart beat(s) is due to ventricular pacing.

3. The method of claim 1, wherein: the wide complex heart beat(s) comprise a wide complex tachycardia (WCT); the ventricular source comprises a VT; and the supraventricular aberrant condition comprises a SWCT.

4. The method of claim 1, further comprising selecting the predetermined value from a range of 0% to 100%.

5. The method of claim 1, wherein the predetermined value comprises about 1%, 10%, 25%, 50%, 75%, 90% or 99%.

6. The method of claim 1, wherein providing the signal change comprises providing a "shock" signal, a "no shock" signal, or no signal.

7. The method of claim 1, further comprising obtaining the one or more wide complex heart beat waveform amplitudes and/or time-voltage areas and the one or more baseline heart beat waveform amplitudes and/or time-voltage areas from an electrocardiogram (ECG) QRS signal, a ventricular electrogram (EMG) signal, and/or a vectorcardiogram (VCG) signal.

8. The method of claim 1, wherein:
the one or more wide complex heart beat waveform amplitudes and/or time-voltage areas comprise a plurality of measured amplitudes and/or time-voltage areas of a ECG QRS waveform, a EMG waveform, and/or a VCG waveform above and below an isoelectric baseline; and the one or more baseline heart beat waveform amplitudes and/or time-voltage areas comprise a plurality of measured amplitudes and/or time-voltage areas of a baseline ECG QRS waveform, a baseline EMG waveform, and/or a baseline VCG waveform above and below the isoelectric baseline.

9. The method of claim 1, wherein receiving the one or more wide complex heart beat waveform amplitudes and/or time-voltage areas, and one or more baseline heart beat waveform amplitudes and/or time-voltage areas comprises:
   receiving a ECG QRS data, a EMG data, a VCG data, and/or a mathematically synthesized VCG data via the input/output interface or the memory;
   receiving a baseline ECG QRS data, a baseline EMG data, and/or a baseline VCG data via the input/output interface or the memory;
   determining the one or more wide complex heart beat waveform amplitudes and/or time-voltage areas from the ECG QRS data, the EMG data, and/or the VCG data using the one or more processors; and
   determining the one or more baseline heart beat waveform amplitudes and/or time-voltage areas from the baseline ECG QRS data, the baseline EMG data, and/or the baseline VCG data using the one or more processors.

10. The method of claim 9, wherein the ECG QRS data, the EMG data, and/or the VCG data is generated or recorded before or after the baseline ECG QRS data, the baseline EMG data, and/or the baseline VCG data.

11. The method of claim 9, wherein the ECG QRS data, the EMG data, and/or the VCG data is generated or recorded after the baseline ECG QRS data, the baseline EMG data, and/or the baseline VCG data and determining the classification probability.

12. The method of claim 9, further comprising generating or recording the ECG QRS data, the EMG data, and/or the VCG data and the baseline ECG QRS data, the baseline EMG data, and/or the baseline VCG data using one or more sensors or devices.

13. The method of claim 12, wherein the one or more sensors or devices comprise a 12-lead ECG device, a continuous ECG telemetry monitor, a stress testing system, an extended monitoring device, a smartphone-enabled ECG medical device, a cardioverter-defibrillator therapy device, a subcutaneous implantable cardioverter defibrillators (ICD), a pacemaker, an automated external defibrillators (AED), or an automatic implantable cardioverter defibrillator (AICD).

14. The method of claim 12, wherein:
   the computing device is integrated into the one or more sensors or devices; or
   the one or more sensors or devices are integrated into the computing device.

15. The method of claim 1, wherein determining the classification probability between the one or more wide complex heart beat waveform amplitudes and/or time-voltage areas and the one or more baseline heart beat waveform amplitudes and/or time-voltage areas comprises:
   receiving a wide complex heart beat waveform duration via the input/output interface or the memory;
   determining, using the one or more processors, a percent amplitude change (PAC) based on the one or more wide complex heart beat waveform amplitudes and the one or more baseline wide complex heart beat waveform amplitudes, and/or a percent time-voltage area change (PTVAC) based on the one or more wide complex heart beat waveform time-voltage areas and the one or more baseline wide complex heart beat waveform time-voltage areas;
   determining the classification probability based on the wide complex heart beat waveform duration, and the PAC and/or the PTVAC using the one or more processors; and
   wherein the classification probability comprises a VT probability, a SWCT probability, or a ventricular pacing probability.

16. The method of claim 15, wherein determining the classification probability is further determined based one or more additional classification predictors.

17. The method of claim 15, wherein:
   the PAC comprises a frontal PAC and a horizontal PAC; and
   the PTVAC comprises a frontal PTVAC and a horizontal PTVAC.

18. The method of claim 1, wherein determining the classification probability between the one or more wide complex heart beat waveform amplitudes and/or time-voltage areas and the one or more baseline heart beat waveform amplitudes and/or time-voltage areas comprises:
   receiving a WCT QRS duration via the input/output interface or the memory;
   the one or more wide complex heart beat waveform amplitudes and/or time-voltage areas comprise one or more frontal plane WCT positive waveform amplitudes and/or time-voltage areas, one or more horizontal plane WCT positive waveform amplitudes and/or time-voltage areas, one or more frontal plane WCT negative waveform amplitudes and/or time-voltage areas, and one or more horizontal plane WCT negative waveform amplitudes and/or time-voltage areas;
   the one or more the baseline heart beat waveform amplitudes and/or time-voltage areas comprise one or more frontal plane baseline positive waveform amplitudes and/or time-voltage areas, one or more horizontal plane baseline positive waveform amplitudes and/or time-voltage areas, one or more frontal plane baseline negative waveform amplitudes and/or time-voltage areas, and one or more horizontal baseline negative waveform amplitudes and/or time-voltage areas;
   determining (1) a frontal percent amplitude change (PAC) based on the one or more frontal plane WCT positive waveform amplitudes, one or more frontal plane WCT negative waveform amplitudes, one or more frontal plane baseline positive waveform amplitudes, and one or more frontal plane baseline negative waveform amplitudes, and/or (2) a frontal percent time-voltage area (PTVAC) based on the one or more frontal plane WCT positive waveform time-voltage areas, one or more frontal plane WCT negative waveform time-voltage areas, one or more frontal plane baseline positive waveform time-voltage areas, and one or more frontal plane baseline negative waveform time-voltage areas;
   determining (1) a horizontal PAC based on the one or more horizontal plane WCT positive waveform amplitudes, one or more horizontal plane WCT negative waveform amplitudes, one or more horizontal plane baseline positive waveform amplitudes, and one or more horizontal baseline negative waveform amplitudes, and/or (2) a horizontal PTVAC based on the one or more horizontal plane WCT positive waveform time-voltage areas, one or more horizontal plane WCT negative waveform time-voltage areas, one or more horizontal plane baseline positive waveform time-voltage areas, and one or more horizontal baseline negative waveform time-voltage areas;

determining a VT probability using a statistical or machine learning process based on the WCT QRS duration and (1) the frontal PAC and the horizontal PAC, and/or (2) the frontal PTVAC and the horizontal PTVAC; and wherein the classification probability comprises the VT probability.

19. The method of claim 18, wherein the statistical or machine learning process comprises a linear regression algorithm, a logistic regression model, a linear discriminate analysis algorithm, a Naive Bayes algorithm, a computational model using artificial neural networks, a computational model based on classification or regression trees, a k-nearest neighbors based model, a support vector machine based model, a boosting algorithm, or an ensemble machine learning algorithm.

20. The method of claim 18, wherein:
the frontal PAC is determined by $$\text{Frontal } PAC(\%) = \left(\frac{\text{Frontal } AAC}{\text{Frontal } BA}\right) \times 100,$$

where:
Frontal AAC=$TAC_{aVR}+TAC_{aVL}+TAC_{aVF}$,
Frontal BA=$TBA_{aVR}+TBA_{aVL}+TBA_{aVF}$,
$TAC_{LeadX}=APC_{LeadX}+ANC_{LeadX}$,
$TBA_{Baseline:LeadX}=(-)\text{Amplitude}_{Baseline:LeadX}+(+)\text{Amplitude}_{Baseline:LeadX}$,
$APC_{LeadX}=|(+)\text{Amplitude}_{WCT:LeadX}-(+)\text{Amplitude}_{Baseline:LeadX}|$,
$ANC_{LeadX}=|(-)\text{Amplitude}_{WCT:LeadX}-(-)\text{Amplitude}_{Baseline:LeadX}|$,
LeadX denotes V1, V4, V6 (horizontal plane) or aVL, aVR, aVF (frontal plane);
the horizontal PAC is determined by $$\text{Horizontal } PAC(\%) = \left(\frac{\text{Horizontal } AAC}{\text{Horizontal } BA}\right) \times 100,$$

where:
Horizontal AAC=$TAC_{V1}+TAC_{V4}+TAC_{V6}$,
Horizontal BA=$TBA_{V1}+TBA_{V4}+TBA_{V6}$; and
the VT probability ($P_{VT}$) is determined by:

$$P_{VT} = \frac{e^{(a+b \times WCT_{duration}+c \times PAC_{frontal}+d \times PAC_{horizontal})}}{1+e^{(a+b \times WCT_{duration}+c \times PAC_{frontal}+d \times PAC_{horizontal})}},$$

where: a, b, c and d are constants.

21. The method of claim 18, wherein:
the frontal PTVAC is determined by $$\text{Frontal } PTVAC(\%) = \left(\frac{\text{Frontal } ATVAC}{\text{Frontal } BTVA}\right) \times 100,$$

where:
Frontal ATVAC=$TTVAC_{aVR}+TTVAC_{aVL}+TTVAC_{aVF}$,
Frontal BTVA=$TBTVA_{aVR}+TBTVA_{aVL}+TBTVA_{aVF}$,
$TTVAC_{LeadX}=TVAPC_{LeadX}+TVANC_{LeadX}$,
$TBTVA_{Baseline:LeadX}=(-)\text{TimeVoltageArea}_{Baseline:LeadX}+(+)\text{TimeVoltageArea}_{Baseline:LeadX}$,
$TVAPC_{LeadX}=|(+)\text{TimeVoltageArea}_{WCT:LeadX}-(+)\text{TimeVoltageArea}_{Baseline:LeadX}|$,
$TVANC_{LeadX}=|(-)\text{TimeVoltageArea}_{WCT:LeadX}-(-)\text{TimeVoltageArea}_{Baseline:LeadX}|$,
LeadX denotes V1, V4, V6 (horizontal plane) or aVL, aVR, aVF (frontal plane);
the horizontal PTVAC is determined by $$\text{Horizontal } PTVAC(\%) = \left(\frac{\text{Horizontal } ATVAC}{\text{Horizontal } BTVA}\right) \times 100,$$

where:
Horizontal ATVAC=$TTVAC_{V1}+TTVAC_{V4}+TTVAC_{V6}$,
Horizontal BTVA=$TBTVA_{V1}+TBTVA_{V4}+TBTVA_{V6}$; and
the VT probability (P) is determined by:

$$P_{VT} = \frac{e^{(a+b \times WCT_{duration}+c \times PTVAC_{frontal}+d \times PTVAC_{horizontal})}}{1+e^{(a+b \times WCT_{duration}+c \times PTVAC_{frontal}+d \times PTVAC_{horizontal})}},$$

where: a, b, c and d are constants.

22. The method of claim 1, wherein the input/output interface comprises a remote device, and the remote device is communicably coupled to the one or more processors via one or more networks.

23. The method of claim 1, wherein the computing device comprises a server computer, a workstation computer, a laptop computer, a mobile communications device, a personal data assistant, or a medical device.

24. An apparatus for classifying a wide complex heart beat(s) comprising: an input/output interface; a memory; one or more processors communicably coupled to the input/output interface and the memory, wherein the one or more processors: receive one or more wide complex heart beat waveform amplitudes and/or time-voltage areas and one or more baseline heart beat waveform amplitudes and/or time-voltage areas via the input/output interface or the memory, determine a classification probability between the one or more wide complex heart beat waveform amplitudes and/or time-voltage areas and the one or more baseline heart beat waveform amplitudes and/or time-voltage areas using the one or more processors, determine a signal change based on the classification probability, the determination of a signal change comprising automatically determining a wide complex heart beat classification for the wide complex heart beat(s) by comparing the classification probability to a predetermined value using the one or more processors, wherein the classification probability comprises a ventricular tachycardia (VT) probability; wherein the wide complex heart beat classification comprises the ventricular source or the supraventricular aberrant condition and the wide complex heart beat classification comprises a VT whenever the VT probability is greater than or equal to the predetermined value; and the wide complex heart beat classification comprises a supraventricular wide complex tachycardia (SWCT) whenever the VT probability is less than the predetermined value; providing the wide complex heart beat classification via the input/output interface;

and wherein a recommendation to select or exclude a therapy, medication, diagnostic testing or referral for a patient based on the signal change is provided, and the therapy, medication, diagnostic testing or referral for the patient is selected or excluded based on the recommendation.

25. The apparatus of claim 24, wherein the signal change further provides the indication whether the wide complex heart beat(s) is due to ventricular pacing.

26. The apparatus of claim 24, wherein: the wide complex heart beat(s) comprise a wide complex tachycardia (WCT); the ventricular source comprises a VT; and the supraventricular aberrant condition comprises a SWCT.

27. The apparatus of claim 24, further comprising selecting the predetermined value from a range of 0% to 100%.

28. The apparatus of claim 24, wherein the predetermined value comprises about 1%, 10%, 25%, 50%, 75%, 90% or 99%.

29. The apparatus of claim 24, wherein providing the signal change comprises providing a "shock" signal, a "no shock" signal, or no signal.

30. The apparatus of claim 24, wherein the one or more wide complex heart beat waveform amplitudes and/or time-voltage areas and the one or more baseline heart beat waveform amplitudes and/or time-voltage areas are obtained from an electrocardiogram (ECG) QRS signal, a ventricular electrogram (EMG) signal, and/or a vectorcardiogram (VCG) signal.

31. The apparatus of claim 24, wherein:
the one or more wide complex heart beat waveform amplitudes and/or time-voltage areas comprise a plurality of measured amplitudes and/or time-voltage areas of a ECG QRS waveform, a EMG waveform, and/or a VCG waveform above and below an isoelectric baseline; and
the one or more baseline heart beat waveform amplitudes and/or time-voltage areas comprise a plurality of measured amplitudes and/or time-voltage areas of a baseline ECG QRS waveform, a baseline EMG waveform, and/or a baseline VCG waveform above and below the isoelectric baseline.

32. The apparatus of claim 24, wherein the one or more processors receive the one or more wide complex heart beat waveform amplitudes and/or time-voltage areas, and one or more baseline heart beat waveform amplitudes and/or time-voltage areas by:
receiving a ECG QRS data, a EMG data, a VCG data, and/or a mathematically synthesized VCG data via the input/output interface or the memory;
receiving a baseline ECG QRS data, a baseline EMG data, and/or a baseline VCG data via the input/output interface or the memory;
determining the one or more wide complex heart beat waveform amplitudes and/or time-voltage areas from the ECG QRS data, the EMG data, and/or the VCG data; and
determining the one or more baseline heart beat waveform amplitudes and/or time-voltage areas from the baseline ECG QRS data, the baseline EMG data, and/or the baseline VCG data.

33. The apparatus of claim 32, wherein the ECG QRS data, the EMG data, and/or the VCG data is generated or recorded before or after the baseline ECG QRS data, the baseline EMG data, and/or the baseline VCG data.

34. The apparatus of claim 32, wherein the ECG QRS data, the EMG data, and/or the VCG data is generated or recorded after the baseline ECG QRS data, the baseline EMG data, and/or the baseline VCG data and determining the classification probability.

35. The apparatus of claim 32, wherein the ECG QRS data, the EMG data, and/or the VCG data and the baseline ECG QRS data, the baseline EMG data, and/or the baseline VCG data are generated or recorded using one or more sensors or devices.

36. The apparatus of claim 35, wherein the one or more sensors or devices comprise a 12-lead ECG device, a continuous ECG telemetry monitor, a stress testing system, an extended monitoring device, a smartphone-enabled ECG medical device, a cardioverter-defibrillator therapy device, a subcutaneous implantable cardioverter defibrillators (ICD), a pacemaker, an automated external defibrillators (AED), or an automatic implantable cardioverter defibrillator (AICD).

37. The apparatus of claim 35, wherein:
the input/output interface, the memory and the one or more processors are integrated into the one or more sensors or devices; or
the one or more sensors or devices are integrated into a computing device comprising the input/output interface, the memory and the one or more processors.

38. The apparatus of claim 24, wherein the one or more processors determine the classification probability between the one or more wide complex heart beat waveform amplitudes and/or time-voltage areas and the one or more baseline heart beat waveform amplitudes and/or time-voltage areas by:
receiving a wide complex heart beat waveform duration via the input/output interface or the memory;
determining a percent amplitude change (PAC) based on the one or more wide complex heart beat waveform amplitudes and the one or more baseline wide complex heart beat waveform amplitudes, and/or a percent time-voltage area change (PTVAC) based on the one or more wide complex heart beat waveform time-voltage areas and the one or more baseline wide complex heart beat waveform time-voltage areas;
determining the classification probability based on the wide complex heart beat waveform duration, and the PAC and/or the PTVAC; and
wherein the classification probability comprises a VT probability, a SWCT probability, or a ventricular pacing probability.

39. The apparatus of claim 38, wherein determining the classification probability is further determined based one or more additional classification predictor.

40. The apparatus of claim 38, wherein:
the PAC comprises a frontal PAC and a horizontal PAC; and
the PTVAC comprises a frontal PTVAC and a horizontal PTVAC.

41. The apparatus of claim 38, wherein the one or more processors determine the classification probability between the one or more wide complex heart beat waveform amplitudes and/or time-voltage areas and the one or more baseline heart beat waveform amplitudes and/or time-voltage areas by:
receiving a WCT QRS duration via the input/output interface or the memory;
the one or more wide complex heart beat waveform amplitudes and/or time-voltage areas comprise one or more frontal plane WCT positive waveform amplitudes and/or time-voltage areas, one or more horizontal plane WCT positive waveform amplitudes and/or time-voltage areas, one or more frontal plane WCT negative waveform amplitudes and/or time-voltage areas, and one or more horizontal plane WCT negative waveform amplitudes and/or time-voltage areas;

the one or more the baseline heart beat waveform amplitudes and/or time-voltage areas comprise one or more frontal plane baseline positive waveform amplitudes and/or time-voltage areas, one or more horizontal plane baseline positive waveform amplitudes and/or time-voltage areas, one or more frontal plane baseline negative waveform amplitudes and/or time-voltage areas, and one or more horizontal baseline negative waveform amplitudes and/or time-voltage areas;

determining (1) a frontal percent amplitude change (PAC) based on the one or more frontal plane WCT positive waveform amplitudes, one or more frontal plane WCT negative waveform amplitudes, one or more frontal plane baseline positive waveform amplitudes, and one or more frontal plane baseline negative waveform amplitudes, and/or (2) a frontal percent time-voltage area (PTVAC) based on the one or more frontal plane WCT positive waveform time-voltage areas, one or more frontal plane WCT negative waveform time-voltage areas, one or more frontal plane baseline positive waveform time-voltage areas, and one or more frontal plane baseline negative waveform time-voltage areas;

determining (1) a horizontal PAC based on the one or more horizontal plane WCT positive waveform amplitudes, one or more horizontal plane WCT negative waveform amplitudes, one or more horizontal plane baseline positive waveform amplitudes, and one or more horizontal baseline negative waveform amplitudes, and/or (2) a horizontal PTVAC based on the one or more horizontal plane WCT positive waveform time-voltage areas, one or more horizontal plane WCT negative waveform time-voltage areas, one or more horizontal plane baseline positive waveform time-voltage areas, and one or more horizontal baseline negative waveform time-voltage areas;

determining a VT probability using a statistical or machine learning process based on the WCT QRS duration and (1) the frontal PAC and the horizontal PAC, and/or (2) the frontal PTVAC and the horizontal PTVAC; and wherein the classification probability comprises the VT probability.

42. The apparatus of claim 41, wherein the statistical or machine learning process comprises a linear regression algorithm, a logistic regression model, a linear discriminate analysis algorithm, a Naive Bayes algorithm, a computational model using artificial neural networks, a computational model based on classification or regression trees, a k-nearest neighbors based model, a support vector machine based model, a boosting algorithm, or an ensemble machine learning algorithm.

43. The apparatus of claim 41, wherein:
the frontal PAC is determined by $$\text{Frontal } PAC(\%) = \left(\frac{\text{Frontal } AAC}{\text{Frontal } BA}\right) \times 100,$$

where:
Frontal AAC=$TAC_{aVR}$+$TAC_{aVL}$+$TAC_{aVF}$,
Frontal BA=$TBA_{aVR}$+$TBA_{aVL}$+$TBA_{aVF}$,
$TAC_{LeadX}$=$APC_{LeadX}$+$ANC_{LeadX}$,
$TBA_{Baseline:LeadX}$=(−)Amplitude$_{Baseline:LeadX}$+(+)Amplitude$_{Baseline:LeadX}$, $APC_{LeadX}$=|(+)Amplitude$_{WCT:LeadX}$−(+)Amplitude$_{Baseline:LeadX}$|,
$ANC_{LeadX}$=|(−)Amplitude$_{WCT:LeadX}$−Amplitude$_{Baseline:LeadX}$|, LeadX denotes V1, V4, V6 (horizontal plane) or aVL, aVR, aVF (frontal plane);
the horizontal PAC is determined by $$\text{Horizontal } PAC(\%) = \left(\frac{\text{Horizontal } AAC}{\text{Horizontal } BA}\right) \times 100,$$

where:
Horizontal AAC=$TAC_{V1}$+$TAC_{V4}$+$TAC_{V6}$,
Horizontal BA=$TBA_{V1}$+$TBA_{V4}$+$TBA_{V6}$; and
the VT probability (P) is determined by:

$$P_{VT} = \frac{e^{(a+b\times WCT_{duration}+c\times PAC_{frontal}+d\times PAC_{horizontal})}}{1+e^{(a+b\times WCT_{duration}+c\times PAC_{frontal}+d\times PAC_{horizontal})}},$$

where: a, b, c and d are constants.

44. The apparatus of claim 41, wherein:
the frontal PTVAC is determined by $$\text{Frontal } PTVAC(\%) = \left(\frac{\text{Frontal } ATVAC}{\text{Frontal } BTVA}\right) \times 100,$$

where:
Frontal ATVAC=$TTVAC_{aVR}$+$TTVAC_{aVL}$+$TTVAC_{aVF}$,
Frontal BTVA=$TBTVA_{aVR}$+$TBTVA_{aVL}$+$TBTVA_{aVF}$,
$TTVAC_{ECGleadX}$=$TVAPC_{LeadX}$+$TVANC_{LeadX}$, $TBTVA_{BaselineLeadX}$=(−)TimeVoltageArea$_{Baseline:LeadX}$+(+)TimeVoltageArea$_{Baseline:LeadX}$, $TVAPC_{LeadX}$=|(+)TimeVoltageArea$_{WCT:LeadX}$−(+)TimeVoltageArea$_{Baseline:LeadX}$|, $TVANC_{LeadX}$=|(−)TimeVoltageArea$_{WCT:LeadX}$−(−)TimeVoltageArea$_{Baseline:LeadX}$|, LeadX denotes V1, V4, V6 (horizontal plane) or aVL, aVR, aVF (frontal plane);
the horizontal PTVAC is determined by $$\text{Horizontal } PTVAC(\%) = \left(\frac{\text{Horizontal } ATVAC}{\text{Horizontal } BTVA}\right) \times 100,$$

where:
Horizontal ATVAC=$TTVAC_{V1}$+$TTVAC_{V4}$+$TTVAC_{V6}$,
Horizontal BTVA=$TBTVA_{V1}$+$TBTVA_{V4}$+$TBTVA_{V6}$; and
the VT probability (P) is determined by:

$$P_{VT} = \frac{e^{(a+b\times WCT_{duration}+c\times PTVAC_{frontal}+d\times PTVAC_{horizontal})}}{1+e^{(a+b\times WCT_{duration}+c\times PTVAC_{frontal}+d\times PTVAC_{horizontal})}},$$

where: a, b, c and d are constants.

45. The apparatus of claim 24, wherein the input/output interface comprises a remote device, and the remote device is communicably coupled to the one or more processors via one or more networks.

46. The apparatus of claim 24, wherein the apparatus comprises a server computer, a workstation computer, a laptop computer, a mobile communications device, a personal data assistant, or a medical device.

\* \* \* \* \*